(12) United States Patent
Kemter et al.

(10) Patent No.: US 11,166,915 B2
(45) Date of Patent: Nov. 9, 2021

(54) METHOD FOR OBTAINING EFFICIENT VIRAL VECTOR-BASED COMPOSITIONS FOR VACCINATION OR GENE THERAPY

(71) Applicant: Leukocare AG, Martinsried (DE)

(72) Inventors: Kristina Kemter, Garching bei München (DE); Martin Scholz, Munich (DE)

(73) Assignee: Leukocare AG, Martinsried (DE)

( * ) Notice: Subject to any disclaimer, the term of this patent is extended or adjusted under 35 U.S.C. 154(b) by 0 days.

(21) Appl. No.: 16/333,726

(22) PCT Filed: Sep. 15, 2017

(86) PCT No.: PCT/EP2017/073370
§ 371 (c)(1),
(2) Date: Mar. 15, 2019

(87) PCT Pub. No.: WO2018/050872
PCT Pub. Date: Mar. 22, 2018

(65) Prior Publication Data
US 2019/0269618 A1  Sep. 5, 2019

(30) Foreign Application Priority Data
Sep. 16, 2016 (EP) ................................... 16189276

(51) Int. Cl.
| | |
|---|---|
| A61K 39/12 | (2006.01) |
| A61K 47/00 | (2006.01) |
| A61K 47/26 | (2006.01) |
| C12N 7/00 | (2006.01) |
| A61K 9/19 | (2006.01) |
| A61K 39/39 | (2006.01) |
| A61K 47/18 | (2017.01) |
| A61K 39/00 | (2006.01) |

(52) U.S. Cl.
CPC ............. *A61K 9/19* (2013.01); *A61K 39/39* (2013.01); *A61K 47/183* (2013.01); *A61K 47/26* (2013.01); *C12N 7/00* (2013.01); *A61K 39/00* (2013.01); *C12N 2710/10023* (2013.01); *C12N 2710/10034* (2013.01); *C12N 2710/10043* (2013.01); *C12N 2710/10051* (2013.01)

(58) Field of Classification Search
None
See application file for complete search history.

(56) References Cited

U.S. PATENT DOCUMENTS

| | | | |
|---|---|---|---|
| 9,610,343 B2 * | 4/2017 | Jin | A61K 39/12 |
| 2008/0071063 A1 | 3/2008 | Allan et al. | |
| 2011/0081380 A1 | 4/2011 | Francon et al. | |
| 2014/0127227 A1 | 5/2014 | Chang | |
| 2014/0127260 A1 * | 5/2014 | Chintala | A61K 9/19 |
| | | | 424/204.1 |
| 2018/0339036 A1 * | 11/2018 | Scholz | A61K 39/12 |
| 2019/0216734 A1 | 7/2019 | Scholz et al. | |
| 2019/0216925 A1 | 7/2019 | Scholz et al. | |

FOREIGN PATENT DOCUMENTS

| | | |
|---|---|---|
| EP | 1854478 A1 | 11/2007 |
| JP | 2009-516519 A | 4/2009 |
| JP | 2014-522827 A | 9/2014 |
| JP | 2014-523243 A | 9/2014 |
| WO | WO2005066333 A1 | 7/2005 |
| WO | WO2007056847 A1 | 5/2007 |
| WO | WO2007104562 A1 | 9/2007 |
| WO | WO2013001034 A1 | 1/2013 |
| WO | WO2013001044 A1 | 1/2013 |
| WO | WO2015005928 A1 | 1/2015 |
| WO | WO2015040234 A1 | 3/2015 |
| WO | WO2015059284 A1 | 4/2015 |
| WO | WO2015140751 A1 | 9/2015 |
| WO | WO2016087457 A1 | 6/2016 |

OTHER PUBLICATIONS

Croyle et al. (1998) Development of a Highly Efficient Purification Process for Recombinant Adenoviral Vectors for Oral Gene Delivery, Pharmaceutical Development and Technology, 3:3, 365-372.*
European Search Report dated Mar. 2, 2017 in European application No. 16189276.5, 13 pages.
International Search Report and Written Opinion dated Nov. 12, 2017 in International application No. PCT/EP2017/073370, 8 pages.
Kissmann et al., "H1N1 influenza virus-like particles: Physical degradation pathways and identification of stabilizers," Feb. 2011, Journal of Pharmaceutical Sciences, 100 (2): 634-645.
Lua et al., "Bioengineering virus-like particles as vaccines," Mar. 2014, Biotechnology and Bioengineering, 111(3): 425-440.

(Continued)

*Primary Examiner* — Nianxiang Zou
(74) *Attorney, Agent, or Firm* — Lee & Hayes, P.C.

(57) ABSTRACT

The present invention relates to a method for preparing viral vector-based compositions wherein the viral vector-based particles present in the composition have a particle size distribution with a polydispersity index (PDI) of less than 0.5, the method comprising the steps: (a) providing replication-deficient viral vectors; (b) providing a solution comprising at least one sugar and at least three different excipients selected from hydrophilic and amphiphilic excipients, wherein the excipients are characterized by polar, aliphatic, aromatic, negatively charged, and/or positively charged functional groups, and wherein the solution is further characterized by an excipient-sugar ratio of at least 1:2 (w/w); and (c) mixing the replication deficient viral vectors of step (a) with the solution of step (b). The present invention further relates to a viral vector-based composition obtainable by the method of the invention as well as to the viral vector-based composition of the invention for use as a prime-boost vaccine.

10 Claims, 30 Drawing Sheets

(56) References Cited

OTHER PUBLICATIONS

Figure 1:
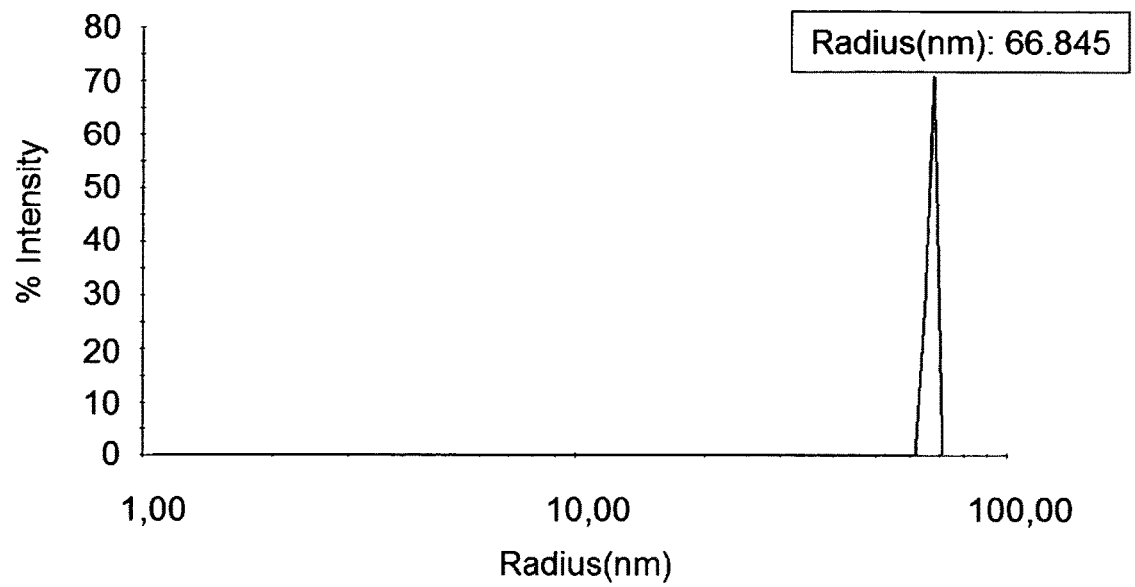
Figure 1:
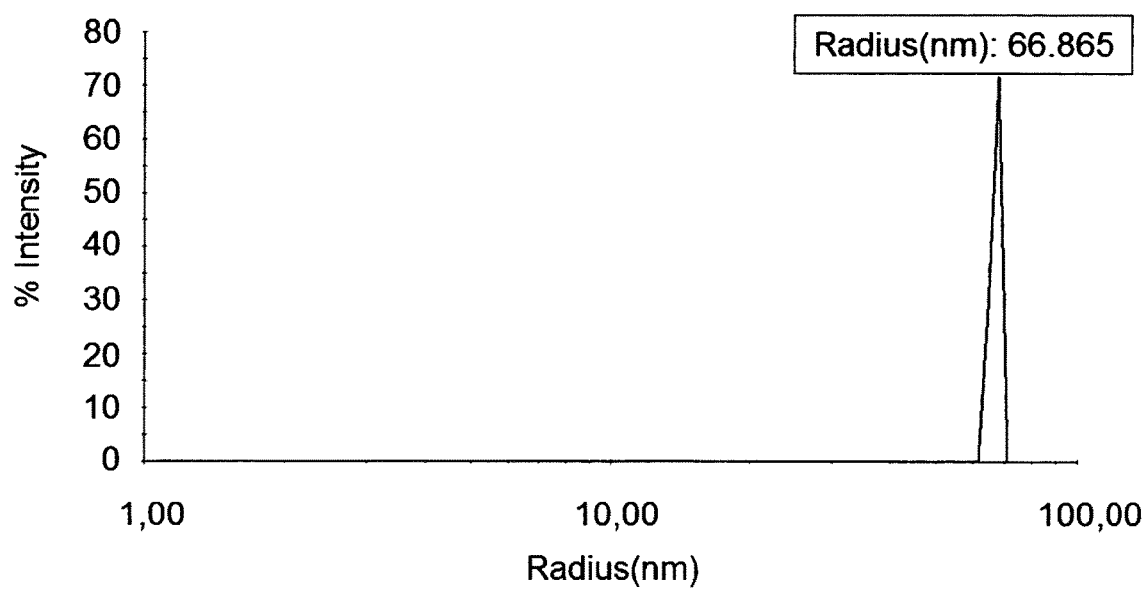
Figure 1:
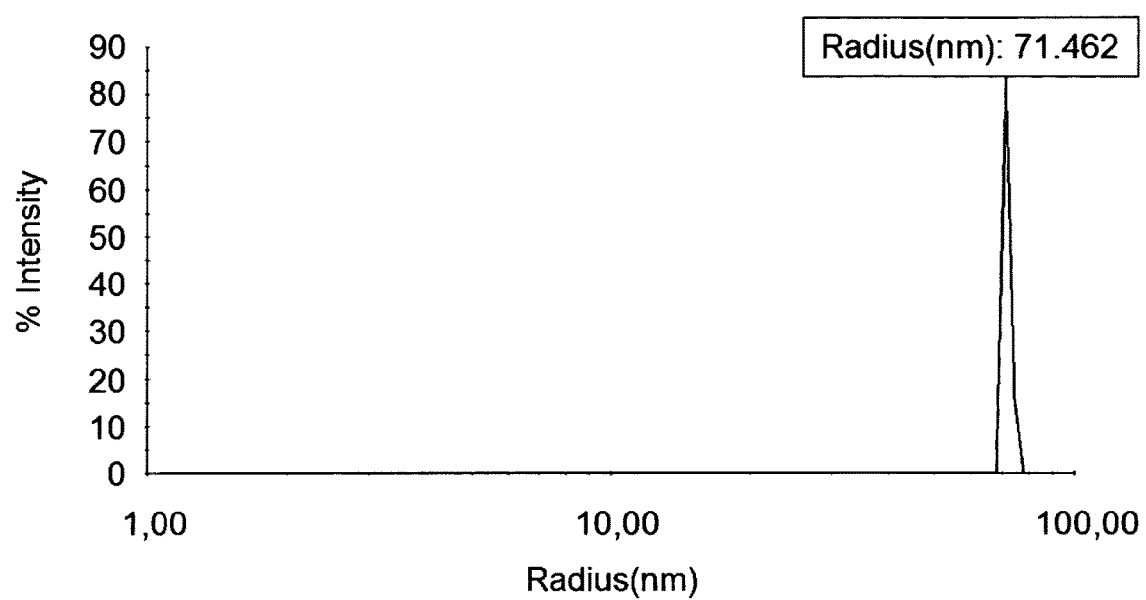

Lynch et al., "Stability studies of HIV-1 Pr55gag virus-like particles made in insect cells after storage in various formulation media," Sep. 2012, Virology Journal, 9(1): 210. 5 pages.
Mohr et al., "Virus-like particle formulation optimization by miniaturized high-throughput screening," May 2013, Methods, 60(3): 248-256.
Chen, et al., "Development of a simple assay system for protein stabilization efficiency based on hemoglobin protection against denaturation and measurement of the cooperative effect of mixing protein stabilizers" May 2016. Bioscience Biotechnology Biochemistry, vol. 80, Iss. 10, 2016, pp. 1874-1878.
European Search Report dated Feb. 24, 2017 in European application No. EP 16189346.6, 6 pages.
International Search Report and Written Opinion dated Oct. 26, 2017 in International application No. PCT/EP2017/073368, 8 pages.
International Search Report and Written Opinion dated Nov. 23, 2017 in International application No. PCT/EP2017/073373, 12 pages.
International Search Report and Written Opinion dated Nov. 24, 2017 in International application No. PCT/EP2017/073374, 10 pages.
Non Final Office Action dated May 1, 2020 for U.S. Appl. No. 16/328,061 "A Novel Method for Stabilization of a Biopharmaceutical Drug Product During Processing" Scholz, 9 pages.
Scherliess et al., "Induction of protective immunity against H1N1 influenza A(H1N1)pdm09 with spray-dried and electron-beam sterilised vaccines in non-human primates," Mar. 2014, Vaccines, 32(19): 2231-2240.
Vazquez-Rey, et al., "Aggregates in Monoclonal Antibody Manufacturing Processes," Apr. 2011, Biotechnology and Bioengineering, 108(7): 1494-1508.
Japanese Office Action dated Jun. 23, 2021 in JP Application No. 2019-514710, a foreign corresponding application of U.S. Appl. No. 16/333,726, 8 pages.
Japanese Office action dated Jun. 24, 2021 in JP Application No. 2019-514711, a foreign corresponding application of U.S. Appl. No. 16/328,061, 10 pages.
Korean Office action dated Aug. 30, 2021 in KR Application No. 10-2019-7010722, a foreign corresponding application of U.S. Appl. No. 16/328,061, 13 pages.

* cited by examiner

A

B

A

B

A

B

A

B

A

B

C

D

A

B

A

B

C

D

A

B

C

D

A

B

C

D

A

B

C

D

A

B

C

D

A

B

C

D

A

* PDI not measurable due to degradation of viral particles

- ■ PBS
- ▨ original supplier formulation 1
- ▨ composition 11
- ▨ composition 12

B

* PDI not measurable due to degradation of viral particles

- ■ PS1: OF1; PS2: PBS
- ▨ PS1: OF1; PS2: comp. 11
- ▨ PS1: OF1; PS2: comp. 12

METHOD FOR OBTAINING EFFICIENT VIRAL VECTOR-BASED COMPOSITIONS FOR VACCINATION OR GENE THERAPY

CROSS REFERENCE TO RELATED APPLICATIONS

This Application is a U.S. National Phase Application of International No. PCT/EP2017/073370, filed Sep. 15, 2017, which claims priority to European Application No. 16189276.5, filed Sep. 16, 2016, which are hereby incorporated by reference in their entirety.

The present invention relates to a method for preparing viral vector-based compositions, wherein the viral vector-based particles present in the composition have a particle size distribution with a polydispersity index (PDI) of less than 0.5, the method comprising the steps: (a) providing replication-deficient viral vectors; (b) providing a solution comprising at least one sugar and at least three different excipients selected from hydrophilic and amphiphilic excipients, wherein the excipients are characterized by polar, aliphatic, aromatic, negatively charged, and/or positively charged functional groups, and wherein the solution is further characterized by an excipient-sugar ratio of at least 1:2; and (c) mixing the replication deficient viral vectors of step (a) with the solution of step (b). The present invention further relates to a viral vector-based composition obtainable by the method of the invention as well as to the viral vector-based composition of the invention for use as a prime-boost vaccine.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Replication-deficient recombinant viral vectors represent a rapidly growing field of vaccine development and gene therapy. When intended for use in vaccination, viral vectors and virus like particles (VLPs) offer a series of advantages over traditional vaccines. In addition to inducing exceptional antibody responses, they also elicit cytotoxic T lymphocytes (CTL) that are crucial for the control of intracellular pathogens and cancer, a feature not observed by protein-based vaccines [Rollier C S et al., 2011]. Many viral species have been evaluated as recombinant vectors for vaccines, including retrovirus, lentivirus, vaccinia virus (e.g. modified vaccinia Ankara virus; MVA), adenovirus, adeno-associated virus, cytomegalovirus, Sendai virus, measles virus and vesicular stomatitis virus (VSV). However, the most widely evaluated vectors to date are adenovirus type 5 and members of the poxvirus family [Rollier C S et al., 2011, Ura T et al. 2014].

A drawback associated with viral vectors, in particular upon manufacturing, storage and distribution, is that they are complex supra-molecular ensembles of macromolecules which are prone to a variety of chemical and physical degradation pathways [Vrdoljak A et al. 2012]. Thus, a major challenge in this field is the reduction (avoidance) of cross-linking and vector particle interaction of neighboring virus particles that is typically caused over a broad range of concentrations by various mechanisms at different stages of production, storage and application. This intrinsic tendency of viral vectors for particle agglomeration of different shapes and sizes within a composition leads to inhomogeneous size distribution of the viral particles and an associated increase in polydispersity. Ultimately, these effects result in a significant loss of therapeutic efficacy, and can even lead to adverse effects at the injection site, most likely due to the increased viscosity observed as a result of said particle agglomeration. Furthermore, aggregation of the viral vectors is also considered to influence biodistribution after administration and, similar to protein pharmaceuticals, aggregation of viral vectors may increase undesired immunogenicity by targeting the vector to antigen presenting cells, thereby inducing or enhancing undesired immune responses to the surface proteins or protein capsids and transgenic products. As high polydispersity is associated with high viscosity, compositions that do not show such unappreciated polydispersity are expected to also lead to better syringeability and injectability. Thus, improved viral vector-based vaccines with low polydispersity and having a more suitable ratio between vector particle distribution and functional efficacy would be highly desired.

Similar considerations apply when viral vectors are intended for use as gene transfer therapeutics. Viral vectors have emerged as safe and effective delivery vehicles for clinical gene therapy, as shown in a series of clinical studies, especially for monogenic recessive disorders, but also for some idiopathic diseases (see e.g. Kotterman M A et al., Viral Vectors for Gene Therapy: Translational and Clinical Outlook. Annu Rev Biomed Eng. 2015 Dec. 7; 17:63-89). These clinical studies were conducted on the basis of vectors that combine low genotoxicity and immunogenicity with highly efficient delivery, including vehicles based on adeno-associated virus and lentivirus, which are increasingly enabling clinical success. Important examples for clinical treatment strategies based on viral vectors include, e.g., stem cell therapy, mucoviscidosis, haemophilia, inherited retinopathy or cystic fibrosis. (Collins M, ThrasherA, Gene therapy: progress and predictions. Proc Biol Sci. 2015; 282). Typically, the viral vectors employed in such gene transfer therapeutics include retrovirus, adenovirus, adeno-associated virus (AAV) and herpes simplex virus.

Also with regard to gene transfer therapeutics, the avoidance of unappreciated polydispersity for obtaining a more suitable ratio between vector particle distribution and functional efficacy of gene transfer vectors is essential for efficient host cell infection and subsequent gene expression. In particular, the in vivo administration of gene therapeutic viral vectors to certain sites, such as the central nervous system, is expected to require small volumes of highly concentrated viral vectors, a feature for which the maximum achievable dose may be limited by the intrinsic property of low vector solubility. Thus, at present, there are still substantial delivery challenges that have to be overcome to extend the success achieved so far to a broad variety of diseases; these challenges include developing techniques to evade pre-existing immunity, to ensure more efficient transduction of therapeutically relevant cell types, to target delivery, and to ensure genomic maintenance.

Formulation development for virus-based viral vector compositions for vaccines or gene-transfer therapeutics is rather difficult, mainly due to their complex molecular structure. Thus, formulation development for viral vector based pharmaceutical compositions is a relatively recent area of investigation and only a few studies and patent applications have been reported describing systematic efforts to optimize viral vector formulations and stability. An important aspect of vector stability is solubility during vector purification, preparation and storage.

U.S. Pat. No. 7,704,721 describes compositions and methods to prevent the aggregation of recombinant adeno associate virus (AAV) virions purified using ultracentrifugation and/or chromatography by adding one or more salts of multivalent ions in high concentrations to produce a preparation of the virions that are nonetheless isotonic with the intended target tissue. This combination of high ionic strength and modest osmolarity is achieved using salts of high valency, such as sodium citrate. High concentrated AAV stock formulations for gene therapy with up to 6.5× $10^{13}$ viral particles per ml can be prepared and stored in this way without aggregation. No aggregation was observed by dynamic light scattering (DSL) even after 10 freeze/thaw cycles. The surfactant Pluronic F68 may be added at 0.001% to prevent losses of virions to surfaces during handling. Virion preparations can also be treated with nucleases to eliminate small nucleic acid strands on virion surfaces that exacerbate aggregation. These highly specific formulations for AAV compositions described in U.S. Pat. No. 7,704,721 are purposely derived from specific intrinsic structural conditions of the AAV virions and require the presence of high amounts of multivalent ions and surfactants as well as an additional nuclease treatment. Thus, these formulations cannot simply be transferred generically to other viral-vector based compositions having a wide range of different properties. Instead, individual adjustments for each new viral-vector based composition are required, depending on the respective individual properties.

WO 2009022174 describes non aggregating virus formulations comprising a virus, preferably an adenovirus, a polyol, preferably glycerol, and a zwitterionic compound, preferably HEPES. Additionally, an assay for viral aggregation using dynamic light scattering (DLS) is described which comprises analyzing the size of viral particles in a sample wherein the particles are in a mixture with polyol and determining from the size whether the sample contains substantially only acceptable non-aggregated particles after repeated freeze and thaw cycles and storage of the compositions at ambient temperature. It is concluded in the document that the composition can be utilized with a wide range of viruses, preferably adenovirus. Although WO 2009022174 describes a non-aggregating virus formulation, said formulations necessarily comprise glycerol and a buffer like the disclosed zwitterionic buffering substance HEPES. However, using a polyol such as glycerol has the drawback of being associated with an increase in unappreciated viscosity, which in turn results in unfavorable syringeability and injectability of a vaccine. The use of the buffering substance HEPES has the additional drawback of the possible appearance of phototoxic effects as a result of the exposure to ambient light and the subsequent formation of hydrogen peroxide.

U.S. Pat. No. 7,888,096 describes liquid and lyophilized adenovirus formulations with improved long term storage stability at 4° C., in terms of infectivity. The liquid and lyophilized formulations are prepared for use in gene therapy, commonly using retroviruses, adenoviruses, or lentiviruses. The authors of U.S. Pat. No. 7,888,096 emphasize that the particles must maintain their biological integrity to be infectious. They further describe for dry formulations the use of a bulking agent for lyophilization (mannitol), a cryoprotectant (sucrose), a lyoprotectant (human serum albumin), several buffers, and salts. The liquid formulation described in U.S. Pat. No. 7,888,096 comprises buffers and polyol and an additional nuclease treatment is required during purification in order to prevent aggregation. As discussed above, polyols may increase unappreciated viscosity in the vaccine product. However, nucleases have the drawback that they may exert unappreciated effects in vivo.

WO 2015040234 describes pharmaceutical adenovirus formulations for use in gene therapy as well as in vaccines, in particular liquid pharmaceutical formulations comprising adenovirus, a histidine buffered solution, trehalose, a salt and a non-ionic detergent, wherein the pH is ranging between 6-7. The resulting formulation has been shown to preserve the quantity, potency (infectivity) and quality of the containing adenoviruses, therewith improving the overall adenoviral stability compared to other formulations known in the art. The adenoviral formulations according to WO 2015040234 are amenable to prolonged storage at 2 to 8° C. for more than 6 months comprising the adenovirus at a titer ranging between $1\times10^7$ and $1\times10^{13}$ virus particles per milliliter. However, the analysis of the recited storage stability of the adenoviral formulations is only based on the combination of a qPCR analysis and a cell culture based infectivity assay. Thermal melting assays using Dynamic light scattering (DLS) analysis were used to analyze the melting temperature of the adenoviral capsid with increasing temperature. The accompanying changes in the polydispersity index were, however, not monitored. Furthermore, changes in polydispersity indices upon purification and storage were also not determined. However, although several physical and chemical instabilities of adenoviral vectors are summarized (e.g. aggregation, deamidation, oxidation, degradation etc.) and the resulting challenges, especially in the stabilization and formulation development of adenoviral vectors, are discussed, the instabilities cited in WO 2015040234 are rather typical for proteins. Thus, the described stabilizing formulations do not address the more complex VLPs and/or viral vectors and their tendency to aggregate with the consequence of higher polydispersity in a suspension.

US20100124557 describes a liquid or liquid-frozen composition comprising a modified vaccinia Ankara (MVA) virus or derivative thereof and mannitol as the sole stabilizing agent of the composition. Mannitol has been shown to exert the stabilizing effect at temperatures between 0° C. to 10° C. in the liquid state and in a liquid-frozen state at temperatures between −10 to −30° C. The storage stability of the MVA virus in the mannitol formulations was only analyzed in cell culture based infectivity assays. However, no changes in the particle size distribution profiles and in the corresponding polydispersity indices upon preparation and storage resulting in loss of function in terms of infectivity were analyzed.

WO 2013001034 describes the utilization of viruses for the generation of viral or bacterial antigens. The stabilization of viral surface molecules is described, thereby enabling a prolonged storage and infectivity of replication competent viruses. In addition, it is described that the antigenicity of proteins is maintained even after irradiation, if the composition comprised amino acids. However, the problem of an increasing polydispersity of non-replicating VLPs or viral vectors in suspensions is not addressed.

All these approaches have in common that the stability of viruses or viral proteins is addressed. For example, maintaining the molecular integrity of viral proteins in replication competent viruses, such as ligands for cellular target molecules, is important for cellular infection. Moreover, the antigenicity of relevant viral proteins is of interest in vaccine development. However, aside from these biological functions, the physical characteristics of particles within a suspension represent an important aspect in vaccine production based on VLP and/or viral vectors. The problem of avoiding an increase in polydispersity of a composition comprising VLPs and/or viral vectors and, by this, the decreased vaccination or gene transfer efficacy, has not been solved so far.

Thus, despite the fact that a lot of effort is currently being invested into the development of novel vaccines or gene transfer therapeutics, there is still a need to provide improved compositions characterized by low and medium polydispersity indices and, thus, a higher ratio between infective particles and non-infective large particles or particle agglomerates within the composition. As a consequence of reducing polydispersity, the efficacy of the vaccine or gene transfer approach could be increased, thus resulting in a reduction of costs, as well as a reduction of adverse events at the injection site and in the body.

This need is addressed by the provision of the embodiments characterized in the claims.

Accordingly, the present invention relates to a method for preparing viral vector-based compositions wherein the viral vector-based particles present in the composition have a particle size distribution with a polydispersity index (PDI) of less than 0.5, the method comprising the steps: (a) providing replication-deficient viral vectors; (b) providing a solution comprising at least one sugar and at least three different excipients selected from hydrophilic and amphiphilic excipients, wherein the excipients are characterized by polar, aliphatic, aromatic, negatively charged, and/or positively charged functional groups, and wherein the solution is further characterized by an excipient-sugar ratio of at least 1:2 (w/w); and (c) mixing the replication deficient viral vectors of step (a) with the solution of step (b).

Viral vectors are commonly used to deliver genetic material into cells in vivo or in vitro. Viruses may efficiently transport their genomes inside the host cells. Virus-like particles resemble viruses, are non-infectious and do not contain viral genetic material. The expression of viral structural proteins, such as Envelope or Capsid, can result in the self-assembly of virus like particles (VLPs). VLPs derived from the Hepatitis B virus may be composed of the HBV surface antigen (HBsAg) (Hyakumura M. et al. J. Virol. 89:11312-22, 2015) or from HBV core (Sominskaya I. et al. PLos One 8:e75938). VLPs have been produced from components of various virus families including Parvoviridae (e.g. adeno-associated virus), Retroviridae (e.g. HIV), Flaviviridae (e.g. Hepatitis C virus) and bacteriophages (e.g. Qβ, AP205). VLPs can be produced in different cell culture systems including bacterial, mammalian, insect, yeast and plant cell lines. The term "viral vector-based composition" as used herein, relates to a composition that comprises at least a viral vector. The term "viral vector", in accordance with the present invention, relates to a carrier, i.e. a "vector" that is derived from a virus. "Viral vectors" in accordance with the present invention include vectors derived from naturally occurring or modified viruses, as well as virus like particles (VLPs).

In general, the starting materials for the development of viral vectors are live viruses. Thus, certain requirements such as safety and specificity need to be fulfilled in order to ensure their suitability for use in animals or in human patients. One important aspect is the avoidance of uncontrolled replication of the viral vector. This is usually achieved by the deletion of a part of the viral genome critical for viral replication. Such a virus can infect target cells without subsequent production of new virions. Moreover, the viral vector should have no effect or only a minimal effect on the physiology of the target cell and rearrangement of the viral vector genome should not occur. Such viral vectors derived from naturally occurring or modified viruses are well known in the art and have been described, e.g. in the Review of Lukashev A N and Zamyatnin A A "Viral Vectors for Gene Therapy: Current State and Clinical Perspectives". Front Mol Neurosci. 2016; 9:56 as well as in the Review of Stoica L and Sena-Esteves M "Adeno Associated Viral Vector Delivered RNAi for Gene Therapy of SOD1 Amyotrophic Lateral Sclerosis", Front Mol Neurosci. 2016 Aug. 2; 9:56.

Also vectors derived from virus like particles are well known in the art and have been described, e.g. in Tegerstedt et al. (Tegerstedt et al. (2005), Murine polyomavirus virus-like particles (VLPs) as vectors for gene and immune therapy and vaccines against viral infections and cancer. Anticancer Res. 25(4):2601-8.). One major advantage of VLPs is that they are not associated with any risk of reassembly as is possible when live attenuated viruses are used as viral vectors and, as such, they represent "replication-deficient viral vectors" in accordance with the present invention. VLP production has the additional advantage that it can be started earlier than production of traditional vaccines once the genetic sequence of a particular virus strain of interest has become available.

VLPs contain repetitive high density displays of viral surface proteins which present conformational viral epitopes that can elicit strong T cell and B cell immune responses. VLPs have already been used to develop FDA approved vaccines for Hepatitis B and human papillomavirus and, moreover, VLPs have been used to develop a pre-clinical vaccine against chikungunya virus. Evidence further suggests that VLP vaccines against influenza virus might be superior in protection against flu viruses over other vaccines. In early clinical trials, VLP vaccines for influenza appeared to provide complete protection against both the Influenza A virus subtype H5N1 and the 1918 flu as reviewed by Quan F S et al., "Progress in developing virus-like particle influenza vaccines". Expert Rev Vaccines. 2016 May 5:1-13.

Highly purified and homogenous VLPs can be formulated as so-called "lipoparticles", which contain high concentrations of a conformationally intact membrane protein of interest. Integral membrane proteins are involved in diverse biological functions and are targeted by nearly 50% of existing therapeutic drugs. However, because of their hydrophobic domains, membrane proteins are difficult to manipulate outside of living cells. Lipoparticles can incorporate a wide variety of structurally intact membrane proteins, including G protein-coupled receptors (GPCR)s, ion channels, and viral envelopes. Lipoparticles may be used as platform for numerous applications including antibody screening, production of immunogens, and ligand binding assays.

Virus-like particles can also be used as drug delivery vectors (Zdanowicz M and Chroboczek J, 2016).

The presence of viral structural proteins, for example, structural proteins in the envelope or in the capsid, can result in the self-assembly of VLPs. In general, VLPs can be produced in a variety of cell culture systems including mammalian cell lines, insect cell lines, yeast, and plant cells and VLPs have been produced from different virus families including parvoviridae (e.g. adeno-associated virus), retroviridae (e.g. HIV), and flaviviridae (e.g. Hepatitis C virus). For example, VLPs derived from the Hepatitis B virus and composed of the small HBV-derived surface antigen (HBsAg) have been described by Sominskaya I et al. Construction and immunological evaluation of multivalent hepatitis B virus (HBV) core virus-like particles carrying HBV and HCV epitopes. Clin Vaccine Immunol. 2010 June; 17:1027-33.

In accordance with the present invention, the term "viral vectors" includes, without being limiting, (i) viral vectors represented by one particular type of viral vector, or (ii) viral vector mixtures of different molecular types of viral vectors.

The composition may, optionally, comprise further molecules capable of altering the characteristics of the viral vector(s). For example, such further molecules can serve to stabilize, modulate and/or enhance the function of the viral vector(s). The viral vector-based compositions prepared by the method of the present invention may be in solid or liquid form and may be, inter alia, in the form of (a) powder(s), (a) tablet(s) or (a) solution(s).

The viral vector-based composition prepared in accordance with the present invention is further characterized in that the particles comprised in the composition have a particle size distribution with a polydispersity index (PDI) of less than 0.5.

The term "particle(s)", as used herein, relates to the viral vector(s) that represent the main, active ingredient of the composition prepared in accordance with the invention. The term "particle size distribution", in accordance with the present invention, refers to the relative amount of particles present according to size. Typically, the relative amount is determined by mass.

In accordance with the present invention, the particle size distribution is expressed in terms of the polydispersity index (PDI). Polydispersity and the polydispersity index are parameters measured by Dynamic Light Scattering (DLS) and characterize a dispersion or solution in addition to the typically determined main parameters, i.e. particle size and hydrodynamic diameter of particles. DLS measures time-dependent fluctuations in the scattering intensity arising from particles, such as e.g. viral particles or proteins undergoing random Brownian motions (diffusion). A monochromatic light beam, such as a laser beam, causes a Doppler shift in a solution with particles in Brownian motion when the light hits the moving particles, thereby changing the wavelength (typically red light at 633 nm or near-infrared at 830 nm) of the incoming light—this change is related to the size of the particles. The particles in a liquid move about randomly and their motion is used to determine the size of the particles: small particles are moving quickly resulting in a more rapid intensity fluctuation, whereas large particles are moving slowly, leading to slower intensity fluctuations.

Construction of the time-dependent autocorrelation function from the measured intensity fluctuation and fitting of this correlation curve to an exponential function gives a description of the particle motion in the medium by calculation of the Diffusion coefficient of the Brownian molecular motion. The hydrodynamic diameter of the particles can subsequently be calculated by using the Stokes-Einstein equation. For polydisperse samples, this curve is a sum of exponential decays. The polydispersity index (PDI) is a parameter derived from the cumulant analysis of the DLS measured intensity autocorrelation function originally introduced by D. E. Koppel in *The Journal of Chemical Physics* 57(11); 1972; pp: 4814-20. In the cumulant analysis, a single exponential fit is applied to the resulting autocorrelation function by the applied DLS software assuming a single-sized population following a Gaussian distribution. The polydispersity index is related to the standard deviation (σ) of the hypothetical Gaussian distribution around the assumed particle size population in the following fashion:

$$PDI = \sigma^2 / Z_D^2,$$

where $Z_D$ is Z-average size or cumulants mean, the intensity weighted mean hydrodynamic size of the ensemble collection of particle, representing the average of several species in the case of polydisperse samples (Stepto, R F T et al. (2009). "Dispersity in Polymer Science" Pure Appl. Chem. 81 (2): 351-353).

Calculated polydispersity indices are dimensionless parameters representing the width of the particle size distribution in the solution. PDI values between 0.1 to 0.2 correspond to a narrow particle size distribution approximately representing a monodisperse particle size distribution. PDI values around 0.3 suggest an increasing width of the particle size distribution containing an increasing number of different particle populations. Values ranging between 0.5 and 0.7 represent a very broad particle size distribution containing very large particles or aggregates. PDI values greater than 0.7 indicate the sample has a very broad particle size distribution and may contain large particles or aggregates. In other words, the lower the PDI value, the more predominant infective viral particles species are present, i.e. viral particles species with a narrow particle size and without or with only a small amount of aggregates and, accordingly, a higher efficacy of the viral vector composition can be achieved.

In accordance with the present invention, the PDI is less than 0.5. As described above, this PDI indicates a particle size distribution ranging from almost monodisperse to moderate polydisperse, with infective particles as the predominant species and only a minor portion of large particles or agglomerates, or even without any large particles or agglomerates. Preferably, the PDI is less than 0.3, more preferably less than 0.2 and most preferably less than 0.1.

In accordance with the present invention and the applied example 5, the preferred PDI value is less than 0.5 for enveloped viruses, e.g. MVA, and less than 0.3 for non-enveloped viruses, e.g. adenoviruses. Furthermore, it is preferred to maintain the above mentioned PDI values during viral vector processing, manufacturing, and distribution phases.

The method of the present invention comprises in a first step (a) the provision of replication-deficient viral vectors.

Replication-deficient viral vectors are viral vectors that are not capable of replicating to generate new viral particles in host cells. For example, the viral vectors can have lost their replication competence by empirical and rational attenuation processes resulting in a loss of important parts of their genome accompanied by (i) retention of their ability to infect several cell types, and (ii) retention of their immunogenicity. Also VLPs fall under the term "replication-deficient viral vector", in accordance with the present invention. Due to the lack of replication competence, replication-deficient viral vectors represent safe and robust mechanism to induce both effector cell mediated and humoral immunity. As a consequence, priming with these vectors can improve the magnitude, quality and durability of such responses, while at the same time providing an increased safety.

Suitable replication-deficient viral vectors for vaccine preparation are well known in the art. For example, Verheust C. et al. (Vaccine 30, 2012) provides a review regarding modified vaccinia Ankara virus (MVA)-based vectors, Rosewell A et al., (J Genet Syndr Gene Ther, 2011) provides a review regarding helper-dependent adenoviral vectors, and Mulder A M et al. (PlosOne 7, 2012) provides a review regarding recombinant VLP-based vaccines. The considerations for choosing a suitable viral vector for vaccine production commonly applied in the art apply mutatis mutandis with regard to choosing a suitable viral vector for vaccine production in accordance with the present invention. Accordingly, viral vectors already available in the art, as well as novel viral vectors, may be employed in the claimed method. Preferably, the replication-deficient viral vectors are selected from the group consisting of MVA, adenovirus, adeno associated virus, lentivirus, Vesicular stomatitis virus, herpes simplex virus, or measles virus. Most preferably, the replication-deficient viral vector is modified vaccinia Ankara virus (MVA) or adenovirus.

The replication-deficient viral vectors can be freshly prepared, e.g. reconstituted after harvesting from cell cultures, or can be provided as a pre-prepared composition, for example from commercial sources.

In a second step (b), the method comprises the provision of a solution comprising at least one sugar and at least three different excipients selected from hydrophilic and amphiphilic excipients, wherein the excipients are characterized by polar, aliphatic, aromatic, negatively charged, and/or positively charged functional groups.

The solution, in accordance with the present invention, can be an aqueous or a non-aqueous solution. In the context of the present invention, the term "aqueous solution" refers on one hand to water but extends on the other hand also to buffered solutions and hydrophilic solvents miscible with water, thus being able to form a uniform phase. Examples for aqueous solutions include, without being limited, water, methanol, ethanol or higher alcohols as well as mixtures thereof. Non-limiting examples for non-aqueous solvents include dimethylsulfoxide (DMSO), ethylbenzene, and other polar solvents.

The term "comprising", as used in accordance with the present invention, denotes that further steps and/or components can be included in addition to the specifically recited steps and/or components. However, this term also encompasses that the claimed subject-matter consists of exactly the recited steps and/or components.

Non-limiting examples of further components that can be comprised in the solution according to step (b) of the method of the invention include e.g., water, amino acids, buffers such as phosphate, citrate, succinate, acetic acid, histidine, glycine, arginine and other organic acids or their salts; antioxidants such as ascorbic acid, methionine, tryptophan, cysteine, glutathione, chelating agents such as ethylenediaminetetraacetic acid (EDTA); counterions such as sodium; and/or nonionic surfactants such as polysorbates, poloxamers, or PEG or other solvents. Preferably, the solution does not contain any proteins other than the (viral) proteins that are part of the viral vectors and the above included components in form of a pharmaceutical carrier.

The solution according to step (b) of the method of the invention further comprises at least one sugar.

The term "sugar", as used herein, refers to any types of sugars, i.e. the monosaccharide, disaccharide or oligosaccharide forms of carbohydrates as well as sugar alcohols. Examples of suitable sugars include, without being limiting, trehalose, saccharose, sucrose, glucose, lactose, mannitol, and sorbitol or sugar derivatives such as aminosugars, e.g. glucosamine or n-acetyl glucosamine.

The term "at least", as used herein, refers to the specifically recited amount or number but also to more than the specifically recited amount or number. For example, the term "at least one" encompasses also at least 2, at least 3, at least 4, at least 5, at least 6, at least 7, at least 8, at least 9, at least 10, such as at least 20, at least 30, at least 40, at least 50 and so on. Furthermore, this term also encompasses exactly 1, exactly 2, exactly 3, exactly 4, exactly 5, exactly 6, exactly 7, exactly 8, exactly 9, exactly 10, exactly 20, exactly 30, exactly 40, exactly 50 and so on.

It will further be appreciated that the term "one sugar" means one type of sugar and does not limit the number of molecules of this particular type of sugar to one. Further, in those cases where more than one sugar is comprised, such as e.g. two sugars, two different types of sugar envisaged. Preferably, the solution comprises exactly one type of sugar, preferably trehalose.

Preferred amounts of sugars to be comprised in the solution according to the invention are between 0.1 mg/ml to 200 mg/ml sugar, more preferably between 10 mg/ml to 180 mg/ml sugar, even more preferably between 20 mg/ml to 160 mg/ml sugar and most preferably the amount is about 80 mg/ml sugar. Where a mixture of different types of sugars is employed, these preferred amounts refer to the sum of all sugars in the solution.

The term "about", as used herein, encompasses the explicitly recited values as well as small deviations therefrom. In other words, an amount of sugar of "about 80 mg/ml" includes, but does not have to be exactly the recited amount of 80 mg/ml but may differ by several mg/ml, thus including for example 92 mg/ml, 84 mg/ml, 88 mg/ml, 76 mg/ml, 72 mg/ml or 68 mg/ml. The skilled person is aware that such values are relative values that do not require a complete accuracy as long as the values approximately correspond to the recited values. Accordingly, a deviation from the recited value of for example 15%, more preferably of 10%, and most preferably of 5% is encompassed by the term "about". These deviations of 15%, more preferably of 10% and most preferably of 5% hold true for all embodiments pertaining to this invention wherein the term "about" is used.

Preferably, the amount of sugar is exactly 80 mg/ml.

In accordance with the present invention, the solution according to step (b) of the method of the invention further comprises at least three different excipients selected from hydrophilic and amphiphilic excipients, wherein the excipients are characterized by polar, aliphatic, aromatic, negatively charged, and/or positively charged functional groups.

Excipients are well known in the art. Excipients are defined as ingredients that are included in a composition, such as e.g. pharmaceutical compositions, together with the active agent. They are typically added to formulations for several reasons and, thus, some excipients may have more than one effect or purpose for being part of the formulation. One of their main functions is that of a stabilizer. The main function of such stabilizers in pharmaceutical formulations is to protect the biologically active agent against the different types of stresses that are applied to said biologically active agent, such as e.g. a protein or a viral vector, during isolation, purification, drying e.g. by lyophilization, spray-drying, spray-freeze drying or foam-drying, storage either in solution or after drying as well as reconstitution after drying. There are specific mechanisms of stabilization of biologically active agents, which are specifically related to the excipients in the formulation. Stabilization is for example achieved by strengthening of the stabilizing forces, by destabilization of the denatured state, or by direct binding of excipients to the biologically active agents. Frequently employed excipients for use as stabilizers of biologically active agents include, without being limiting, sugars, polyols, amino acids, amines, salts, polymers and surfactants, each of which may exert different stabilizing effects.

Non-limiting examples of excipients selected from hydrophilic and amphiphilic excipients, wherein said excipients are further characterized by having polar, aliphatic, aromatic, negatively charged, and/or positively charged functional groups, classified according to international pharmacopoeias as save excipients for use in viral vector based compositions are represented in Table 1 below.

TABLE 1

Excipients classified according to international pharmacopoeias as save excipients for use in viral vector based compositions .ALPHA.-TOCOPHEROL
.ALPHA.-TOCOPHEROL, DL-
1,2-DIMYRISTOYL-SN-GLYCERO-3-(PHOSPHO-S-(1-GLYCEROL))
1,2-DIMYRISTOYL-SN-GLYCERO-3-PHOSPHOCHOLINE
1,2-DISTEAROYL-SN-GLYCERO-3-(PHOSPHO-RAC-(1-GLYCEROL))
1,2-DISTEAROYL-SN-GLYCERO-3-PHOSPHOCHOLINE
ACETIC ACID
ACETIC ACID, GLACIAL
ACETIC ANHYDRIDE
ACETONE SODIUM BISULFITE
ACETYLATED MONOGLYCERIDES
ACETYLTRYPTOPHAN, DL-
ACTIVATED CHARCOAL
ADIPIC ACID
ALANINE
ALBUMIN AGGREGATED
ALBUMIN COLLOIDAL
ALBUMIN HUMAN
ALCOHOL
ALCOHOL, DEHYDRATED
ALCOHOL, DENATURED
ALCOHOL, DILUTED
AMMONIUM ACETATE
AMMONIUM HYDROXIDE
AMMONIUM SULFATE
ANHYDROUS CITRIC ACID
ANHYDROUS DEXTROSE
ANHYDROUS LACTOSE
ANHYDROUS TRISODIUM CITRATE
ARGININE
ASCORBIC ACID
ASPARTIC ACID
BENZALKONIUM CHLORIDE
BENZENESULFONIC ACID
BENZETHONIUM CHLORIDE
BENZOIC ACID
BENZYL ALCOHOL
BENZYL BENZOATE
BENZYL CHLORIDE
BIBAPCITIDE
BORIC ACID
BROCRINAT
BUTYLATED HYDROXYANISOLE
BUTYLATED HYDROXYTOLUENE
BUTYLPARABEN
CALCIUM
CALCIUM CHLORIDE
CALCIUM GLUCEPTATE
CALCIUM HYDROXIDE
CALCOBUTROL
CALDIAMIDE SODIUM
CALOXETATE TRISODIUM
CALTERIDOL CALCIUM
CAPTISOL
CARBON DIOXIDE
CARBOXYMETHYLCELLULOSE
CARBOXYMETHYLCELLULOSE SODIUM, UNSPECIFIED FORM
CASTOR OIL
CELLULOSE, MICROCRYSTALLINE
CHLOROBUTANOL
CHLOROBUTANOL HEMIHYDRATE
CHLOROBUTANOL, ANHYDROUS
CHOLESTEROL
CITRATE
CITRIC ACID
CITRIC ACID MONOHYDRATE
CITRIC ACID, HYDROUS
CORN OIL
COTTONSEED OIL
CREATINE
CREATININE
CRESOL TABLE 1-continued Excipients classified according to international pharmacopoeias as save excipients for use in viral vector based compositions CROSCARMELLOSE SODIUM
CROSPOVIDONE
CYSTEINE
CYSTEINE HYDROCHLORIDE
DALFAMPRIDINE
DEOXYCHOLIC ACID
DEXTRAN
DEXTRAN 40
DEXTROSE
DEXTROSE MONOHYDRATE
DEXTROSE SOLUTION
DIATRIZOIC ACID
DIETHANOLAMINE
DIMETHICONE MEDICAL FLUID 360
DIMETHYL SULFOXIDE
DIPALMITOYLPHOSPHATIDYLGLYCEROL, DL-
DISODIUM HYDROGEN CITRATE
DISODIUM SULFOSALICYLATE
DISOFENIN
DISTEAROYLPHOSPHATIDYLCHOLINE, DL-
DOCUSATE SODIUM
EDETATE CALCIUM DISODIUM
EDETATE DISODIUM
EDETATE DISODIUM ANHYDROUS
EDETATE SODIUM
EGG PHOSPHOLIPIDS
ETHANOLAMINE HYDROCHLORIDE
ETHYL ACETATE
ETHYLENEDIAMINE
ETHYLENE-VINYL ACETATE COPOLYMERS
EXAMETAZIME
FERRIC CHLORIDE
FRUCTOSE
GADOLINIUM OXIDE
GAMMA CYCLODEXTRIN
GELATIN
GENTISIC ACID
GENTISIC ACID ETHANOLAMIDE
GENTISIC ACID ETHANOLAMINE
GLUCEPTATE SODIUM
GLUCEPTATE SODIUM DIHYDRATE
GLUCONOLACTONE
GLUCURONIC ACID
GLUTATHIONE
GLYCERIN
GLYCINE
GLYCINE HYDROCHLORIDE
GUANIDINE HYDROCHLORIDE
HETASTARCH
HEXYLRESORCINOL
HISTIDINE
HUMAN ALBUMIN MICROSPHERES
HYALURONATE SODIUM
HYDROCHLORIC ACID
HYDROCHLORIC ACID, DILUTED
HYDROXYETHYLPIPERAZINE ETHANE SULFONIC ACID
HYDROXYPROPYL.BETA.-CYCLODEXTRIN
IODINE
IODOXAMIC ACID
IOFETAMINE HYDROCHLORIDE
ISOLEUCINE
ISOPROPYL ALCOHOL
ISOTONIC SODIUM CHLORIDE SOLUTION
LACTIC ACID, DL-
LACTIC ACID, L-
LACTIC ACID, UNSPECIFIED FORM
LACTOBIONIC ACID
LACTOSE MONOHYDRATE
LACTOSE, HYDROUS
LACTOSE, UNSPECIFIED FORM
LECITHIN
LECITHIN, EGG
LECITHIN, HYDROGENATED SOY
LEUCINE
LIDOFENIN
LYSINE
LYSINE ACETATE TABLE 1-continued Excipients classified according to international pharmacopoeias
as save excipients for use in viral vector based compositions MAGNESIUM CHLORIDE
MAGNESIUM STEARATE
MALEIC ACID
MANNITOL
MEBROFENIN
MEDRONATE DISODIUM
MEDRONIC ACID
MEGLUMINE
METACRESOL
METAPHOSPHORIC ACID
METHANESULFONIC ACID
METHIONINE
METHYL PYRROLIDONE
METHYLBORONIC ACID
METHYLCELLULOSES
METHYLENE BLUE
METHYLPARABEN
MIRIPIRIUM CHLORIDE
MONOTHIOGLYCEROL
N-(CARBAMOYL-METHOXY PEG-40)-1,2-DISTEAROYL-CEPHALIN SODIUM
N,N-DIMETHYLACETAMIDE
NIACINAMIDE
NIOXIME
NITRIC ACID
NITROGEN
OCTANOIC ACID
OXIDRONATE DISODIUM
OXYQUINOLINE
PALMITIC ACID
PEANUT OIL
PEG VEGETABLE OIL
PEG-20 SORBITAN ISOSTEARATE
PEG-40 CASTOR OIL
PEG-60 CASTOR OIL
PEG-60 HYDROGENATED CASTOR OIL
PENTASODIUM PENTETATE
PENTETATE CALCIUM TRISODIUM
PENTETIC ACID
PERFLUTREN
PHENOL
PHENOL, LIQUEFIED
PHENYLALANINE
PHENYLETHYL ALCOHOL
PHENYLMERCURIC NITRATE
PHOSPHATIDYL GLYCEROL, EGG
PHOSPHOLIPID
PHOSPHOLIPID, EGG
PHOSPHORIC ACID
POLOXAMER 188
POLYETHYLENE GLYCOL 200
POLYETHYLENE GLYCOL 300
POLYETHYLENE GLYCOL 3350
POLYETHYLENE GLYCOL 400
POLYETHYLENE GLYCOL 4000
POLYETHYLENE GLYCOL 600
POLYGLACTIN
POLYLACTIDE
POLYOXYETHYLENE FATTY ACID ESTERS
POLYOXYL 35 CASTOR OIL
POLYPROPYLENE GLYCOL
POLYSILOXANE
POLYSORBATE 20
POLYSORBATE 40
POLYSORBATE 80
POLYVINYL ALCOHOL
POTASSIUM BISULFITE
POTASSIUM CHLORIDE
POTASSIUM HYDROXIDE
POTASSIUM METABISULFITE
POTASSIUM PHOSPHATE, DIBASIC
POTASSIUM PHOSPHATE, MONOBASIC
POVIDONE K12
POVIDONE K17
POVIDONES
PROLINE
PROPYL GALLATE
PROPYLENE GLYCOL
PROPYLPARABEN
PROTAMINE SULFATE
SACCHARIN SODIUM
SACCHARIN SODIUM ANHYDROUS
SALT
SERINE
SESAME OIL
SILICONE
SIMETHICONE
SODIUM ACETATE
SODIUM ACETATE ANHYDROUS
SODIUM ASCORBATE
SODIUM BENZOATE
SODIUM BICARBONATE
SODIUM BISULFATE
SODIUM BISULFITE
SODIUM CARBONATE
SODIUM CARBONATE DECAHYDRATE
SODIUM CARBONATE MONOHYDRATE
SODIUM CHLORATE
SODIUM CHLORIDE
SODIUM CHLORIDE INJECTION
SODIUM CHLORIDE INJECTION, BACTERIOSTATIC
SODIUM CHOLESTERYL SULFATE
SODIUM CITRATE
SODIUM DESOXYCHOLATE
SODIUM DITHIONITE
SODIUM FORMALDEHYDE SULFOXYLATE
SODIUM GLUCONATE
SODIUM HYDROXIDE
SODIUM HYPOCHLORITE
SODIUM IODIDE
SODIUM LACTATE
SODIUM LACTATE, L-
SODIUM METABISULFITE
SODIUM OLEATE
SODIUM PHOSPHATE
SODIUM PHOSPHATE DIHYDRATE
SODIUM PHOSPHATE, DIBASIC
SODIUM PHOSPHATE, DIBASIC, ANHYDROUS
SODIUM PHOSPHATE, DIBASIC, DIHYDRATE
SODIUM PHOSPHATE, DIBASIC, DODECAHYDRATE
SODIUM PHOSPHATE, DIBASIC, HEPTAHYDRATE
SODIUM PHOSPHATE, MONOBASIC
SODIUM PHOSPHATE, MONOBASIC, ANHYDROUS
SODIUM PHOSPHATE, MONOBASIC, DIHYDRATE
SODIUM PHOSPHATE, MONOBASIC, MONOHYDRATE
SODIUM PHOSPHITE
SODIUM PYROPHOSPHATE
SODIUM SUCCINATE HEXAHYDRATE
SODIUM SULFATE
SODIUM SULFATE ANHYDROUS
SODIUM SULFITE
SODIUM TARTRATE
SODIUM THIOGLYCOLATE
SODIUM THIOMALATE
SODIUM THIOSULFATE
SODIUM THIOSULFATE ANHYDROUS
SODIUM TRIMETAPHOSPHATE
SORBITAN MONOPALMITATE
SORBITOL
SORBITOL SOLUTION
SOYBEAN OIL
STANNOUS CHLORIDE
STANNOUS CHLORIDE ANHYDROUS
STANNOUS FLUORIDE
STANNOUS TARTRATE
STARCH
STEARIC ACID
STERILE WATER FOR INHALATION
STERILE WATER FOR INJECTION
SUCCIMER
SUCCINIC ACID
SUCROSE
SULFOBUTYLETHER.BETA.-CYCLODEXTRIN
SULFUR DIOXIDE

TABLE 1-continued

Excipients classified according to international pharmacopoeias as save excipients for use in viral vector based compositions SULFURIC ACID
SULFUROUS ACID
TARTARIC ACID
TARTARIC ACID, DL-
TERT-BUTYL ALCOHOL
TETRAKIS(2-METHOXYISOBUTYLISOCYANIDE)COPPER(I) TETRAFLUOROBORATE
TETROFOSMIN
THEOPHYLLINE
THIMEROSAL
THREONINE
TIN
TRIFLUOROACETIC ACID
TRISODIUM CITRATE DIHYDRATE
TROMANTADINE
TROMETHAMINE
TRYPTOPHAN
TYROSINE
UREA
URETHANE
VALINE
VERSETAMIDE
YELLOW WAX
ZINC
ZINC ACETATE
ZINC CARBONATE
ZINC CHLORIDE
ZINC OXIDE Preferred amounts of the sum of excipients to be comprised in the solution according to the invention are between 0.001 and 100 mg/ml, preferably between 1 and 80 mg/ml, more preferably between 5 and 60 mg/ml, even more preferably between 10 and 30 mg/ml and most preferably the amount is about 20 mg/ml.

Preferably, the solution comprises trehalose or sucrose as the sugar and mannitol as the sugar alcohol and amino acids as the at least three excipients. Even more preferably, the solution comprises trehalose as the sugar and at least three different amino acids as the at least three excipients.

Furthermore, the solution is characterized by an excipient to sugar ratio of at least 1:2. More preferably, the solution is characterized by an excipient to sugar ratio of at least 1:1.5 (w/w), such as e.g. at least 1:1(w/w) and most preferably of at least 1:0.1(w/w).

Preferably, the pH value of the resulting composition according to step (b) will be adjusted to pH values between 4.0 and 9.0 before mixing with the replication deficient viral vectors of step (a). The pH value chosen depends on the requirements for the particular viral vector, determined by biologic characteristics such as e.g. size, enveloped (lipid membrane) or not enveloped etc.

In a third step (c), the method of the present invention comprises the step of mixing the replication deficient viral vectors of step (a) with the solution of step (b).

The term "mixing", as used herein, is not particularly limited and includes all means of mixing viral vectors with a solution according to (b). For example, the components of step (a) and (b) can simply be transferred into the same vessel, where they can mix by diffusion; they can additionally be stirred, e.g. by swirling the vessel around or by stirring with a suitable tool. Stirring can be for a limited amount of time, such as e.g. once or twice, or can be continuously.

Preferably, the components of step (a) and (b) can mixed together by re-buffering of the composition of the recited step (a) in the composition of the recited step (b) using chromatographic operations as well as dialysis, ultrafiltration and diafiltration operations.

The order of steps (a) and (b) is not particularly limited, i.e. step (a) can be carried out first, followed by step (b), or vice versa. Moreover, steps (a) and (b) can be carried out concomitantly. Step (c) is then carried out after steps (a) and (b) have been carried out.

In one embodiment, the method of the present invention consists of the recited steps (a) to (c). However, it will be appreciated that where the method of the invention comprises (rather than consists of) the cited steps (a) to (c), further method steps may be included in the method. For example, additional washing and/or drying steps may be included. Preferably, the method of the invention consists of the cited steps (a) to (c), optionally in combination with the below described additional method steps (d) and (e), and optionally in combination with additional washing steps. Even more preferably, the method of the present invention consists of the recited steps (a) to (c), in combination with the below described additional method steps (d) drying and (e) reconstitution of the resulting dried composition.

In accordance with the present invention, a method is provided for the preparation of improved viral vector-based vaccines and gene transfer therapeutics. By preparing vector-based compositions using the method of the present invention, unappreciated polydispersity can be avoided, thus resulting in a more suitable ratio between vector particle distribution and functional efficacy. Moreover, as discussed herein above, low polydispersity is associated with lower viscosity and not only provides better infectivity, but also leads to better syringeability and injectability.

As shown in the appended Example 1, it was surprisingly observed that mixing adenoviral vectors by diluting a highly concentrated adenoviral stock solution with a solution comprising at least one sugar and at least three different excipients according to the invention, wherein the solution is further characterized by an excipient to sugar ratio of at least 1:2 (w/w) resulted in the complete retention of the hydrodynamic radii of the contained adenoviral particles monitored by Dynamic Light Scattering (DLS) analysis compared to the similar dilutions in the original supplier formulation and in the commonly used phosphate-buffered saline (PBS).

Evaluation of the obtained correlation functions recorded in the respective DLS experiments for the adenoviral vector formulations before freeze drying suggested that already mixing of the adenoviral vectors in the solutions according to the invention, particularly composition 1 and composition 2 led to a retention of the corresponding analyzed hydrodynamic radius of about 70 nm compared to the untreated stock solution (Example 1; FIG. 1A to C). In contrast, similar mixing of the adenoviral stock solution with PBS or with the original supplier formulation during the preparation process of the samples before freeze drying led to a remarkable increase in the measured hydrodynamic radius of the adenoviral vectors compared to the untreated adenoviral vector (Example 1; FIG. 1A and FIG. 2).

In a preferred embodiment of the method of the invention, the at least three different excipients comprise amino acids. In an even more preferred embodiment of the method of the invention, the at least three different excipients are at least three different amino acids.

The term "amino acid", as used herein, is well known in the art. Amino acids are the essential building blocks of proteins. In accordance with the present invention, the term "amino acid" refers to free amino acids which are not bound to each other to form oligo- or polymers such as dipeptides, tripeptides, oligopeptides or proteins (also referred to herein as polypeptides). The term "amino acid" includes naturally occurring amino acids, but also other amino acids such as artificial amino acids. They can be classified into the characteristic groups of excipients with non-polar, aliphatic; polar, uncharged; positively and/or negatively charged and/ or aromatic R groups (Nelson D. L. & Cox M. M., "Lehninger Biochemie" (2005), pp. 122-127). The amino acids comprised in the solution (b) of the present invention can be selected from naturally occurring amino acids as well as artificial amino acids or derivatives of these naturally occurring or artificial amino acids.

Naturally occurring amino acids include the 20 amino acids that make up proteins (i.e. the so-called proteinogenic amino acids), i.e. glycine, proline, arginine, alanine, asparagine, aspartic acid, glutamic acid, glutamine, cysteine, phenylalanine, lysine, leucine, isoleucine, histidine, methionine, serine, valine, tyrosine, threonine and tryptophan. Other naturally occurring amino acids are e.g. carnitine, creatine, creatinine, guanidinoacetic acid, ornithine, hydroxyproline, homocysteine, citrulline, hydroxylysine or beta-alanine. Artificial amino acids are amino acids that have a different side chain length and/or side chain structure and/or have the amine group at a site different from the alpha-C-atom. Derivates of amino acids include, without being limiting, n-acetyl-tryptophan, phosphonoserine, phosphonothreonine, phosphonotyrosine, melanin, argininosuccinic acid and salts thereof and DOPA. In connection with the present invention, all these terms also include the salts of the respective amino acids.

In an embodiment of the method of the invention, the at least three different excipients comprise "at least one dipeptide and/or tripeptide". Where more than one di- or tripeptide is comprised in the solution, a mixture of dipeptides and tripeptides is explicitly envisaged herein. The number of di- and tripeptides can be selected independently of each other, e.g. the solution may comprise two dipeptides and three tripeptides. It will be readily understood by the skilled person that when referring to a certain number of di- and tripeptides herein, said number is intended to limit the amount of different types of di- and tripeptides, but not the number of molecules of one type of dipeptide or tripeptide. Thus, for example the term "four dipeptides or tripeptides", refers to four different types of dipeptides and/or tripeptides, wherein the amount of each individual di- and/or tripeptide is not particularly limited. Preferably, the number of (different) di- or tripeptides does not exceed nine di- or tripeptides.

The term "dipeptide or tripeptide", as used herein, relates to peptides consisting of two or three amino acids, respectively. Exemplary dipeptides are glycylglutamine (Gly-Gln), glycyltyrosine (Gly-Tyr), alanylglutamine (Ala-Gln) and glycylglycine (Gly-Gly). Further non-limiting examples of naturally occurring dipeptides are carnosine (beta-alanyl-L-histidine), N-acetyl-carnosine (N-acetyl-(beta-alanyl-L-histidine), anserine (beta-alanyl-N-methyl histidine), homoanserine (N-(4-aminobutyryl)-L-histidine), kyotorphin (L-tyrosyl-L-arginine), balenine (or ophidine) (beta-alanyl-N tau-methyl histidine), glorin (N-propionyl-γ-L-glutamyl-L-ornithine-δ-lac ethyl ester) and barettin (cyclo-[(6-bromo-8-en-tryptophan)-arginine]). Examples of artificial dipeptides include, without being limiting, aspartame (N-L-a-aspartyl-L-phenylalanine 1-methyl ester) and pseudoproline.

Exemplary tripeptides are glutathione (γ-glutamyl-cysteinyl-glycine) and its analogues ophthalmic acid (L-γ-glutamyl-L-α-aminobutyryl-glycine) as well as norophthalmic acid (γ-glutamyl-alanyl-glycine). Further non-limiting examples of tripeptides include isoleucine-proline-proline (IPP), glypromate (Gly-Pro-Glu), thyrotropin-releasing hormone (TRH, thyroliberin or protirelin: L-pyroglutamyl-L-histidinyl-L-prolinamide), melanostatin (prolyl-leucyl-glycinamide), leupeptin (N-acetyl-L-leucyl-L-leucyl-L-argininal) and eisenin (pGlu-Gln-Ala-OH).

It is also envisaged herein that the solution of (b) comprises at least three excipients including (an) amino acid(s) as well as at least one di- and/or tripeptide.

Preferably, the total amount of all amino acids, dipeptides and/or tripeptides (that is the sum of all of these components in the solution) to be employed is between 0.001 and 100 mg/ml, preferably between 1 and 80 mg/ml, more preferably between 5 and 60 mg/ml, even more preferably between 10 and 30 mg/ml and most preferably the amount is about 20 mg/ml.

It is preferred that the amino acids, and/or the di- and/or tripeptides, when used in connection with medical applications, do not exert any pharmacological properties.

In another preferred embodiment of the method of the invention, the viral vector-based composition is prepared for storage as a liquid. In another preferred embodiment of the method of the invention, the viral vector-based composition is prepared for storage as a dried preparation. Such viral vector-based composition (in liquid or dried preparations) may be subsequently used for the preparation of vaccines or gene transfer therapeutics.

In a further preferred embodiment of the method of the invention, which embodiment comprises a further step (d) of drying the composition obtained in step (c), the composition is dried by freeze-drying, spray-drying, spray freeze drying, or supercritical drying.

The term "drying", as used herein, refers to the reduction or removal of the liquid content present in the composition. The liquid content is considered to have been reduced if the liquid is reduced to less than 20%, such as for example less than 10%, such as for example less than 8%, more preferably less than 7%, such as less than 5% or less than 1%. Even more preferably, the liquid is reduced to 0.5% or less.

Suitable methods for drying include, without being limiting, lyophilisation (freeze drying), spray drying, freeze-spray drying, convection drying, conduction drying, gas stream drying, drum drying, vacuum drying, dielectric drying (by e.g. radiofrequency or microwaves), surface drying, air drying or foam drying.

Freeze-drying, also referred to as lyophilisation, is also well known in the art and includes the steps of freezing the sample and subsequently reducing the surrounding pressure while adding sufficient heat to allow the frozen water in the material to sublime directly from the solid phase to the gas phase followed by a secondary drying phase. Preferably, the lyophilised preparation is then sealed to prevent the re-absorption of moisture.

Spray-drying is also well known in the art and is a method to convert a solution, suspension or emulsion into a solid powder in one single process step. Generally, a concentrate of the liquid product is pumped to an atomising device, where it is broken into small droplets. These droplets are exposed to a stream of hot air and lose their moisture very rapidly while still suspended in the drying air. The dry powder is separated from the moist air in cyclones by centrifugal action, i.e. the dense powder particles are forced toward the cyclone walls while the lighter, moist air is directed away through the exhaust pipes.

Spray-drying is often the method of choice, as it avoids the freezing step and requires lower energy costs as compared to lyophilisation. Spray-drying has also been shown to be a particularly advantageous drying procedure that is suitable for biomolecules, due to the short contact time with high temperature and its special process control. Thus, because spray-drying results in a dispersible dry powder in just one step it is often favoured to freeze drying when it comes to drying techniques for biomolecules.

Spray-freeze-drying is also well known in the art and is a method that combines processing steps common to freeze-drying and spray-drying. The sample provided is nebulised into a cryogenic medium (such as e.g. liquid nitrogen), which generates a dispersion of shock-frozen droplets. This dispersion is then dried in a freeze dryer.

Supercritical drying is another technique well known in the art. This method relies on high-temperature and high-pressure above the critical temperature ($T_c$) and critical pressure ($p_c$) to change a liquid into a gas wherein no phase boundaries are crossed but the liquid to gas transition instead passes through the supercritical region, where the distinction between gas and liquid ceases to apply. The densities of the liquid phase and vapour phase become equal at the critical point of drying.

Preferably, the step (d) of drying the composition obtained in (c) is by lyophilisation.

Figure 3:
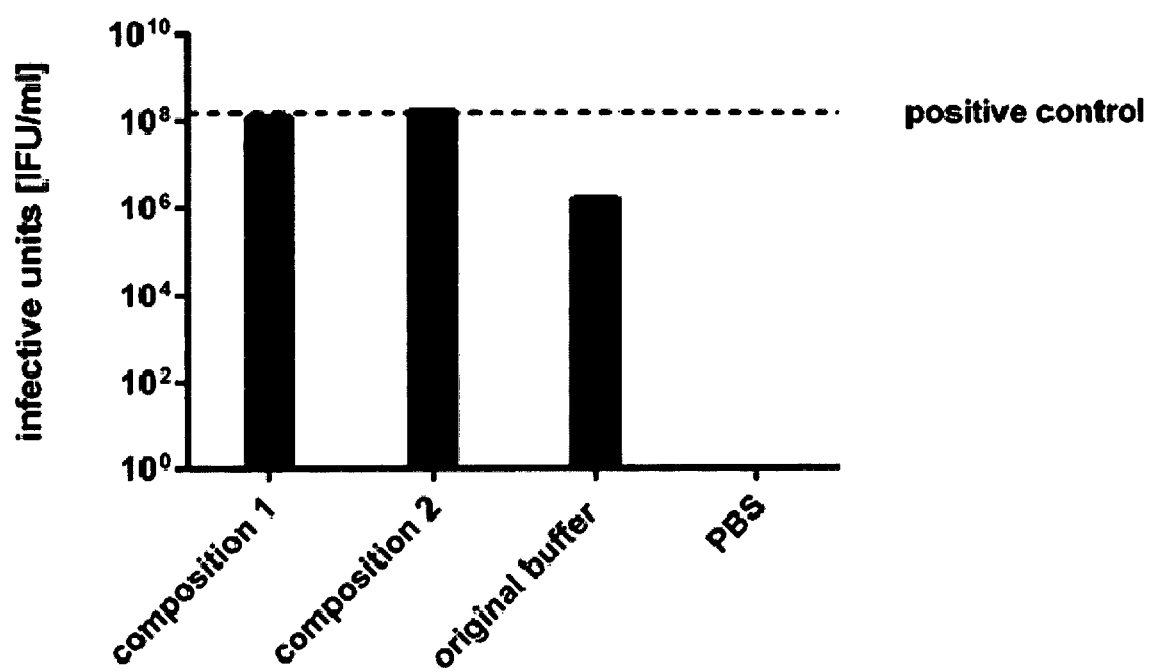

As further shown in Example 1 below, it was surprisingly found that combining the adenoviral vectors by the method of the invention with the recited at least three excipients and sugar at a ratio of at least 1:2 provides superior stability for the dried adenoviral vector formulations. In Example 1, the combination of adenoviral vector preparation with the compositions, particularly composition 1 and 2 according to the present invention already during early phase downscaling steps and subsequent freeze drying resulted in the complete retention of the infective titer (Example 1; FIG. 3) and the hydrodynamic radii of the viral particles (Example 1; FIGS. 4A and B). In contrast, freeze drying of the corresponding adenoviral vector preparations in the original supplier formulation resulted in significant loss of infectivity (Example 1; FIG. 3) and in increased particle size Example 1; FIG. 4C). The similar sample preparation procedure in combination with the common phosphate-buffered saline (PBS) resulted in complete loss of infectivity (Example 1; FIG. 3) and in massive increase in particle size (Example 1 FIG. 4D) and the formation of significant amounts of higher order aggregates, already after freeze drying. Most importantly, such dried formulations of biopharmaceutical drug substances or drug products are suitable for a variety of further handling steps, such as aliquoting, distribution, shipment, storage etc.

In accordance with this preferred embodiment of the method of the present invention, a dry composition is obtained. It is particularly preferred that the composition is a powder composition. In the case of freeze drying or spray-freeze drying, the resulting dried composition is automatically obtained in the form of a powder. In those cases where the dry composition is not obtained as a powder, but instead in the form of e.g. a dried cake, the skilled person is aware of how to further modify the composition in order to obtain a powder.

Such an additional drying step can be advantageous, as intermolecular interactions in a composition can lead e.g. to modified electrostatic interactions of viral vectors resulting in a loss of particle integrity and function. The reduced water content within the composition in accordance with this preferred embodiment reduces the molecular mobility within the product, and thus helps to maintain particle integrity and function.

In another preferred embodiment of the method of the invention, the method further comprises the step of subsequently storing the viral vector-based composition at a temperature selected from about −90° C. to about 50° C. More preferably, the viral vector-based composition is subsequently stored at a temperature range selected from the group consisting of about −90° C. to about −70° C., about −30° C. to about −10° C., about 1° C. to about 10° C., about 15° C. to about 25° C. and about 30° C. to about 50° C. Even more preferably, the viral vector-based composition is subsequently stored at a temperature range selected from the group consisting of about −85° C. to about −75° C., about −25° C., to about −15° C., about 2° C. to about 8° C. and about 20° C. to about 45° C. Most preferably, the viral vector-based composition is subsequently stored at a temperature selected from about −80° C., about −20° C., room temperature, about 4° C., about 25° C. and about 40° C.

Figure 5:
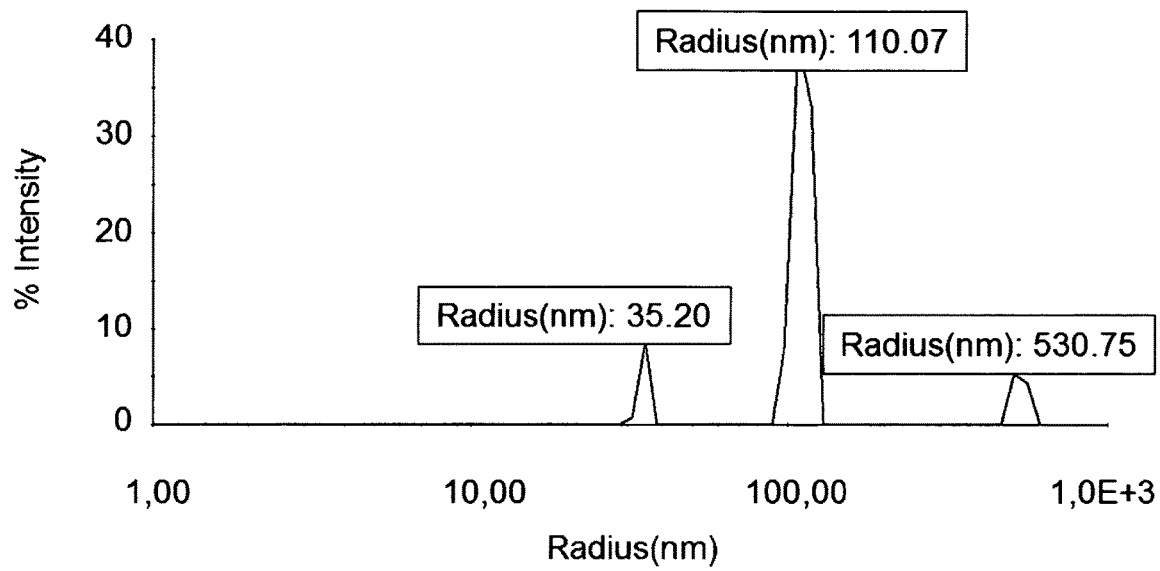
Figure 5:
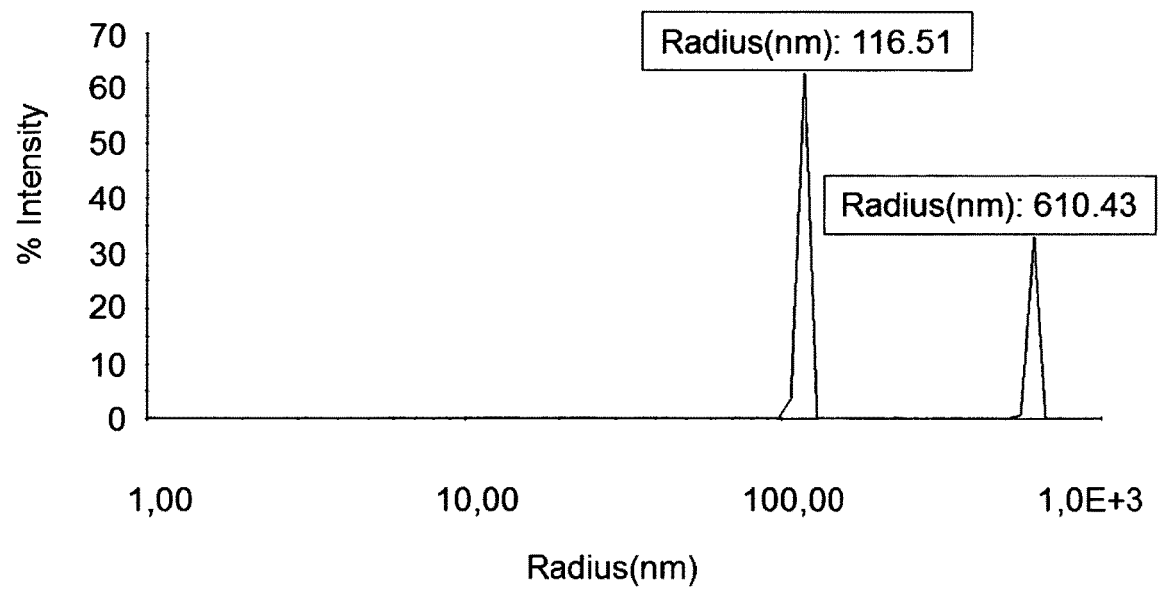

As additionally shown in Example 1 below, it was surprisingly observed, that the differences between the in vitro infectivities of the adenoviral vectors freeze-dried in the compositions according to the invention (composition 1 and 2) and the original supplier formulation and PBS, respectively already observed directly after freeze drying were even more striking after storage of the freeze-dried preparations at elevated temperatures. A complete loss of function of the viral vectors freeze-dried in the original supplier formulation was observed, similar to the results obtained in PBS (Example 1; FIGS. 5A and B). In contrast, even after storage at 25° C. or even at 40° C., the freeze-dried adenoviral vector compositions that were formulated in the stabilizing compositions 1 and 2 early during the production process retained almost the same viral activity as the positive control, i.e. the adenoviral vector prior to being freeze-dried (depicted as dashed line in the diagram of FIG. 5.

Figure 6:
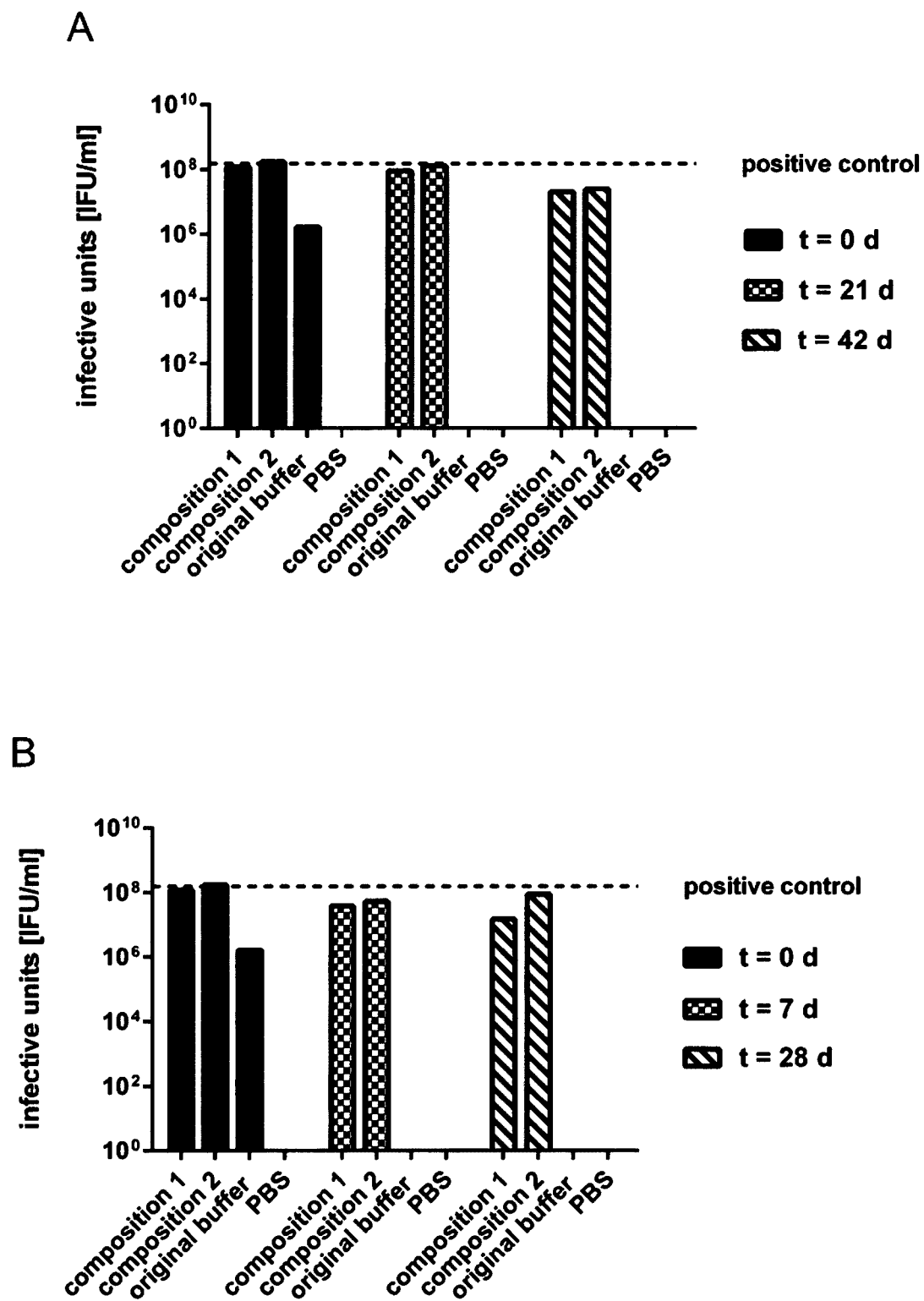

These results of the in vitro infectivity experiments correspond well with the DLS experiments performed in parallel. As examples, the evaluation of the recorded DLS correlation function after storage of the dried adenoviral vector compositions either in the composition 1 and 2 according to the invention or in the original supplier formulation and PBS, respectively after storage for 14 days at 40° C. were depicted in FIG. 6. The storage of the dried adenoviral vector preparations in stabilizing composition 1 and 2 led to retention of the determined hydrodynamic radii of the adenoviral particles (Example 1; FIGS. 6A and B) in contrast to the stored adenoviral particles in the original supplier formulation and in PBS (Example 1; FIGS. 7A and 7B).

In a further preferred embodiment of the method of the invention, the method further comprises a step (e) of reconstituting the composition obtained after drying.

Reconstituting of the composition can be carried out by any means known in the art, such as e.g. dissolving the dried composition in a suitable solution. Non-limiting examples of suitable solutions include the solution of step (b) used for mixing with the viral vector as well as any other solution known to be suitable for viral vector-based compositions, such as e.g. water for injection, buffered solutions, solutions comprising amino acids, sugars, buffers, surfactants or mixtures thereof.

In a further preferred embodiment of the method of the invention, the viral vector is selected from the group consisting of MVA, adenovirus, Adenovirus-associated virus (AAV), lentivirus, vesicular stomatitis virus (VSV), or herpesviruses.

The Modified Vaccinia Ankara (MVA) virus is a highly attenuated strain of vaccinia virus that was developed towards the end of the campaign for the eradication of smallpox in the seventies of the previous century. MVA was derived from Vaccinia strain Ankara by over 570 passages in chicken embryo fibroblast cells (CEF). This resulted in six major deletions corresponding to the loss of about 10% of the vaccinia genome. The complete genomic sequence is known and has a length of 178 kp corresponding to 177 genes. The numerous mutations explain the attenuated phenotype of MVA and its inability to replicate in mammalian cells. MVA is widely considered as the Vaccinia virus strain of choice for clinical investigation because of its high safety profile. MVA has been administered to numerous animal species including monkeys, mice, swine, sheep, cattle, horses, and elephants, with no local or systemic adverse effects. Over 120,000 humans have been safely and successfully vaccinated against smallpox with MVA by intradermal, subcutaneous, or intramuscular injections. Studies in mice and nonhuman primates have further demonstrated the safety of MVA under conditions of immune suppression. Compared to replicating vaccinia viruses, MVA provides similar or higher levels of recombinant gene expression even in non-permissive cells. In animal models, recombinant MVA vaccines have been found immunogenic and to protect against various infectious agents including influenza, parainfluenza, measles virus, flaviviruses, and plasmodium parasites. The combination of a very good safety profile and the ability to deliver antigens in a highly immunogenic way makes MVA suitable as a vaccine vector.

Adenoviruses are medium-sized (90-100 nm), nonenveloped (naked) icosahedral viruses composed of a nucleocapsid and a double-stranded linear DNA genome. There are over 51 different serotypes in humans, which are responsible for 5-10% of upper respiratory infections in children, and many infections in adults as well. When these viruses infect a host cell, they introduce their DNA molecule into the host. The genetic material of the adenoviruses is not incorporated (transient) into the host cell's genetic material. The DNA molecule is left free in the nucleus of the host cell, and the instructions in this extra DNA molecule are transcribed just like any other gene. The only difference is that these extra genes are not replicated when the cell is about to undergo cell division so the descendants of that cell will not have the extra gene. As a result, treatment with the adenovirus will require re-administration in a growing cell population although the absence of integration into the host cell's genome should prevent the type of cancer seen in the SCID trials. This vector system has shown real promise in treating cancer and indeed the first gene therapy product (Gendicine) to be licensed is an adenovirus to treat cancer.

Viruses of the family adenoviridae infect various species of animals, including humans. Adenoviruses represent the largest non-enveloped viruses because they are the maximum size able to be transported through the endosome (i.e. envelope fusion is not necessary). The virion also has a unique "spike" or fiber associated with each penton base of the capsid that aids in attachment to the host cell via the coxsackie-adenovirus receptor on the surface of the host cell.

Adeno-associated virus (AAV) is a small virus that infects humans and some other primate species. AAV is not currently known to cause disease and, consequently, the virus causes a very mild immune response. AAV can infect both dividing and non-dividing cells and can incorporate its genome into that of the host cell. Moreover, episomal AAV elicits long and stable expression and, thus, AAV is suitable for creating viral vectors for gene therapy. Because of its potential use as a gene therapy vector, AAV has previously been modified (self-complementary adeno-associated virus; scAAV). Whereas AAV packages a single strand of DNA and requires the process of second-strand synthesis, scAAV packages both strands which anneal together to form double stranded DNA. This approach allows for rapid expression in the target cell.

Lentiviruses, a subclass of retroviruses have recently been adapted as viral vectors for gene delivery because of their unique ability to integrate into the genome of non-dividing cells. The viral genome in the form of RNA is reverse-transcribed when the virus enters the cell to produce DNA, which is then inserted into the genome by the viral integrase enzyme. The vector, now called a provirus, remains in the genome and is passed on to the progeny of the cell when it divides.

Vesicular stomatitis Indiana virus (VSIV) (often still referred to as VSV) is a virus in the family Rhabdoviridae; the well-known rabies virus belongs to the same family. VSIV can infect insects, cattle, horses and pigs. It has particular importance to farmers in certain regions of the world where it can infect cattle and lead to diseases similar to the foot and mouth disease virus.

Herpes viruses belong to the Herpesviridae, a large family of DNA viruses that cause diseases in animals and humans. Herpes simplex viruses (HSV) HSV-1 and HSV-2 (orolabial herpes and genital herpes), Varicella zoster virus (VZV; chicken-pox and shingles), Epstein-Barr virus (EBV; mononucleosis), and Cytomegalovirus (CMV) are widespread among humans. More than 90% of adults have been infected with at least one of these, and a latent form of the virus remains in most people. Herpes viruses are currently used as gene transfer vectors due to their high transgenic capacity of the virus particle allowing to carry long sequences of foreign DNA, the genetic complexity of the virus genome, allowing to generate many different types of attenuated vectors possessing oncolytic activity, and the ability of HSV vectors to invade and establish lifelong non-toxic latent infections in neurons from sensory ganglia from where transgenes can be strongly and long-term expressed. Three different classes of vectors can be derived from HSV: replication-competent attenuated vectors, replication-incompetent recombinant vectors and defective helper-dependent vectors known as amplicons. Replication-defective HSV vectors are made by the deletion of one or more immediate-early genes, e.g. ICP4, which is then provided in trans by a complementing cell line. Oncolytic HSV vectors are promising therapeutic agents for cancer. Such HSV based vectors have been tested in glioma, melanoma and ovarian cancer patients.

It is particularly preferred that the viral vector is MVA.

The above listed preferred viral vectors have been evaluated regarding their safety profile in animals and/or humans and preclinical and clinical data are available, respectively.

In another preferred embodiment of the method of the invention, the replication-deficient viral vector is a virus like particle.

Virus like particles (VLPs) provide the advantage that they are not infectious and do not contain viral genetic material. Accordingly, they are not associated with any risk of reassembly as is possible when live attenuated viruses are used as viral vectors.

In another preferred embodiment of the method of the invention, the method further comprises adding an antigenic polypeptide.

An "antigenic polypeptide" in accordance with the present invention is not particularly limited, as long as it elicits an immune response. The antigenic polypeptide can be selected from e.g. viruses, bacteria, or tumor cells. For example, the antigenic polypeptide can be a viral surface protein of a virus other than the viral vector employed in the method of the invention, or a part thereof; or a main immunogenic viral protein or part thereof. These additional antigenic polypeptides can for example be used for priming the immune system in a prime-boost vaccination. In that case, the boost reaction is elicited by the respective viral vector or VLP relied on for preparing the viral vector-based composition by the method of the present invention. The term "polypeptide" as used herein interchangeably with the term "protein" describes linear molecular chains of amino acids, including single chain proteins or their fragments.

The step of adding the antigenic polypeptide can be carried out at different time points. For example, the antigenic polypeptide can be added to the replication-deficient viral vector provided in step (a). Alternatively, the antigenic polypeptide can be additionally admixed in step (c) or be added to the resulting composition subsequently to the mixing in step (c). Furthermore, as an additional alternative, the antigenic polypeptide can be added to the viral vector-based composition after reconstitution in step (e).

In a further preferred embodiment of the method of the invention, the method further comprises adding at least one adjuvant.

Adjuvants as well as their mode of action are well known in the art. Some adjuvants, such as alum and emulsions (e.g. MF59®), function as delivery systems by generating depots that trap the antigenic substance at the injection site, providing slow release in order to provide a continued stimulation of the immune system. These adjuvants enhance the antigen persistence at the injection site and increase the recruitment and activation of antigen presenting cells (APCs). Particulate adjuvants (e.g. alum) have the capability to bind antigenic substances to form multi-molecular aggregates which will encourage uptake by APCs. Some adjuvants are also capable of directing antigen presentation by the major histocompatibility complexes (MHC). Other adjuvants, essentially ligands for pattern recognition receptors (PRR), act by inducing the innate immunity, predominantly targeting the APCs and consequently influencing the adaptive immune response. Members of nearly all of the PRR families are potential targets for adjuvants. These include Toll-like receptors (TLRs), NOD-like receptors (NLRs), RIG-I-like receptors (RLRs) and C-type lectin receptors (CLRs). They signal through pathways that involve distinct adaptor molecules leading to the activation of different transcription factors. These transcription factors (NF-κB, IRF3) induce the production of cytokines and chemokines and IL-18.

Preferably, the at least one adjuvant is selected from Alum, MF59®, AS03, AF03, AS04, RC-529, Virosomen, ISCOMATRIX®, CpG 1018, CpG 7909, VaxImmune, Pro-Mune®, IC-31®, CTA1-DD or Cyclic di-AMP. These adjuvants, their class, indications and provider as well as product names are summarized in Table 2 below.

TABLE 2

Detailed informations on particularly preferred adjuvants.

| Adjuvant | Class | Main indications | Provider/Product |
|---|---|---|---|
| Alum | Aluminium salts<br>Aluminiumhydroxid<br>Aluminiumphosphate<br>Aluminiumhydroxyphosphate | various | various<br>world-wide |
| MF59 ® | Oil-in-Water emulsion<br>4.3% Squalen<br>0.5% Polysorbat 80<br>0.5% Sorbitantriolate<br>(Span 85 ®)<br>10 mM sodiumcitrate | Seasonal Influenza | Novartis/Fluad |
| AS03 | Oil-in-Water emulsion<br>10.69 mg Squalene<br>11.86 mg D,L-α-Tocopherol<br>(Vit. E)<br>4.86 mg Polysorbate 80 | Pandemic Influenza | GSK/Pandemrix |
| AF03 | Oil-in-Water emulsion<br>12.4 mg Squalene<br>1.9 mg Sorbitanoleate<br>2.4 mg Polysorbate 20<br>2.3 mg Mannitol | Pandemic Influenza | Sanofi Pasteur/<br>Humanza |
| AS04 | Kombination<br>Monophposphoryllipid A und<br>Aluminiumsalz | Hepatitis B virus<br>Human<br>Papillomavirus | GSK/Fendrix<br>Cervarix |
| RC-529 | Combination synthetic<br>monophposphoryllipid A and<br>aluminiumsalt | Hepatitis B virus | Dynavax |
| Virosomen | Phosphatidylcholine bilayer<br>liposomes 150 nm | Hepatitis A virus<br>Seasonal Influenza | Crucell/<br>Inflexal V |
| ISCOMATRIX ® | ISCOM Immunostimulating<br>Complex<br>Antigen<br>Cholesterol<br>Phospholipid<br>Saponin from *Quillaja Saponaria* | various | CSL Limited<br>Parkville, Victoria,<br>Australien |
| CpG 1018 | Oligodeoxynukleotide | Hepatitis B virus<br>Cancer | Dynavax/<br>HEPLISAV-B<br>SD-101 |

TABLE 2-continued

Detailed informations on particularly preferred adjuvants.

| Adjuvant | Class | Main indications | Provider/Product |
|---|---|---|---|
| CpG 7909 VaxImmune ProMune ® | Oligodeoxynukleotide | Cancer vaccination Hepatitis B virus Treatment of Cancer | Coley/Chiron/Pfizer GSK |
| IC-31 ® | Peptide and Oligodesoxynukleotid | Tuberkulosis | Intercell |
| CTA1-DD | Fusion protein from CTA1-Domaine of Cholera Toxins (CT) with maintaining ADP-ribosylating enzymatic function and a dimer from Ig binding domain of Protein A (*S. aureus*) as target domaine | | MIVAC Development AB in Sweden |

The step of adding the adjuvant can be carried out at different time points. For example, the adjuvant can be added to the replication-deficient viral vector provided in step (a). Alternatively, or additionally, the adjuvant can be admixed in step (c) or it can be added to the resulting composition subsequently to the mixing in step (c). As a further alternative or additional option, it can be added to the viral vector-based composition after reconstitution in step (e).

In another preferred embodiment of the method of the invention, at least one of the adjuvants is a saponine. Alternatively, the adjuvant is a mixture of substances comprising a saponine.

Saponines are a class of chemical compounds forming secondary metabolites which are found in natural sources, derived from natural sources or can be chemically synthesised. Saponines are found in particular abundance in various plant species. Saponines are amphipathic glycosides grouped phenomenologically by the soap-like foaming they produce when shaken in aqueous solutions, and structurally by their composition of one or more hydrophilic glycoside moieties combined with a lipophilic steroidal or triterpenoid aglycone. Their structural diversity is reflected in their physicochemical and biological properties. Non-limiting examples of saponines are glycyrrhizic acid, glycyrrhetinic acid, glucuronic acid, escin, hederacoside and digitonin.

Preferably, the saponine is selected from well-known adjuvant compositions, e.g., the saponine extracted from Quillaja Saponaria, as listed in Table 2, without being limiting.

In another embodiment, the saponine is glycyrrhizic acid or a derivative thereof. Glycyrrhizic acid is also known as glycyrrhicic acid, glycyrrhizin or glycyrrhizinic acid. Glycyrrhizic acid is water-soluble and exists as an anion that can be a potential ligand to form electrostatically associated complexes with cationic molecules of active ingredients. Without wishing to be bound by theory, the present inventors hypothesise that the anionic glycyrrhizic acid forms complexes with amino acids present in the solution of the present invention (i.e. arginine, or lysine) through electrostatic interactions, hydrogen bonds or both.

Derivatives of glycyrrhizic acid are well-known in the art and include those produced by transformation of glycyrrhizic acid on carboxyl and hydroxyl groups, by conjugation of amino acid residues into the carbohydrate part or the introduction of 2-acetamido-β-d-glucopyranosylamine into the glycoside chain of glycyrrhizic acid. Other derivatives are amides of glycyrrhizic acid, conjugates of glycyrrhizic acid with two amino acid residues and a free 30-COOH function and conjugates of at least one residue of amino acid alkyl esters in the carbohydrate part of the glycyrrhizic acid molecule. Examples of specific derivatives can be found e.g. in Kondratenko et al. (Russian Journal of Bioorganic Chemistry, Vol 30(2), (2004), pp. 148-153).

Preferred amounts of glycyrrhizic acid (or derivatives thereof) to be employed are between 0.01 and 15 mg/ml, preferably between 0.1 and 10 mg/ml, more preferably between 0.5 and 5 mg/ml, even more preferably between 1 and 3 mg/ml and most preferably the amount is 2 mg/ml.

As is known in the art, saponines, in particular glycyrrhizic acid, have been found to be advantageously present in function of an adjuvant, as they enhance the immunogenic effect of the viral vector based composition.

In another preferred embodiment of the method of the invention, the replication-deficient viral vectors of (a) are replication-deficient viral vectors that have been reconstituted immediately after harvesting from cell cultures and purification.

Means and methods for reconstituting replication-deficient viral vectors are well known in the art. For example, after amplification of a replication-deficient viral vector, such as e.g. MVA, in the appropriate cell culture model, crude stock preparations of MVA can be semi-purified from cell debris and recombinant proteins by ultracentrifugation through a sucrose cushion. After discarding the supernatant (cell debris and sucrose) the pelleted viral vector material can be mixed with a solution according to (b). Alternatively, to obtain more highly purified viruses, the semi-purified material can be centrifuged through a 25-40% sucrose gradient. The viral vector band appearing at the lower half of the tube is concentrated and the remaining sucrose is simultaneously removed by filling an ultracentrifuge tube with the solution according to (b), pelleting the viral vector material by ultracentrifugation and suspending the pellet in a solution according to (b).

The decrease in the amount of infectious particles present in a composition as compared to non-infectious particles due to an increasing polydispersity starts immediately after harvesting viral particles from cell culture. Thus, it is particularly preferred in accordance with the present invention that the replication-deficient viral vectors are mixed with the solution of (b) as early as possible after the initial harvesting of the viral vectors.

Figure 9:
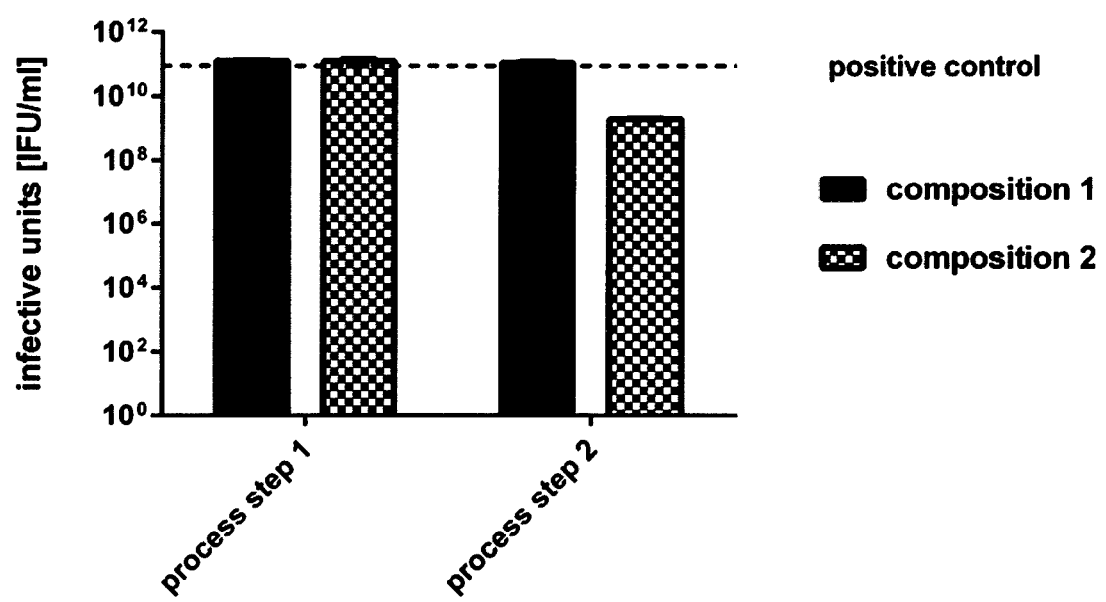

As shown in e.g. example 2 below, the early addition of the stabilizing compositions, particularly composition 1 and 2 can have a strong impact on the stability of the adenoviral vector preparation during its entire preparation procedure. The in vitro infectivity analysis of the adenoviral preparations after re-buffering by dialysis in composition 1 and 2, respectively either directly after the purification step by CsCl density ultracentrifugation (process step 1), or later in the preparation process (process step 2) revealed differences between the two applied stabilizing compositions. Re-buffering in composition 1 according to the preparation in process step 1 and 2 led to the complete retention of the infectivity directly after dialysis (Example 2; FIG. 9) and after application of 5 and 10 freeze and thaw cycles compared to the positive control depicted as dashed line (Example 2; FIGS. 11A and B). Re-buffering in composition 2 during an earlier step of the preparation process (process step 1) led also to complete retention of the infectivity directly after dialysis and minor loss of the infective titer after application of repeated freeze and thaw cycles (Example 2; FIG. 9 and FIG. 11A). In contrast, re-buffering in composition 2 during preparation in process step 2 led to a remarkable reduction in the infective titer already directly after the dialysis Example 2; FIG. 9). Further application of repeated freeze and thaw cycles resulted in a further, significant decrease of the infective titer (Example 2; FIG. 11B).

Thus, the early application of the stabilizing composition according to the invention was found to have a pronounced stabilizing effect on the particular biomolecule during the entire production process.

These results of the in vitro infectivity experiments correspond well with the DLS experiments performed in parallel. In FIGS. 10A and B the results of the determination of the hydrodynamic radii of the adenoviral particles after the preparation in composition 1 and 2 during process step 1 indicate the complete retention of the adenoviral particle size after preparation of the formulations directly after the purification step using ultracentrifugation which is in line with the infectivity results in FIG. 9. In the case of composition 1, after re-buffering the adenoviral vector preparation according to process step 2 a slight increase of the hydrodynamic particle radii was observed (FIG. 10C) which is in accordance with the infectivity results shown in FIG. 9. In contrast, re-buffering of the adenoviral vector preparation in composition 2 corresponding to processing step 2 resulted in a remarkable increase of the hydrodynamic radius of the adenoviral particles (FIG. 10D) accompanied by the formation of higher order aggregates that may explain the loss of function in the in vitro infectivity tests (FIG. 9).

After five and ten repeated freeze and thaw cycles, changes in the hydrodynamic radii of viral particles, particularly in composition 2 were measured by DLS. No remarkable increase was observed in composition 1 after five and even after ten freeze and thaw cycles when prepared during process steps 1 and 2 (Example 2; FIGS. 12A and B and 13A and B). When composition 2 was used during process step 1 the hydrodynamic radii already after five freeze and thaw cycles were remarkably increased in conjunction with the formation of higher order aggregates (Example 2; 13 C and D) and were not measurable after ten freeze and thaw cycles and when used in process step 2 due to further increased radii and higher order aggregates which were outside the DSL measure limit.

The present invention further relates to a viral vector-based composition obtained or obtainable by the method of the invention.

These viral vector-based compositions may be used for anti-bacterial, antiviral, anti-cancer, anti-allergy vaccination and/or for gene transfer therapy for the treatment of diseases with a genetic background.

In a preferred embodiment, the composition is a pharmaceutical composition.

In accordance with the present invention, the term "pharmaceutical composition" relates to a composition for administration to a patient, preferably a human patient.

The pharmaceutical compositions can be administered to the subject at a suitable dose. The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently. The therapeutically effective amount for a given situation will readily be determined by routine experimentation and is within the skills and judgment of the ordinary clinician or physician. The pharmaceutical composition may be for administration once or for a regular administration over a prolonged period of time. Generally, the administration of the pharmaceutical composition should be in the range of for example 1 µg/kg of body weight to 50 mg/kg of body weight for a single dose. However, a more preferred dosage might be in the range of 10 µg/kg to 20 mg/kg of body weight, even more preferably 100 µg/kg to 10 mg/kg of body weight and even more preferably 500 µg/kg to 5 mg/kg of body weight for a single dose.

The components of the pharmaceutical composition to be used for therapeutic administration must be sterile. Sterility is readily accomplished for example by filtration through sterile filtration membranes (e.g., 0.2 µm membranes).

The various components of the composition may be packaged as a kit with instructions for use.

Accordingly, the present invention further relates to a kit comprising a viral vector-based composition obtained or obtainable by the method of the invention and, optionally, instructions how to use the kit.

Whereas the term "kit" in its broadest sense does not require the presence of any other compounds, vials, containers and the like other than the recited components, the term "comprising", in the context of the kit of the invention, denotes that further components can be present in the kit. Non-limiting examples of such further components include antigenic polypeptides or adjuvants, as defined above, as well as preservatives, buffers for storage, enzymes etc.

Where several components are comprised in the kit, the various components of the kit may be packaged in one or more containers such as one or more vials. Consequently, the various components of the kit may be present in isolation or combination. The containers or vials may, in addition to the components, comprise preservatives or buffers for storage. In addition, the kit can contain instructions for use.

In a preferred embodiment of the kit of the invention, the kit comprises a viral vector-based composition obtained or obtainable by the method of the invention and, in the same or a separate container, an antigenic polypeptide. These separate containers with i) the viral vector-based composition and ii) the antigenic polypeptide can be used in separate vaccination steps (either simultaneously or subsequently to each other), e.g. for a prime-boost immunization approach.

In an alternative or additional preferred embodiment of the kit of the invention, the kit comprises a viral vector-based composition obtained or obtainable by the method of the invention and, in the same or a separate container, one or more adjuvants.

Also envisaged is a kit, comprising (i) a viral vector-based composition obtained or obtainable by the method of the invention; (ii) an antigenic polypeptide and (iii) one or more adjuvants, in the same or different containers.

The present invention also relates to the viral vector-based composition of the invention for use as a prime-boost vaccine.

The "prime-boost vaccine strategy" is well known in the art and encompasses a first step of "priming" an immune response, followed by a second step of "boosting" the previously primed immune response. This approach enables high levels of antigen specific T-cell memory as well as protective cellular immunity to pathogens, even in humans, and thus is a promising approach in vaccination (Woodland D L, Trends in Immunology, 2004; Nolz J C, Harty J T. Adv Exp Med Biol. 2011; 780:69-83. doi: 10.1007/978-1-4419-5632-3_7. Strategies and implications for prime-boost vaccination to generate memory CD8 T cells).

Viral vector-based compositions are highly attractive for therapeutic prime-boost vaccine approaches. For example, prophylactic vaccination for the prevention of HBV infection is well established. In contrast, an effective therapy of chronic hepatitis due to HBV infection and its sequalae is currently not available and might be successfully addressed by a prime-boost vaccination strategy with a specific antigen prime and a subsequent specific viral vector-based boost that induces antigen specific antibody production as well as antigen specific T cell responses both resulting in a highly efficient vaccination outcome. As discussed herein above, the data provided in the appended Examples show that the biological, immunogenic activity of a viral vector-based composition prepared by the method of the present invention is improved as compared to viral vector-based compositions prepared by other methods. In other words, the ability of the inventive viral vector-based compositions to stimulate the immune system of a subject, such as e.g. to elicit cytotoxic T lymphocytes (CTL) of the immune system to protect the subject against the disease for which the vaccine has been developed, is improved.

In a further preferred embodiment of the invention, the viral vector-based composition is for intramuscular, subcutaneous, intradermal, transdermal, oral, peroral, nasal, and/or inhalative application.

Unless otherwise defined, all technical and scientific terms used herein have the same meaning as commonly understood by one of ordinary skill in the art to which this invention belongs. In case of conflict, the patent specification, including definitions, will prevail.

Regarding the embodiments characterized in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The above considerations apply mutatis mutandis to all appended claims. To give a non-limiting example, the combination of claims 12, 8, 4, 3 and 1 is clearly and unambiguously envisaged in view of the claim structure. The same applies for example to the combination of claims 12, 8 and 1 etc.

Figure 2:
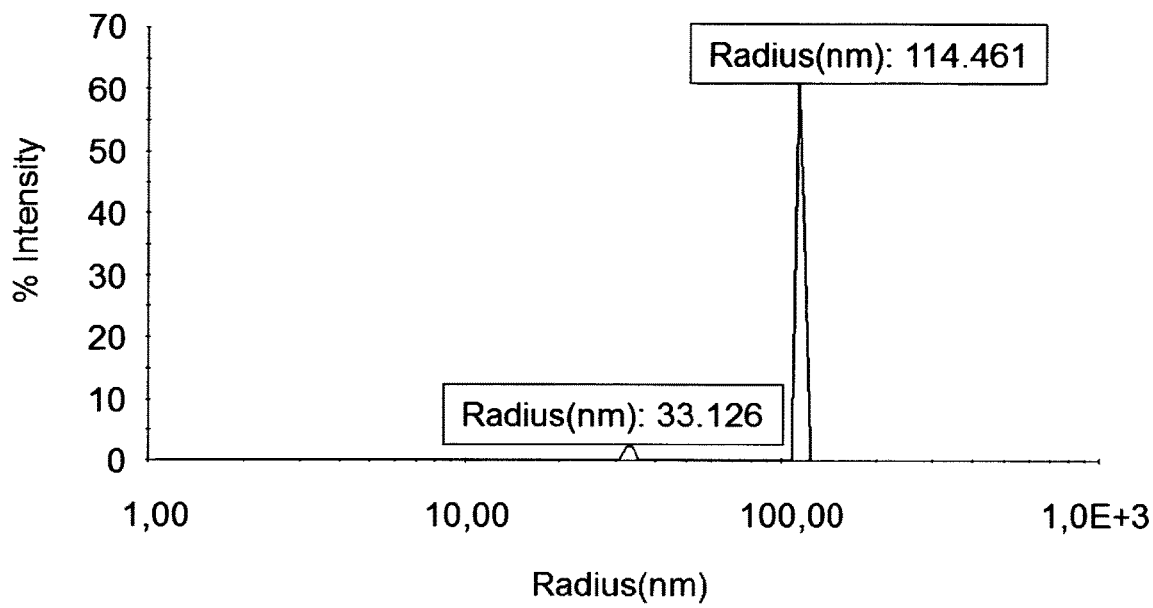
Figure 2:
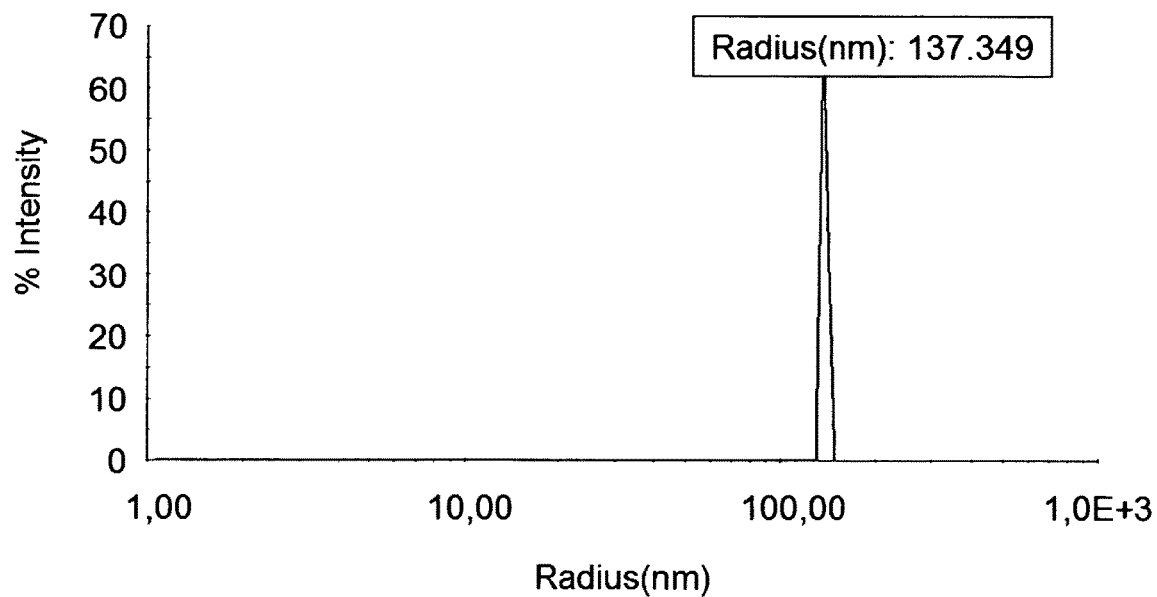

The invention is illustrated with the following figures which show:

FIG. 1: Dynamic Light Scattering (DLS) determination of the hydrodynamic radii of the adenoviral vector compositions before freeze drying as a model for aggregation and polydispersity in a suspension. (A) Evaluation of the correlation function recorded in the DLS experiments using a regularization fit by the DynaPro DLS software of the adenoviral stock solution as a control, (B) evaluation of the correlation function of the adenoviral vector preparation directly after mixing with composition 1 by dilution and (C) evaluation of the correlation function of the adenoviral vector preparation directly after mixing with composition 2 by dilution. The calculated hydrodynamic radii of the adenoviral vector preparations in composition 1 and 2 are in line with the measured radii of the adenoviral particles in the untreated stock solution and with values known from the literature.

FIG. 2: Dynamic Light Scattering (DLS) determination of the hydrodynamic radii of the adenoviral vector compositions before freeze drying as a model for aggregation and polydispersity in a suspension. (A) Evaluation of the correlation function recorded in the DLS experiments using a regularization fit by the DynaPro DLS software of the adenoviral vector preparation directly after mixing with the original supplier formulation and (B) evaluation of the correlation function of the adenoviral vector preparation directly after mixing with PBS. In contrast to the previous figure, the hydrodynamic radii of the adenoviral particles after mixing with the original supplier formulation and with PBS are increased compared to the untreated stock solution.

FIG. 3: In vitro infectivity of adenoviral vectors after freeze drying in different formulations as a model for functionality under freeze drying stress conditions. Adenoviral vector preparations were formulated by dilution and subsequently freeze-dried in composition 1 and 2. After reconstitution of the freeze-dried vectors an in vitro infectivity assay in HEK 293 cells was carried out using an antibody based colorimetric detection of the adenoviral Hexon protein to indicate a successful amplification of the adenovirus in the infected cells. A complete retention of the infective titers of the adenoviral vector preparations formulated in composition 1 and 2 was observed (infective units per ml as compared to positive control; depicted as dashed line). In contrast, freeze drying of the adenoviral vectors diluted in the original supplier formulation led to a remarkable loss of the infective titers and freeze drying of the adenoviral vectors diluted in PBS resulted in a complete loss of the corresponding infective titers.

Figure 4:
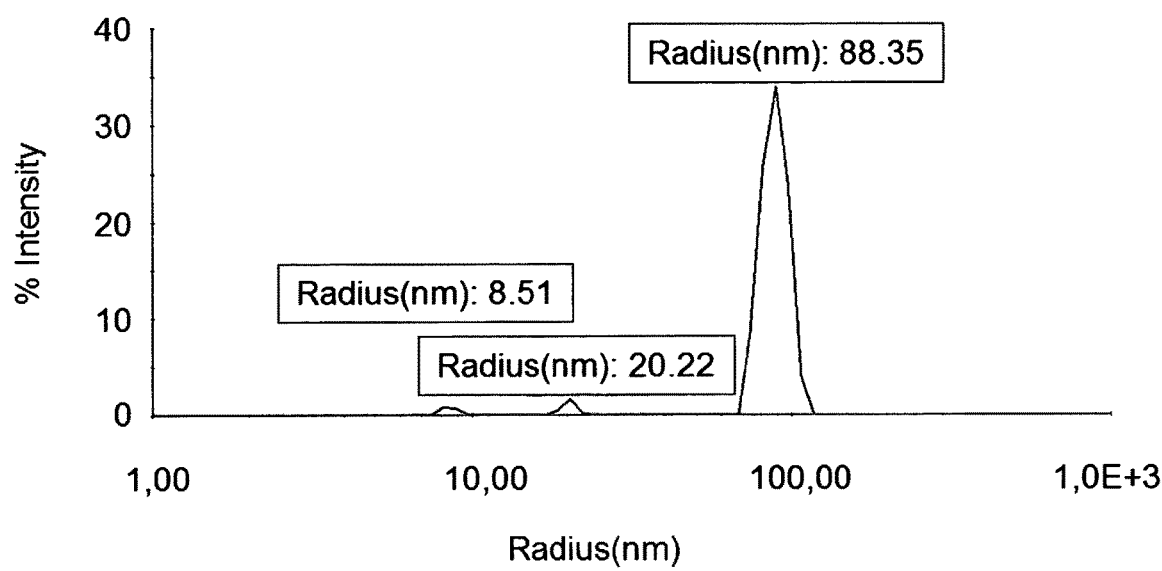
Figure 4:
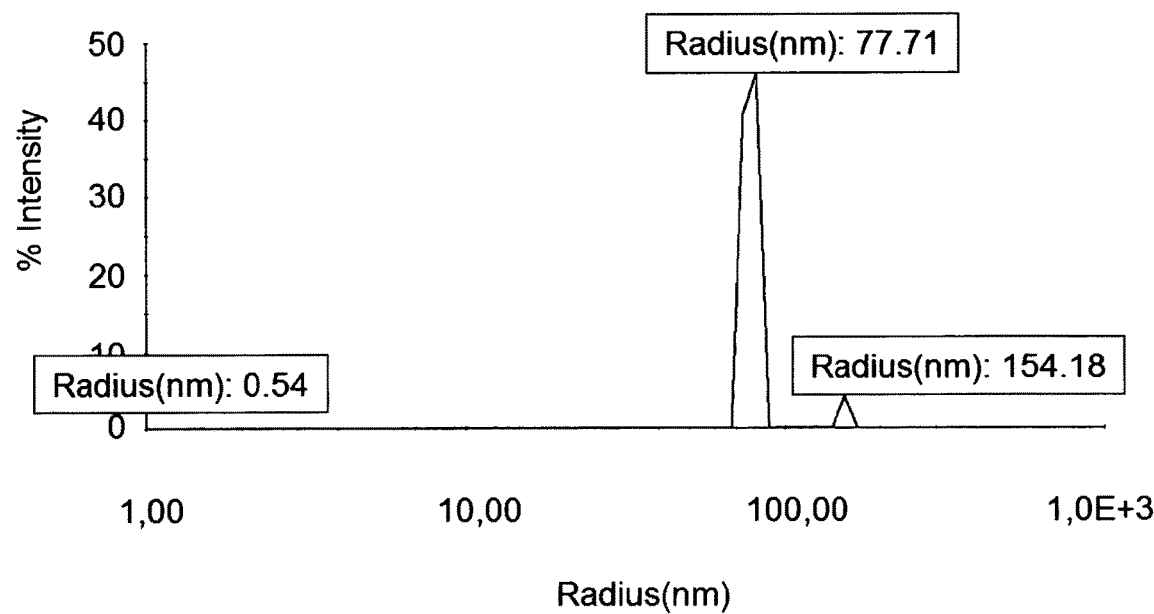

FIG. 4: Dynamic Light Scattering (DLS) determination of the hydrodynamic radii of the adenoviral particles in the corresponding adenoviral vector preparations after freeze drying as a model for aggregation and polydispersity under freeze drying stress conditions. (A) Evaluation of the correlation function recorded in the DLS experiment using a regularization fit by the DynaPro DLS software of the adenoviral vector preparation after freeze drying in composition 1, (B) evaluation of the adenoviral vector preparation after freeze drying in composition 2. The calculated hydrodynamic radii of the adenoviral vector preparations in composition 1 and 2 are in line with the measured radii of the adenoviral particles in the untreated stock solution (FIG. 1A) and with values known from the literature.

FIG. 5: Dynamic Light Scattering (DLS) determination of the hydrodynamic radii of the adenoviral particles in the corresponding adenoviral vector preparations after freeze drying as a model for aggregation and polydispersity under freeze drying stress conditions. (A) Evaluation of the correlation function recorded in the DLS experiment using a regularization fit by the DynaPro DLS software of the adenoviral vector preparation directly after freeze drying in the original supplier formulation and (B) evaluation of the correlation function of the adenoviral vector preparation directly after freeze drying in PBS. In contrast to the previous figure, the hydrodynamic radii of the adenoviral particles after freeze drying in the original supplier formulation and in PBS are increased associated with the formation of higher order aggregates compared to the untreated stock solution (FIG. 1A).

FIG. 6: in vitro infectivity of adenoviral vectors after freeze drying in different formulations and subsequent storage of the dried formulations at elevated temperatures as a model for functionality under thermal stress conditions. t=0 d (black bars on the left) shows the in vitro infectivity directly after freeze drying and reconstitution before storage. The dashed line shows the corresponding infective titer of the untreated positive control. (A) In vitro infectivity of the adenoviral vector compositions after re-buffering by dilution in composition 1 and 2 and subsequent storage of the freeze-dried formulations for 21 days (set of bars in the middle) and 42 days (set of bars on the right) at 25° C. and at 60% residual humidity, as compared to the original supplier buffer and PBS. (B) In vitro infectivity of the adenoviral vector compositions after re-buffering by dilution in composition 1 and 2 and subsequent storage of the freeze-dried formulations for 7 days (set of bars in the middle) and 28 days (set of bars on the right) at 40° C. and at 75% residual humidity, as compared to the original supplier buffer and PBS. Complete retention of the adenoviral infectivity was observed in the samples prepared in the compositions 1 and 2, whereas storage in either the original supplier buffer or in PBS led to the complete loss of adenoviral infectivity.

Figure 7:
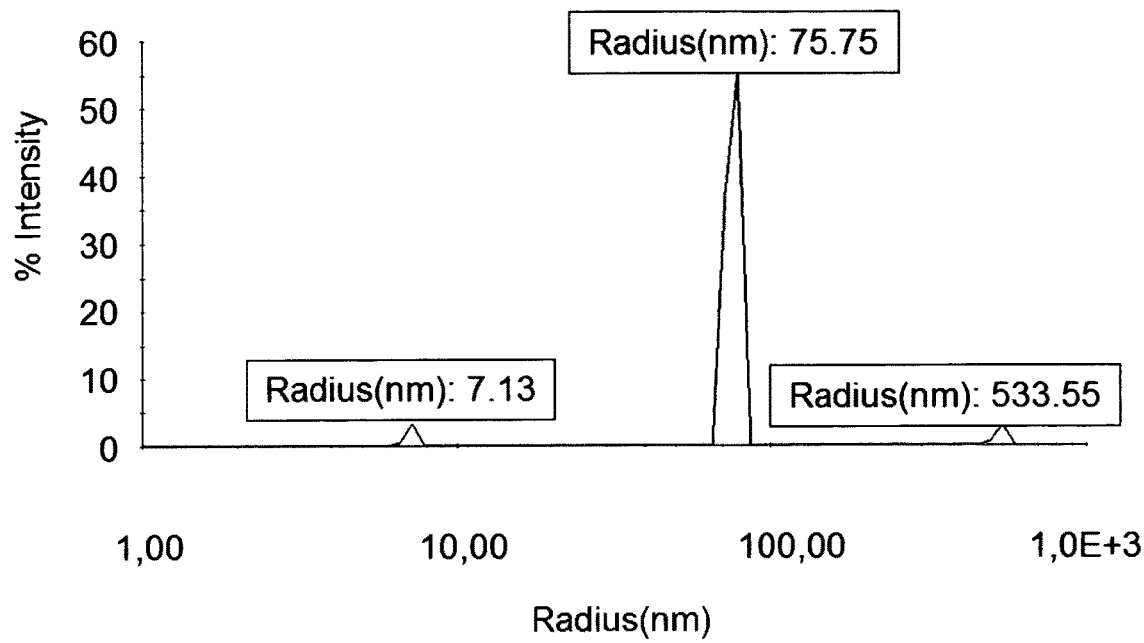
Figure 7:
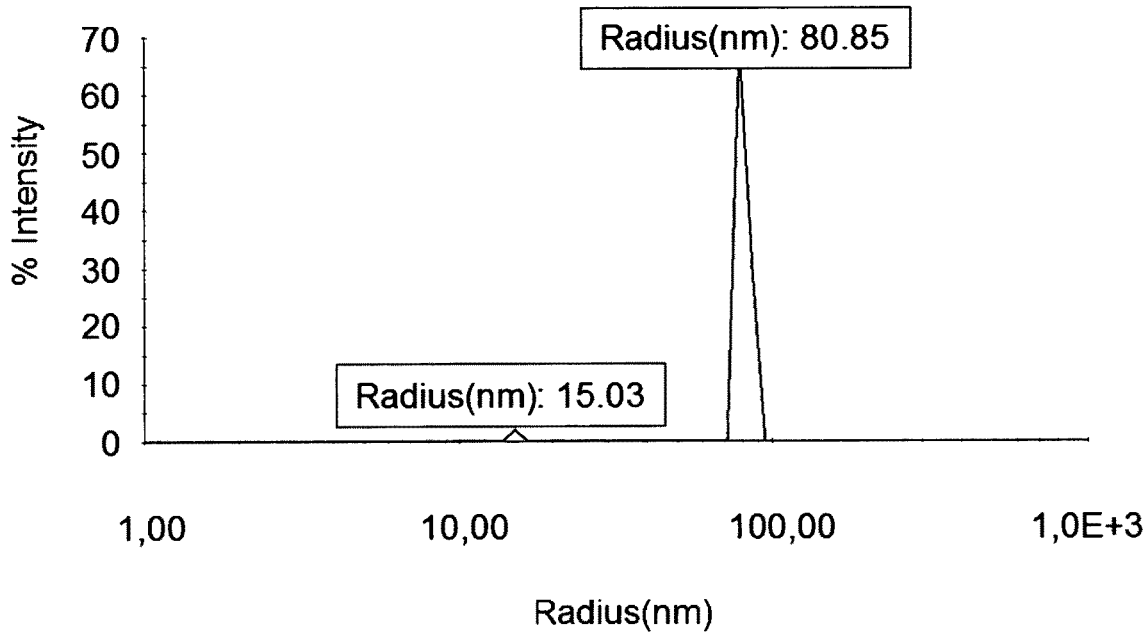

FIG. 7: Dynamic Light Scattering (DLS) determination of the hydrodynamic radii of the adenoviral particles in the corresponding adenoviral vector preparations after freeze drying and subsequent storage for 14 days at 40° C. as a model for aggregation and polydispersity under thermal stress conditions. (A) Evaluation of the correlation function recorded in the DLS experiment using a regularization fit by the DynaPro DLS software of the adenoviral vector preparation after storage of the dried formulations for 14 days at 40° C. in composition 1 and (B) evaluation of the adenoviral vector preparation after storage of the dried formulations for 14 days at 40° C. in composition 2. The calculated hydrodynamic radii of the adenoviral vector preparations in composition 1 and 2 are in line with the measured radii of the adenoviral particles in the untreated stock solution (FIG. 1A) and with values known from the literature.

Figure 8:
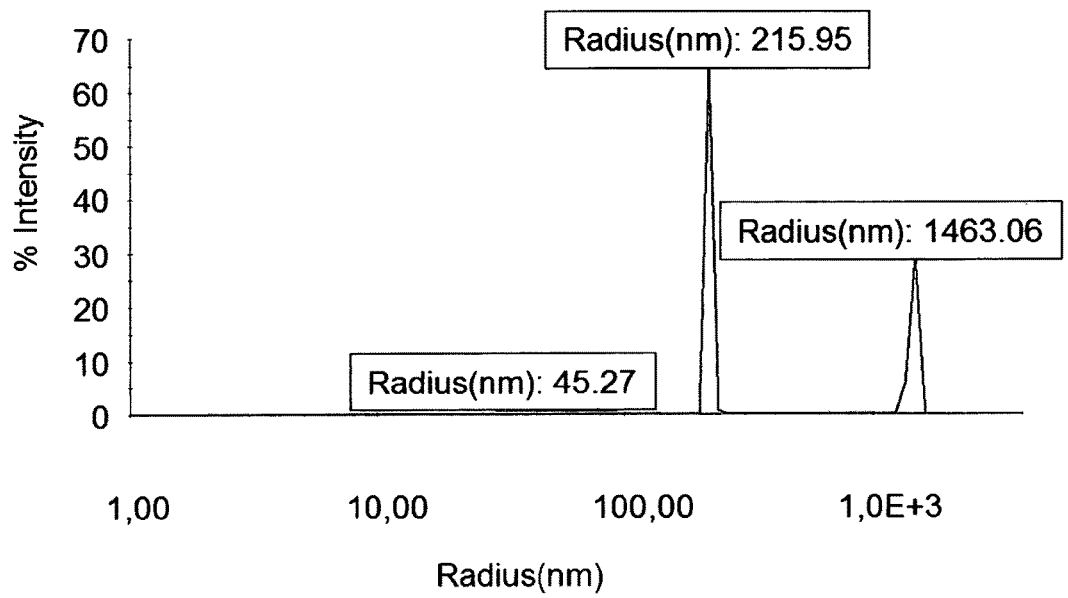
Figure 8:
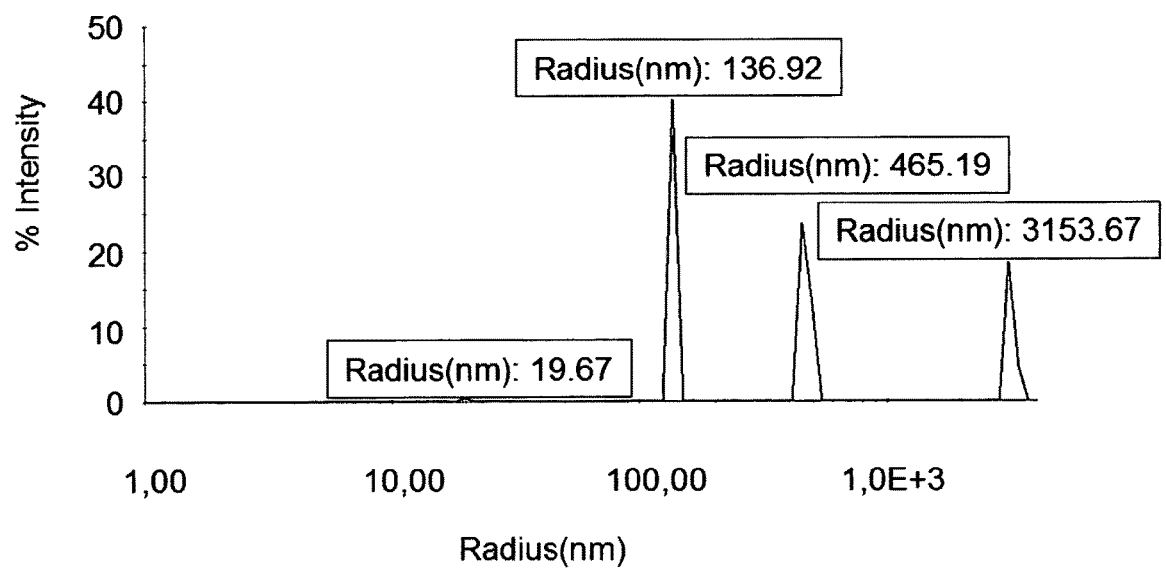

FIG. 8: Dynamic Light Scattering (DLS) Determination of the hydrodynamic radii of the adenoviral particles in the corresponding adenoviral vector preparations after freeze drying as a model for aggregation and polydispersity under thermal stress conditions. (A) Evaluation of the correlation function recorded in the DLS experiment using a regularization fit by the DynaPro DLS software of the adenoviral vector preparation after freeze drying and subsequent storage for 14 days at 40° C. in the original supplier formulation and (B) evaluation of the correlation function of the adenoviral vector preparation after freeze drying and subsequent storage for 14 days at 40° C. in PBS. In contrast to the previous figure, the hydrodynamic radii of the adenoviral particles after freeze drying and subsequent storage at elevated temperature in the original supplier formulation and with PBS are increased compared to the untreated stock solution associated with the formation of higher order aggregates.

FIG. 9: In vitro infectivity of adenoviral vector preparations after formulation in stabilizing compositions 1 and 2 prepared during either process step 1 or process step 2 as a model for functionality under thermal stress conditions. Adenoviral preparations were re-buffered by dialysis in composition 1 and 2, respectively either directly after the purification step by CsCl density ultracentrifugation (process step 1), or later in the preparation process (process step 2). In process step 1, a complete retention of the infective titer after dialysis in both compositions was observed compared to the positive control (depicted as dashed line). In contrast, dialysis during process step 2 led to a remarkable loss of infective titers of nearly two log levels when carried out in composition 2, whereas dialysis in composition 1 led to the complete retention of the infective titer, similar to the results obtained for process step 1.

Figure 10:
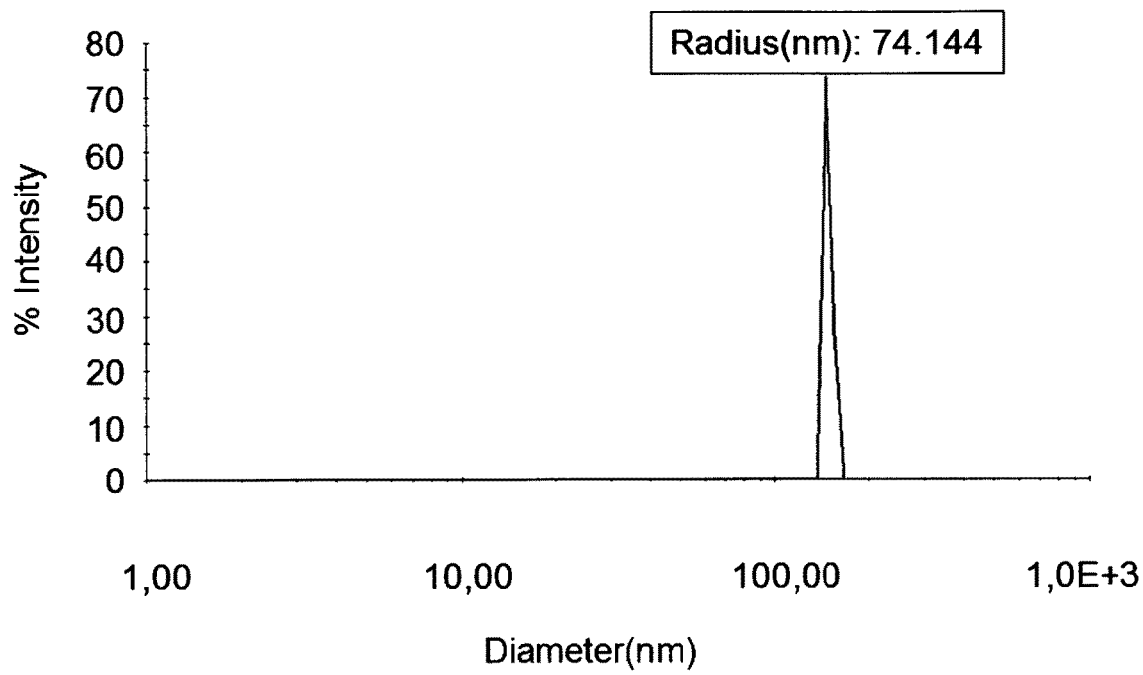
Figure 10:
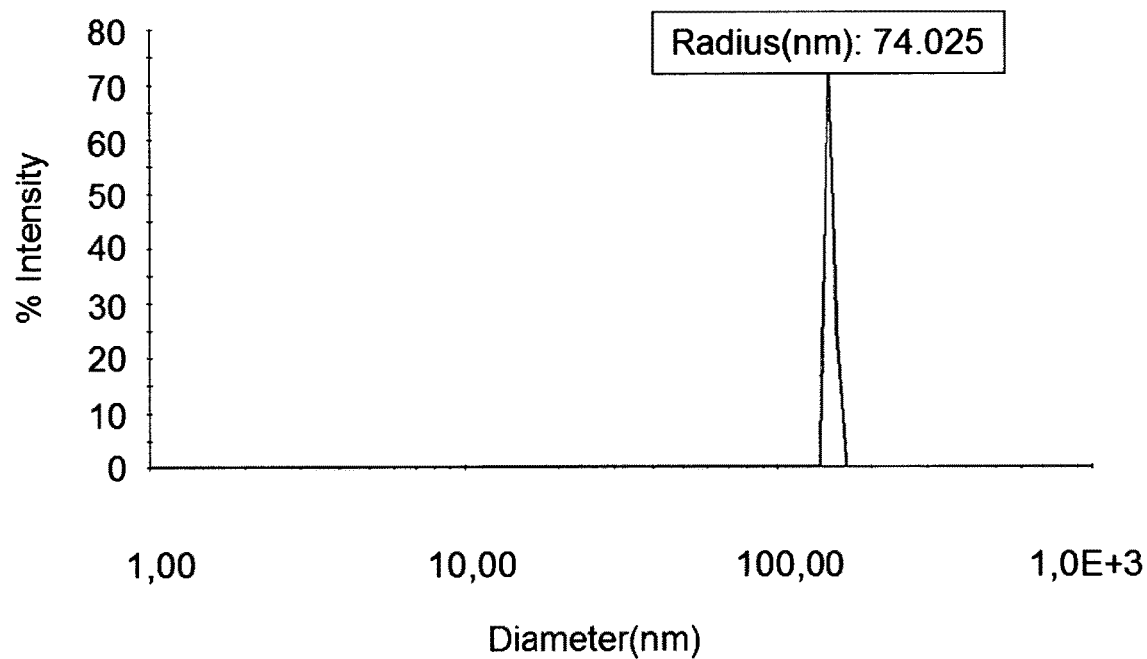
Figure 10:
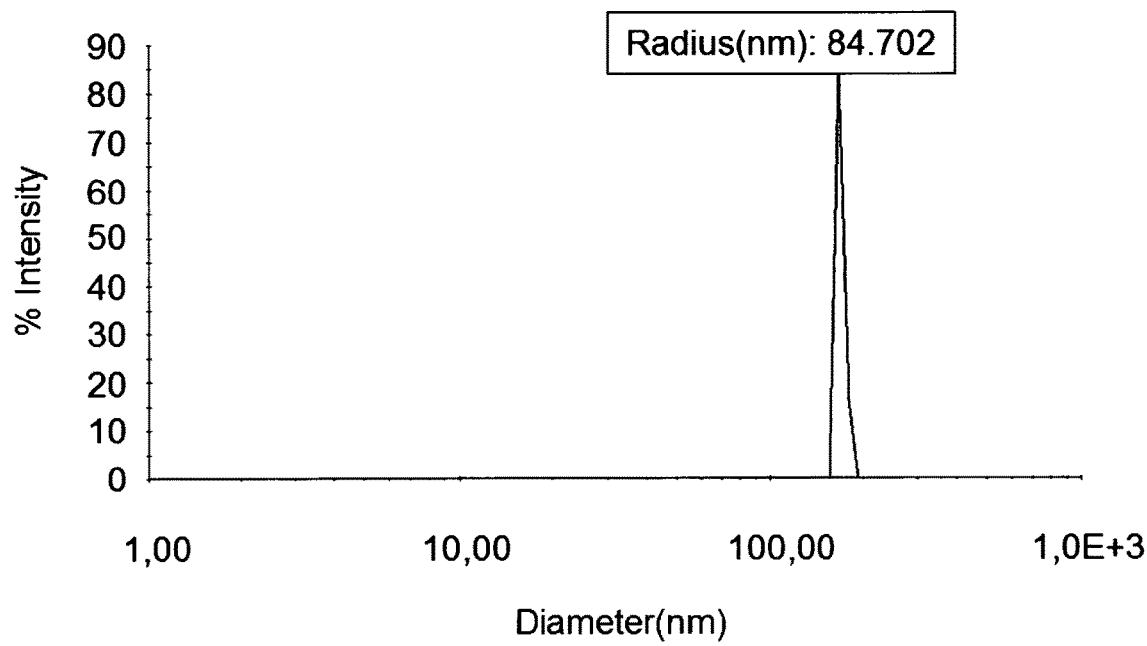
Figure 10:
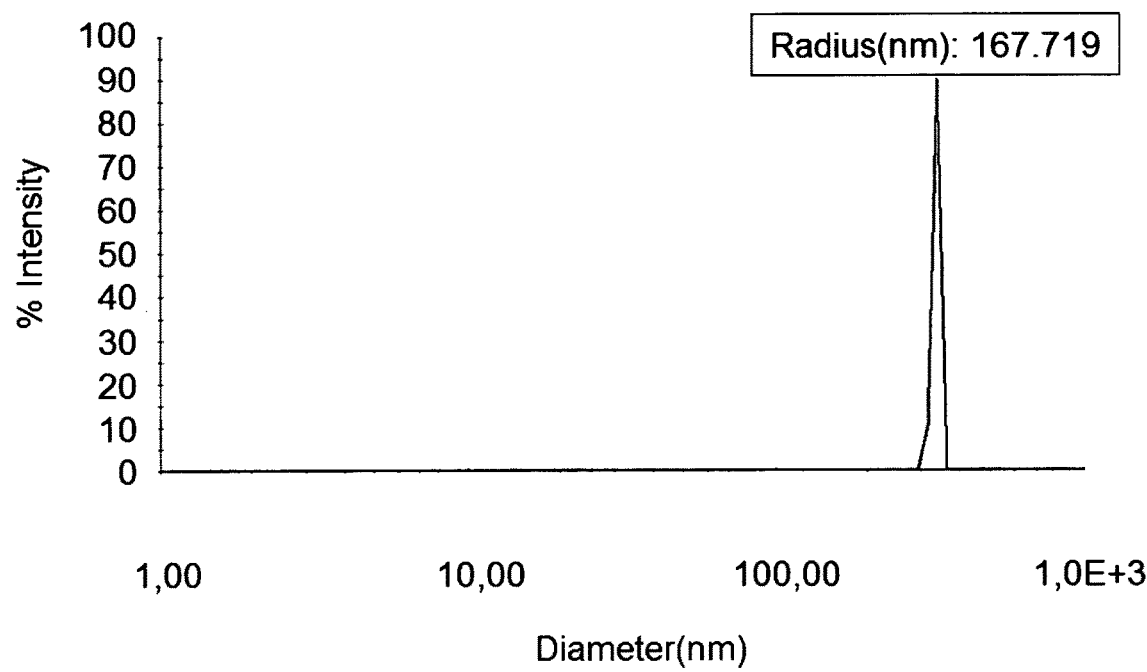

FIG. 10: Dynamic Light Scattering (DLS) determination of the hydrodynamic radii of the adenoviral particles in the corresponding adenoviral vector preparations after formulation in stabilizing compositions 1 and 2 during either process step 1 or process step 2, as a model for aggregation and polydispersity. Re-buffering of the adenoviral vector particle preparations in composition 1 using dialysis either in process step 1 or 2 resulted in the retention of the hydrodynamic radii of the particles (A) and (C). Re-buffering of the adenoviral particles in composition 2 during preparation in process step 1 led to the complete retention of the hydrodynamic radius of the adenoviral vector (B). In contrast, re-buffering of the adenoviral particles in composition 2 during preparation in process step 2 led to an increase in the hydrodynamic radius of the particles and the associated formation of large aggregates (D).

Figure 11:
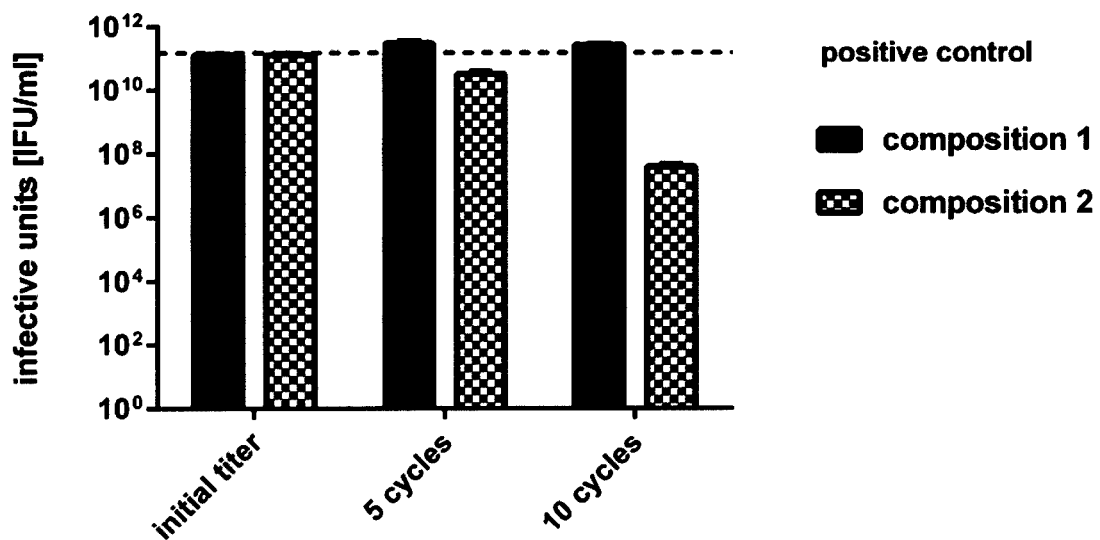
Figure 11:
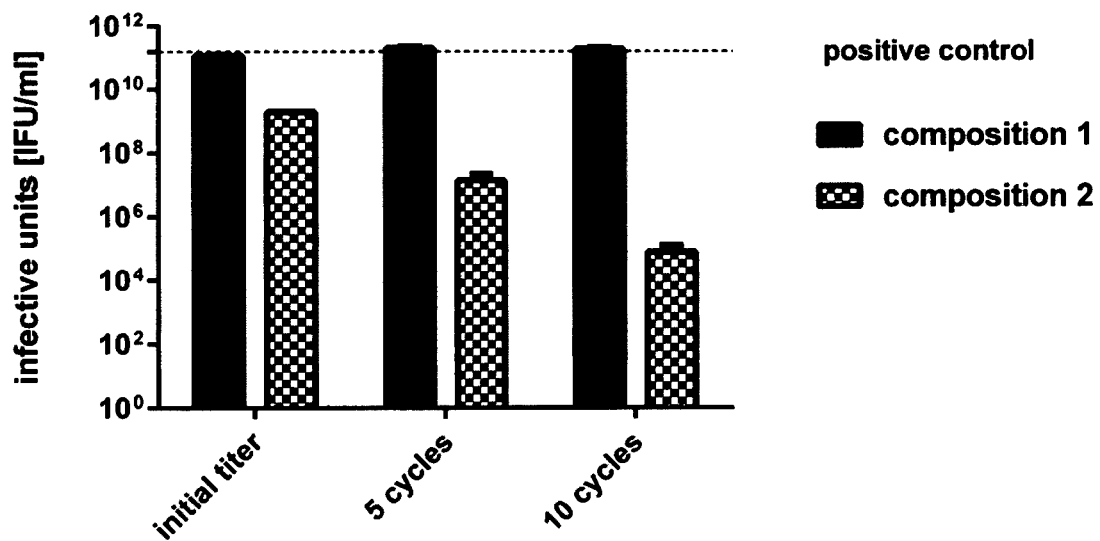

FIG. 11: In vitro infectivity of the adenoviral vector preparations after repeatedly applied freeze and thaw cycles as a model for functionality under stress conditions. (A) Re-buffering of the adenoviral vector preparations by dialysis during preparation in process step 1. (B) Re-buffering of the adenoviral vector preparations by dialysis during preparation in process step 2. In both preparation procedures (process step 1 and 2), re-buffering in composition 1 led to the complete retention of the infectivity directly after dialysis (initial titer) and after application of 5 and 10 freeze and thaw cycles (A) and (B) compared to the positive control depicted as dashed line. Re-buffering in composition 2 during an earlier step of the preparation process (process step 1) led also to complete retention of the infectivity directly after dialysis (initial titer; A, left set of bars) and minor loss of the infective titer after application of repeated freeze and thaw cycles (A). In contrast, re-buffering in composition 2 during preparation in process step 2 led to a remarkable reduction in the infective titer already directly after the dialysis (B; left set of bars). Further application of repeated freeze and thaw cycles resulted in a further, significant decrease of the infective titer (B; middle and right set of bars).

Figure 12:
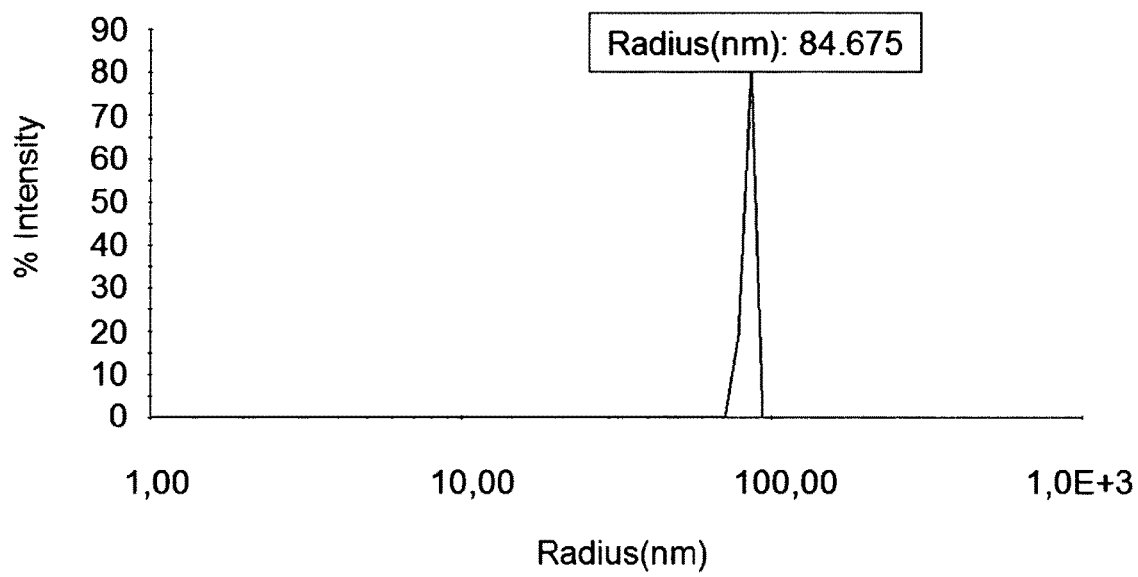
Figure 12:
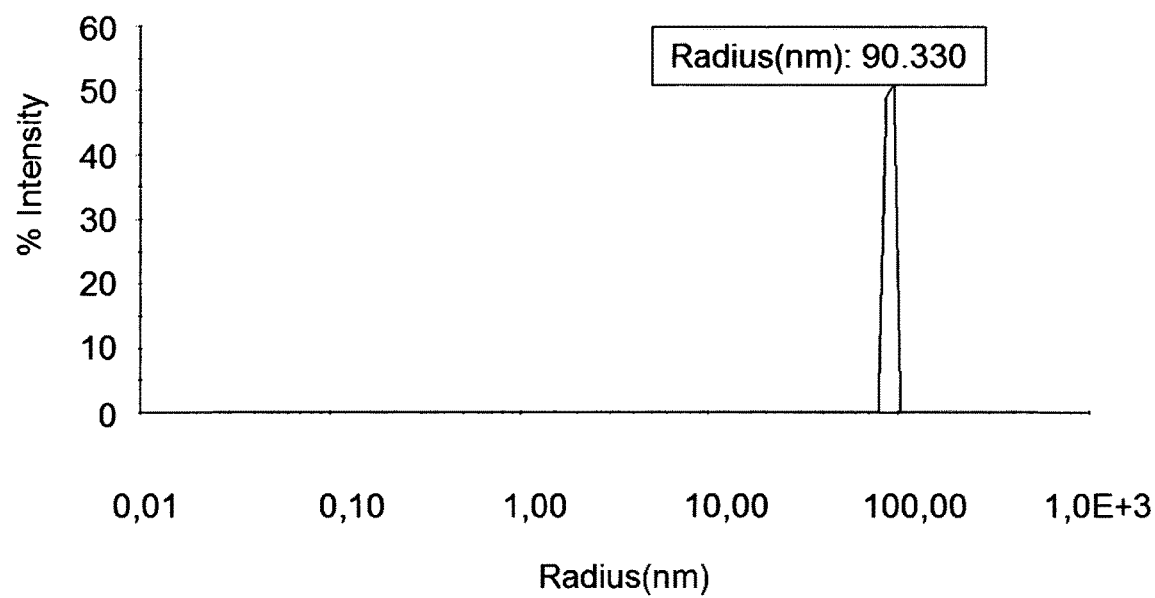

FIG. 12: Dynamic Light Scattering (DLS) Determination of the hydrodynamic radii of the adenoviral particles in the stabilizing compositions 1 after application of either five or ten freeze and thaw cycles as a model for aggregation and polydispersity under stress conditions. Re-buffering of the adenoviral vector particle preparations in composition 1 using dialysis in process step 2 resulted in the retention of the hydrodynamic radii of the particles (A) after the application of five freeze and thaw cycles and (B) after application of ten freeze and thaw cycles.

Figure 13:
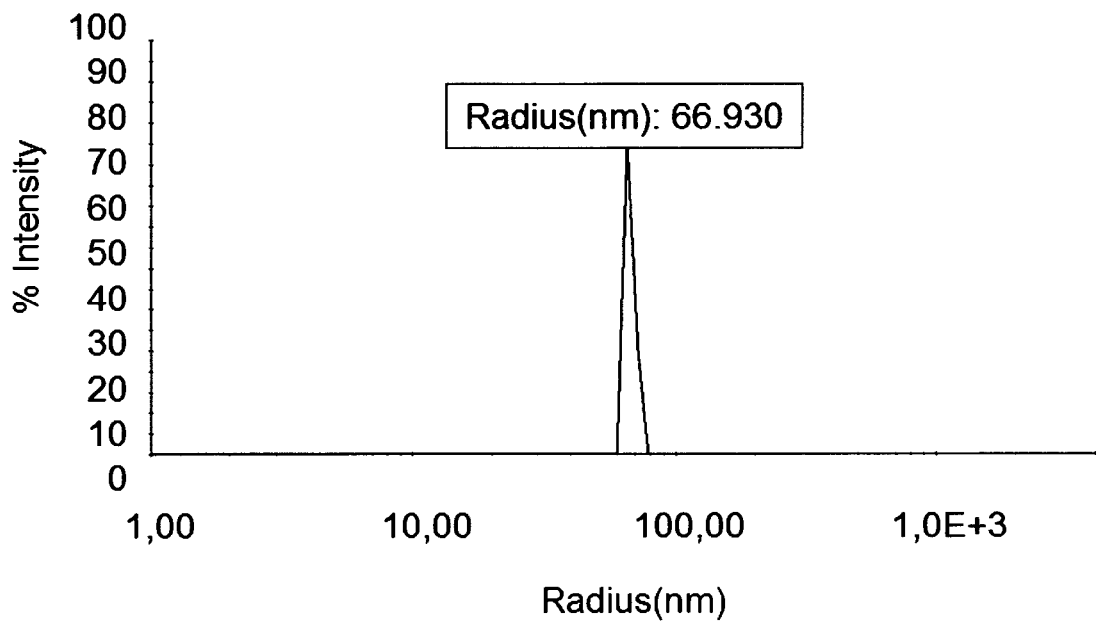
Figure 13:
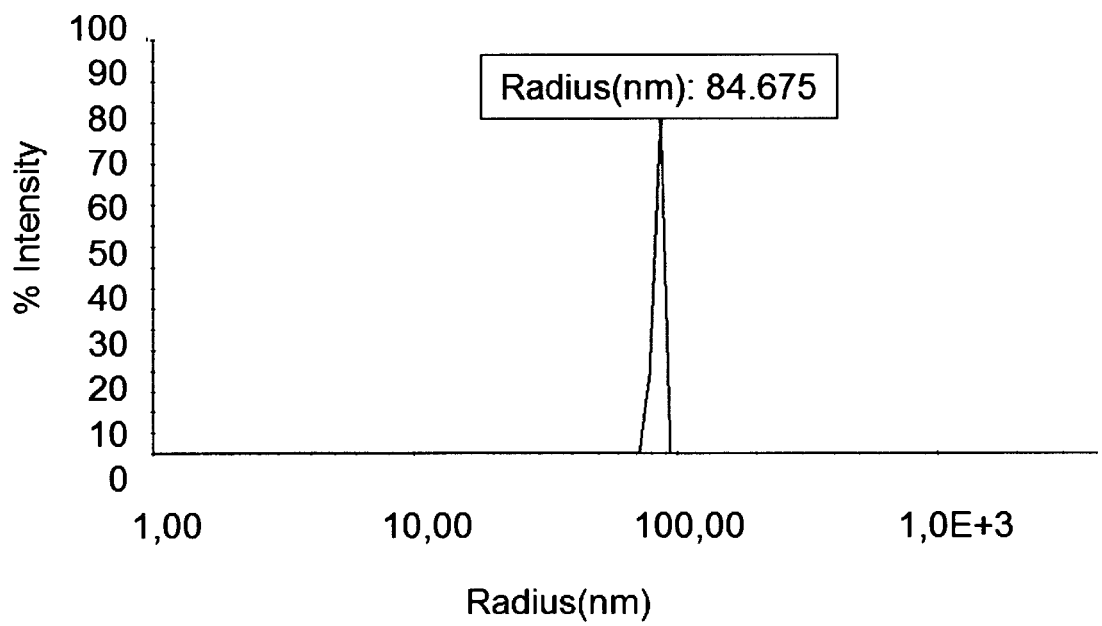
Figure 13:
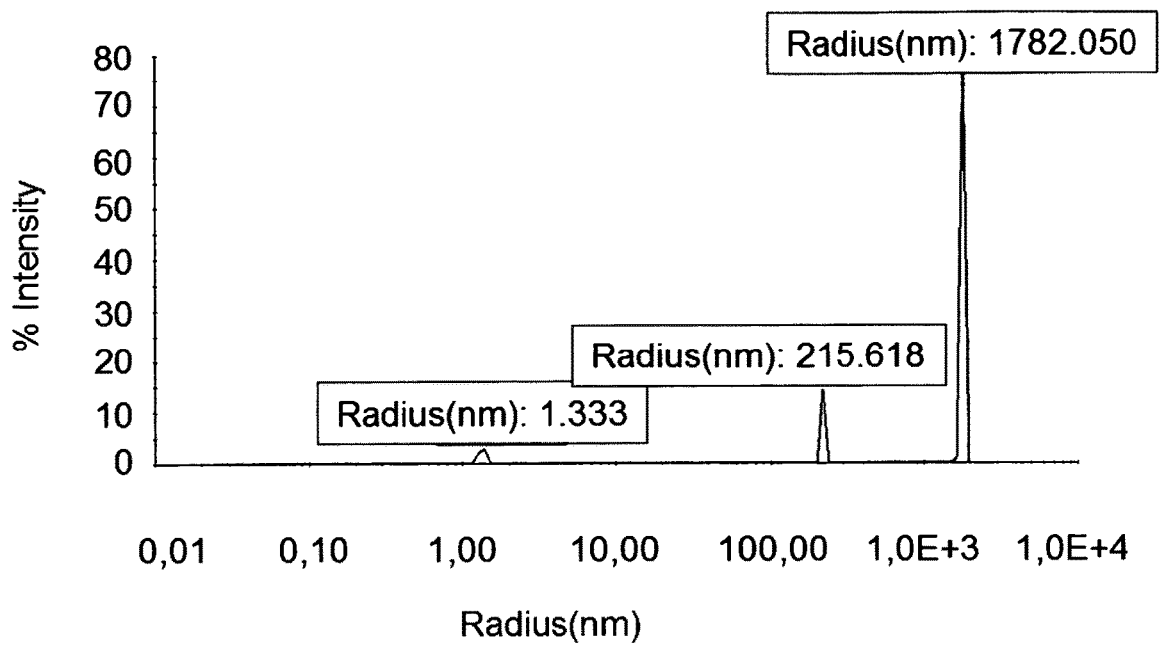
Figure 13:
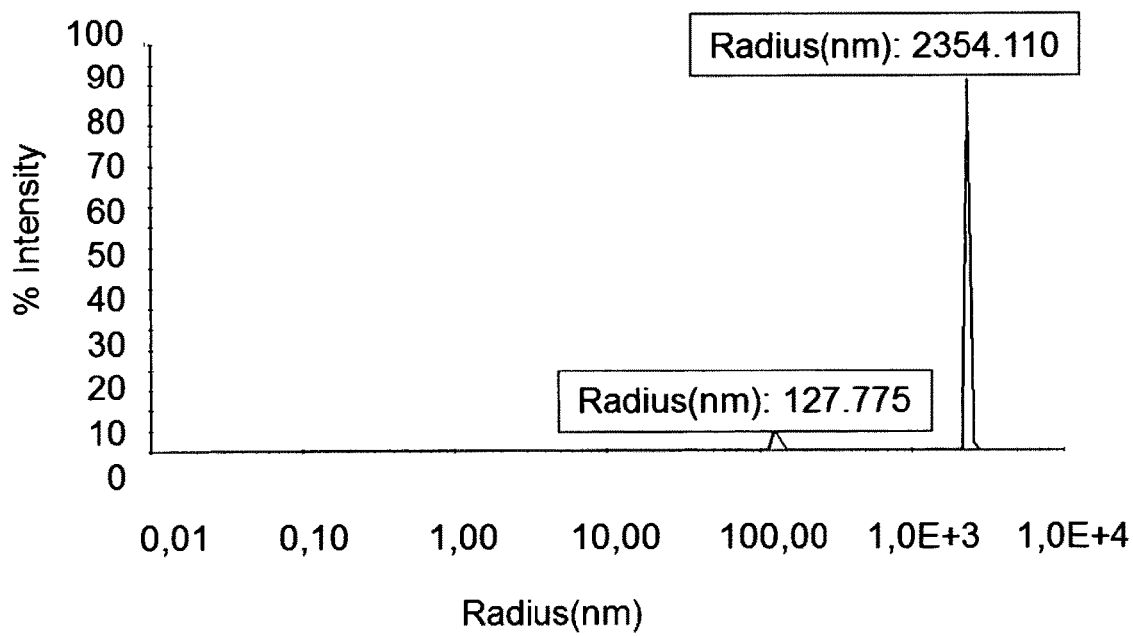

FIG. 13: Dynamic Light Scattering (DLS) Determination of the hydrodynamic radii of the adenoviral particles in stabilizing compositions 1 and 2 during either process step 1 or process step 2 after application of five freeze and thaw cycles as a model for aggregation and polydispersity under stress conditions. Re-buffering of the adenoviral vector particle preparations in composition 1 using dialysis either in process step 1 or 2 resulted in the retention of the hydrodynamic radii of the particles after the application of five freeze and thaw cycles (A) and (B). In contrast, re-buffering of the adenoviral particles in composition 2 either during preparation in process step 1 or 2 led to an increase in the hydrodynamic radii of the particles and the associated formation of higher order aggregates after the application of five freeze and thaw cycles (C) and (D).

Figure 14:
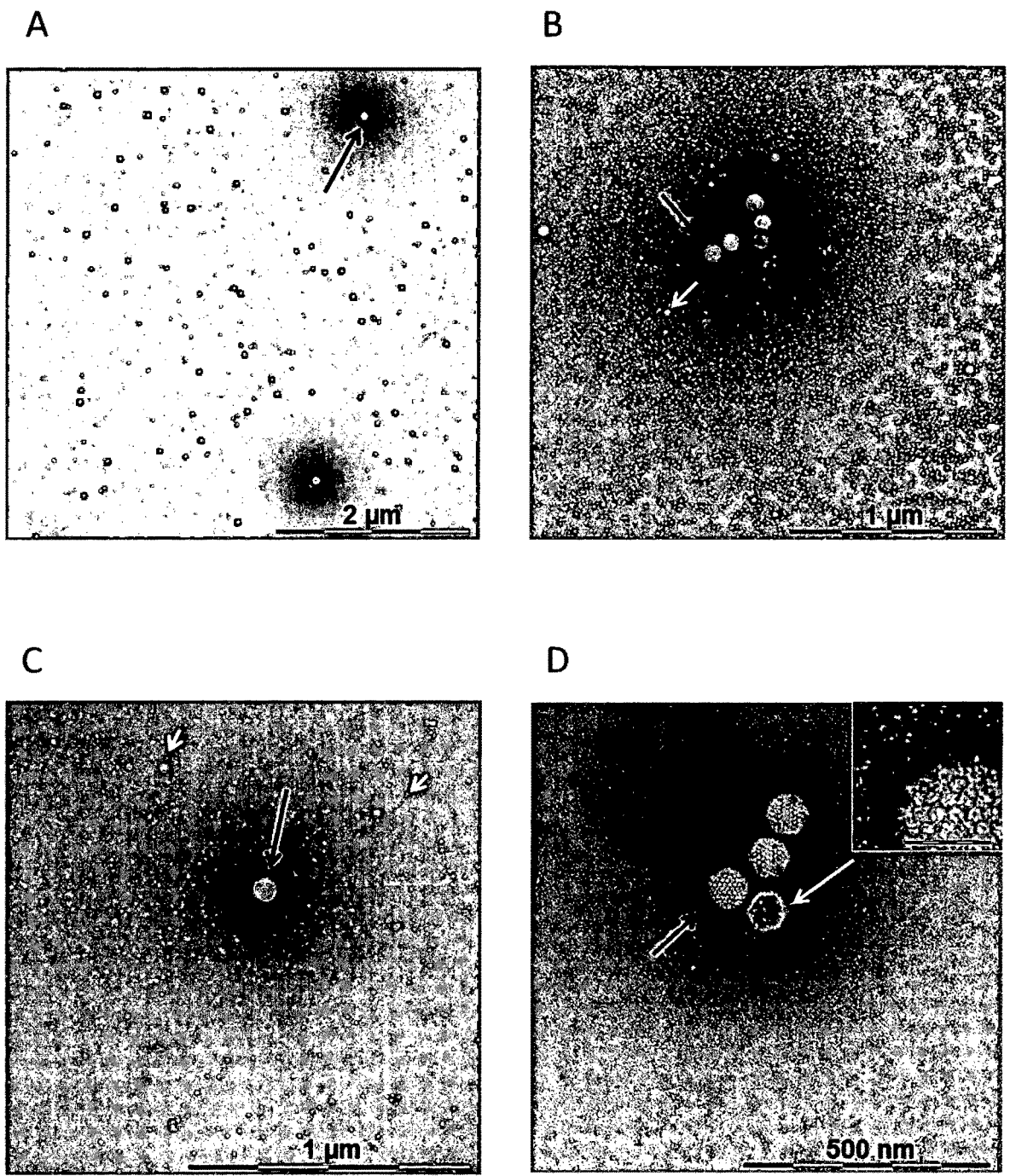

FIG. 14: Transmission Electron Microscopy (TEM) of an adenoviral vector preparation after freeze drying and reconstitution in composition 1. (A) low magnification; (B) intermediate magnification; (C) high magnification; (D) special observation with extra high magnification. Adenovirus particles appeared as icosahedral-shaped bright intact particles (black arrow). A small number of more densely stained less pronounced icosahedral-shape particles (white arrow) were observed, putatively representing partially destabilized virions. Small lightly stained structures (white arrowhead) are present in the background of the grid, but no significant presence of debris or Adenovirus subunits were observed. Adenovirus particles preferentially appeared as single icosahedral-shaped bright intact entities and no aggregation of Adenovirus particles or debris was observed.

Figure 15:
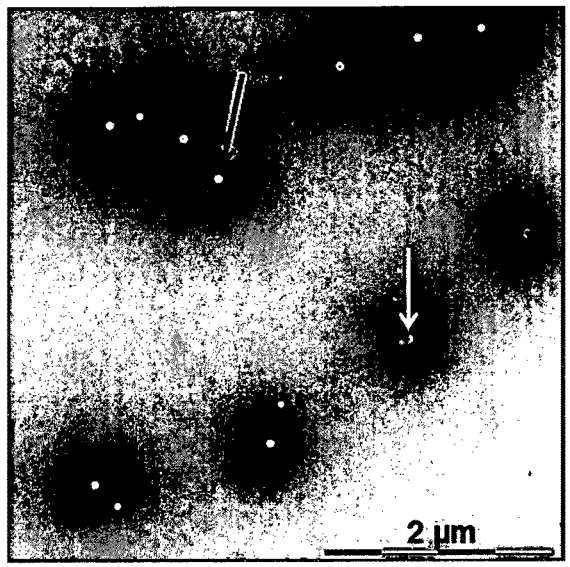
Figure 15:
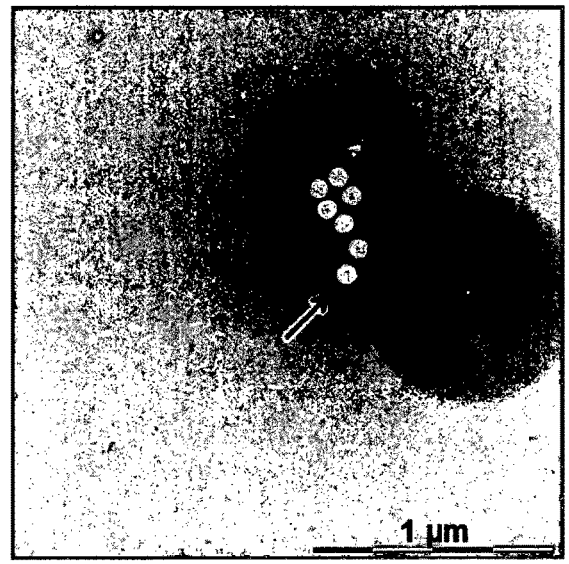
Figure 15:
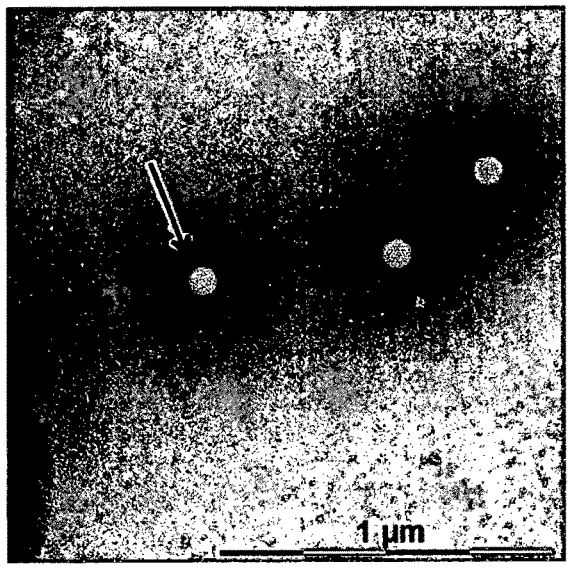
Figure 15:
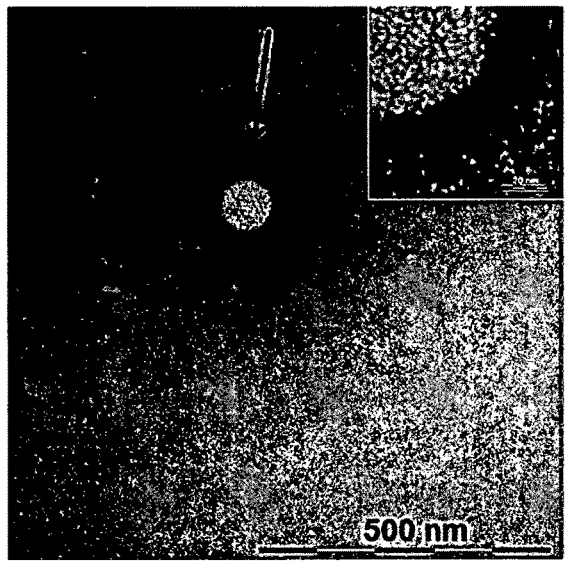

FIG. 15: Transmission Electron Microscopy (TEM) of an adenoviral vector preparation after freeze drying and reconstitution in composition 2. (A) low magnification; (B) intermediate magnification; (C) high magnification; (D) special observation with extra high magnification. Adenovirus particles appeared as icosahedral-shaped bright intact particles (black arrow). The background appeared very smooth with no significant presence of debris or Adenovirus subunits. Adenovirus particles preferentially appeared as single icosahedral-shaped bright intact entities and no aggregation of Adenovirus particles or debris was observed.

Figure 16:
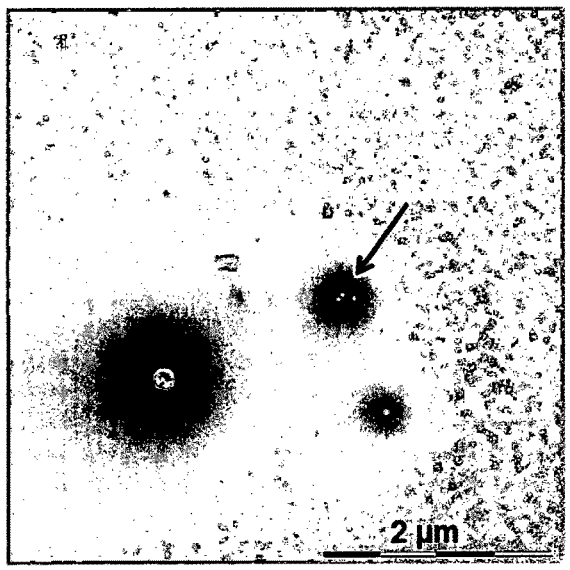
Figure 16:
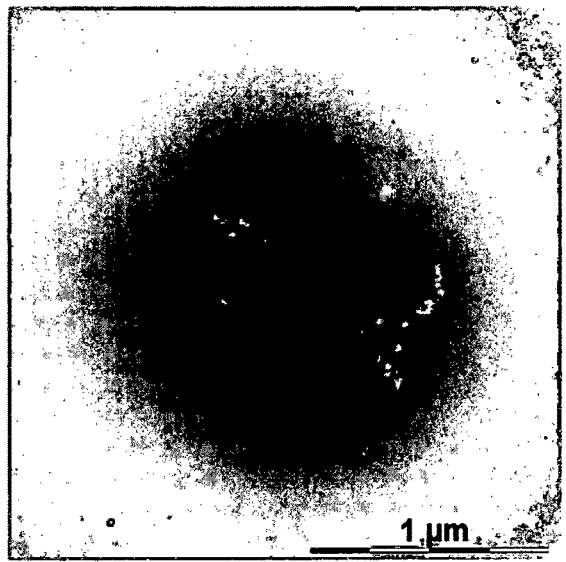
Figure 16:
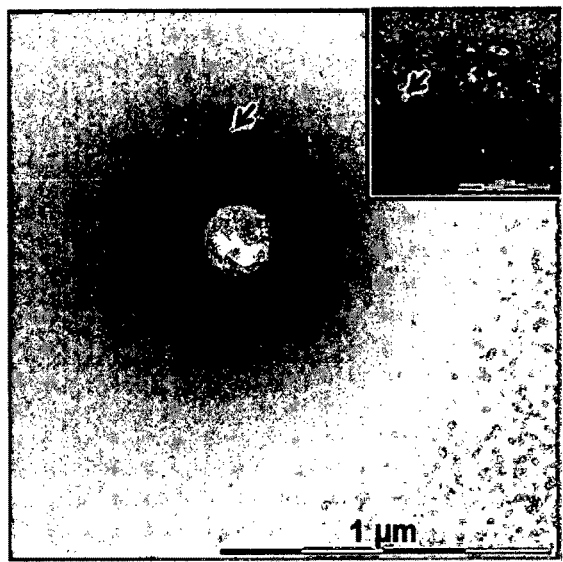
Figure 16:
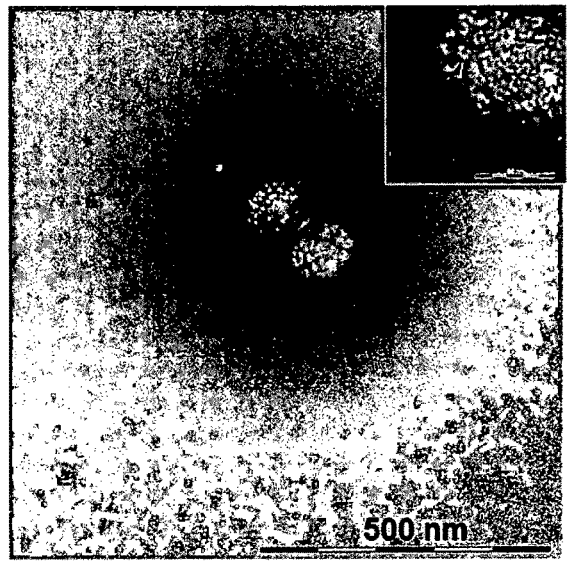

FIG. 16: Transmission Electron Microscopy (TEM) of an adenoviral vector preparation after freeze drying and reconstitution in PBS. (A) low magnification; (B) intermediate magnification; (C) high magnification; (D) special observation with extra high magnification. No intact Adenovirus particles were observed. Small ring-like structures (black arrowhead) possibly representing hexon structures were occasionally observed on the grid (black arrowhead). The hexon structures were both observed as free entities and bound to small clusters of debris (black arrow or to spherical lightly stained structures (D)). A small number of larger aggregates containing debris were observed (B).

Figure 17:
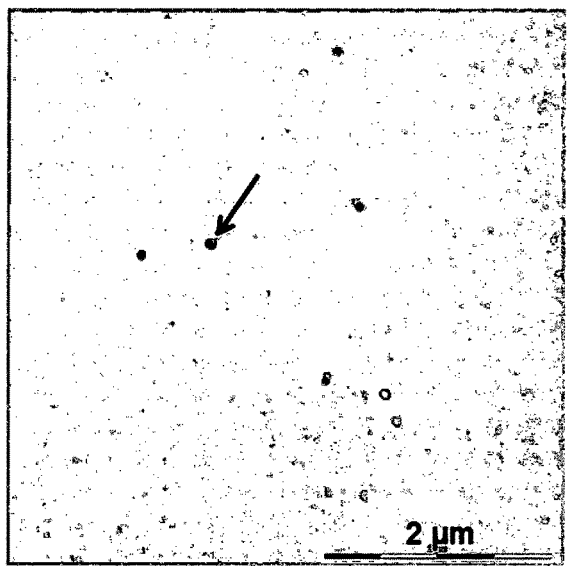
Figure 17:
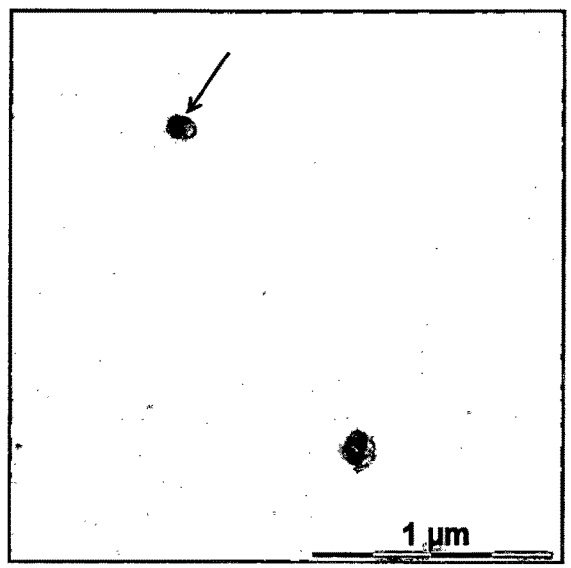
Figure 17:
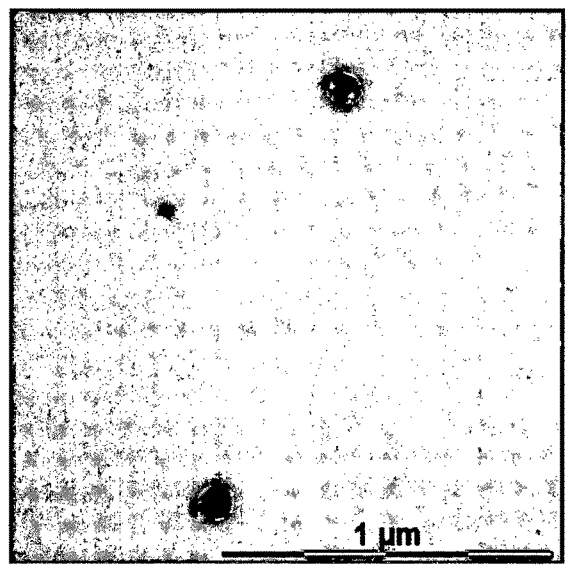
Figure 17:
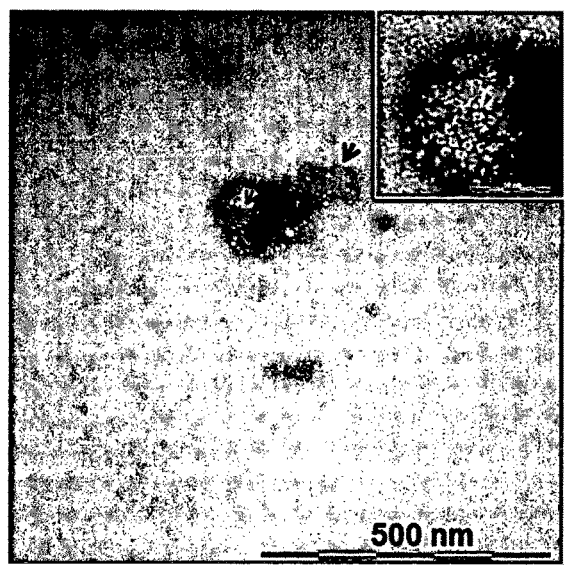

FIG. 17: Transmission Electron Microscopy (TEM) of an adenoviral vector preparation after freeze drying and reconstitution in the original supplier formulation. (A) low magnification; (B) intermediate magnification; (C) high magnification; (D) special observation with extra high magnification. No intact Adenovirus particles were observed. Small ring-like structures (black arrowhead) possibly representing hexon structures were occasionally observed on the grid (black arrowhead). The hexon structures were both observed as free entities and bound to small clusters of debris (black arrow or to spherical lightly stained structures (D)).

Figure 18:
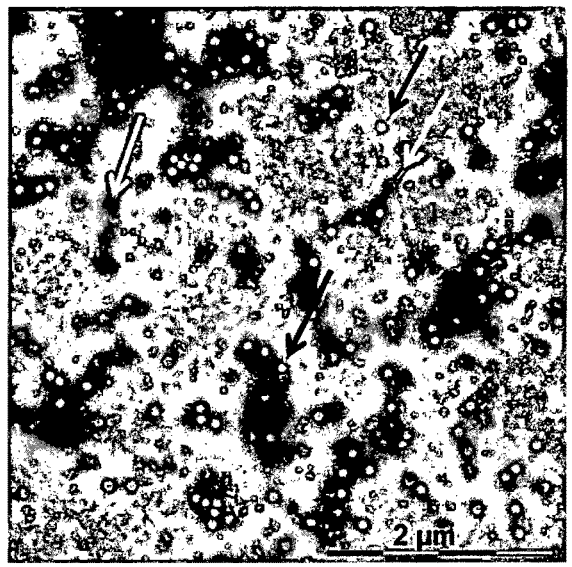
Figure 18:
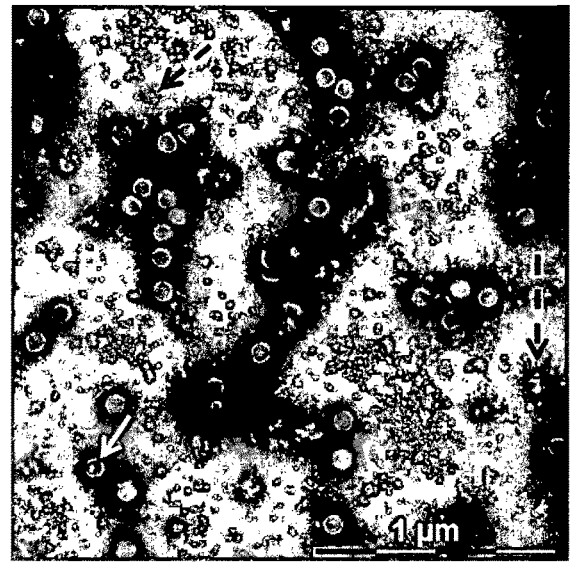
Figure 18:
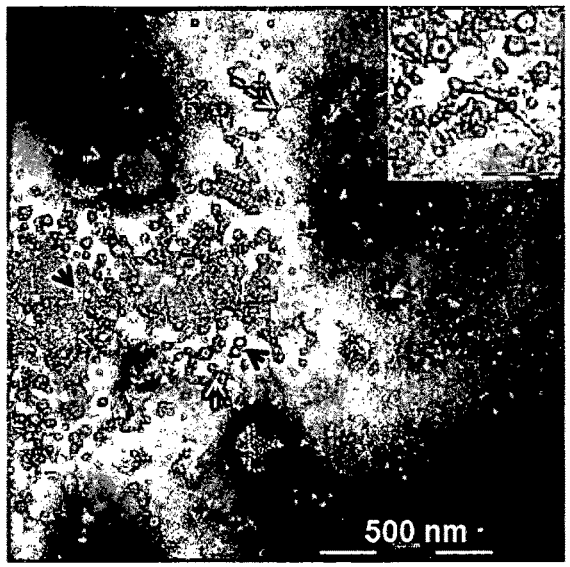
Figure 18:
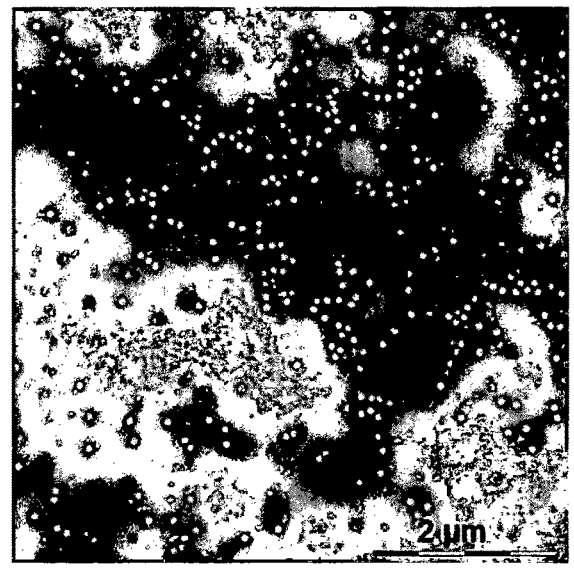

FIG. 18: Transmission Electron Microscopy (TEM) of a adenoviral vector preparation stored at −80° C. in a standard buffer as a positive control. (A) low magnification; (B) intermediate magnification; (C) high magnification; (D) special observation overview image at low magnification. Adenovirus particles were observed, both as icosahedral-shaped bright intact particles (A; black arrow) and densely stained less pronounced icosahedral-shape particles (A, B and C; white arrow), putatively representing partially disassembled particles. The diameter of the Adenovirus particles was measured to approximately 100 nm (vertex-to-vertex). The background shows the presence of debris (B; black dashed arrow), fiber structures (C; white dashed arrow) and small ring-like structures (C; black arrowhead), mainly as single entities and only rarely in clusters, possibly representing hexon structures (C; inset). The Adenovirus particles appeared both as single entities and in smaller clusters. One larger aggregate containing Adenovirus and debris was observed (D).

Figure 19:
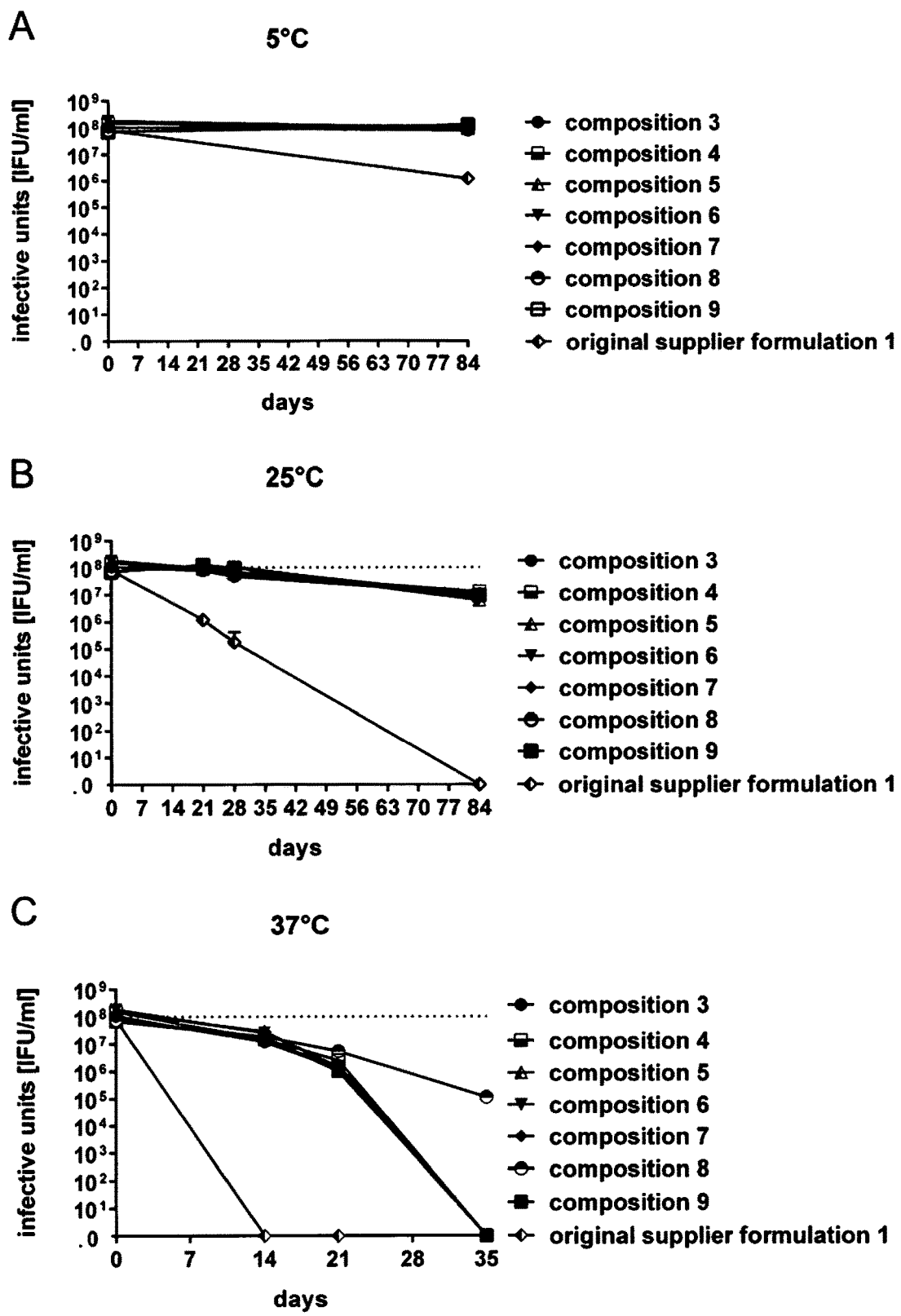
Figure 19:
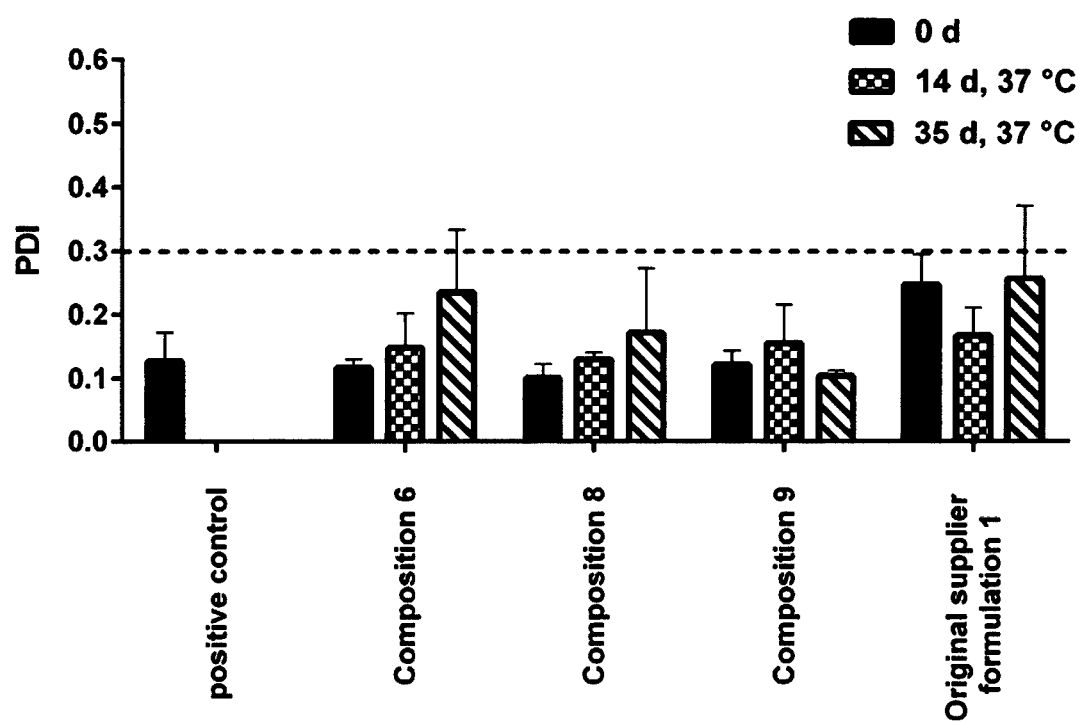

FIG. 19: In vitro infectivity of adenoviral vectors after liquid storage at 5° C., 25° C. and 37° C. in different formulations as a model for functionality under liquid stress conditions. Adenoviral vector preparations were formulated by dilution to $1\times10^8$ IFU/ml in different formulations and subsequently 100 µl were liquid stored in sterile PCR-tubes. After storage at different temperatures an in vitro infectivity assay in HEK 293 cells was carried out using an antibody based colorimetric detection of the adenoviral Hexon protein to indicate a successful amplification of the adenovirus in the infected cells. (A) After 3 months at 5° C. a complete retention of the infective titers of the adenoviral vector preparations formulated in composition 3 to 9 was observed (infective units per ml as compared to positive control; depicted as dashed line). In contrast, the original supplier formulation 1 led to a higher loss of the infective titers of almost 2-log titers. (B) After 3 months liquid storage at 25° C. the infective titers of the adenoviral vector preparations formulated in composition 3 to 9 was decreased to 1-log titer, whereby the original supplier formulation 1 led to a complete loss of the infective titers (infective units per ml as compared to positive control; depicted as dashed line). (C) After 35 days at 37° C. the composition 8 is still detectable with a titer of $1\times10^5$ IFU/ml, whereby in the original supplier formulation 1 the adenoviral vector has no infective units already after 14 days at 37° C. (D) Dynamic Light Scattering (DLS) determination of the PDI values of the adenoviral particles in the corresponding adenoviral vector preparations after liquid storage at 37° C. as a model for increasing particle size distributions expressed in PDI values under liquid storage stress conditions.

Figure 20:
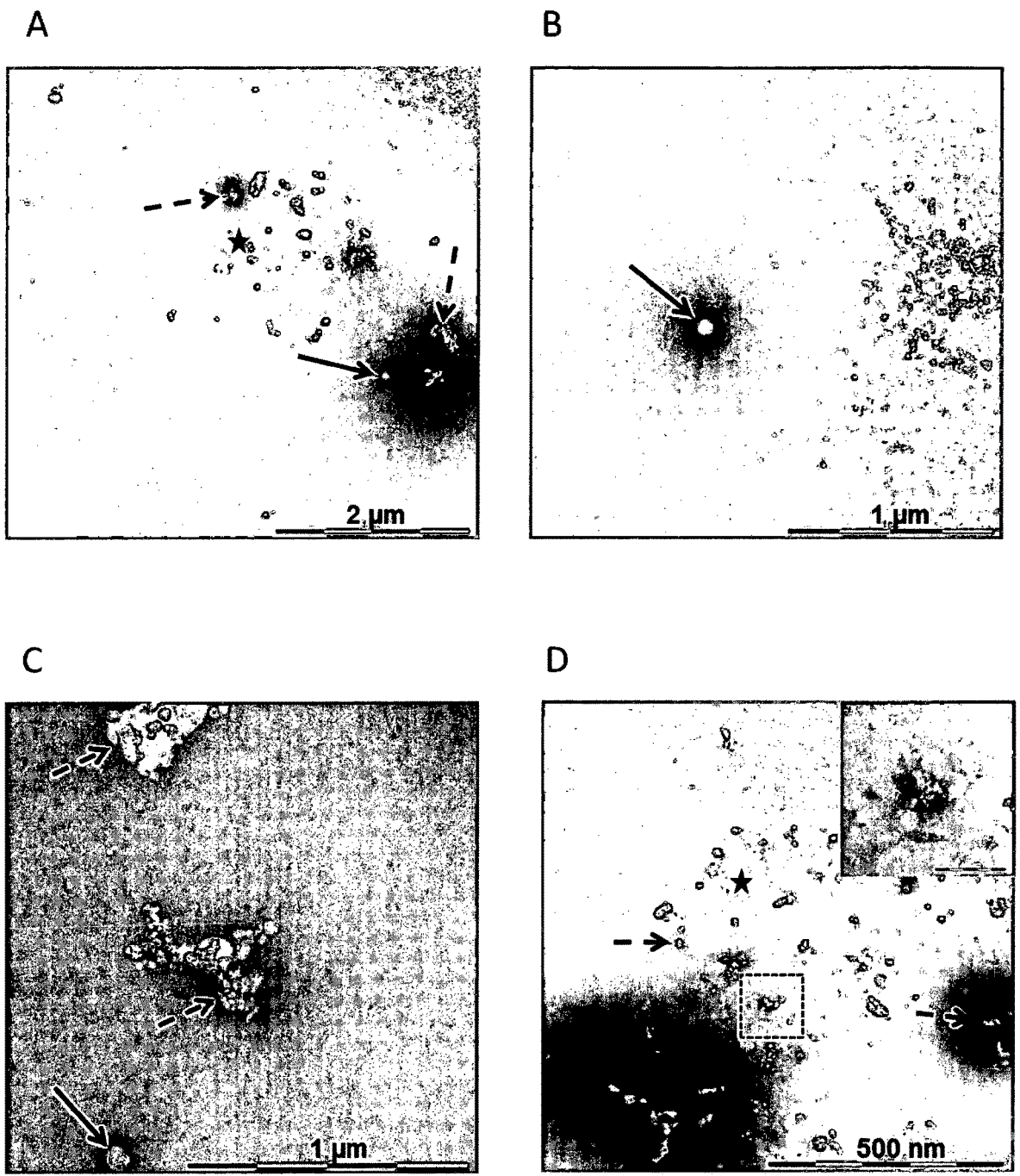

FIG. 20: Transmission Electron Microscopy (TEM) of an adenoviral vector preparation formulated in composition 8 after liquid storage for 28 days at 25° C. (A) low magnification; (B) intermediate magnification; (C) high magnification; (D) special observation overview image at low magnification. Adenovirus particles were observed, both as icosahedral-shaped bright intact particles and densely stained less pronounced icosahedral-shape particles and, putatively representing partially disassembled particles. The diameter of the Adenovirus particles was measured to approximately 100 nm (vertex-to-vertex). The background shows the presence of debris, fiber structures and small ring-like structures, mainly as single entities and only rarely in clusters, possibly representing hexon structure).

Figure 21:
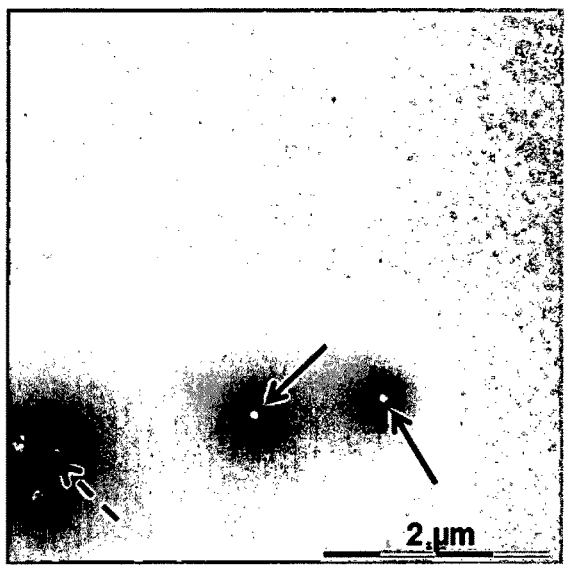
Figure 21:
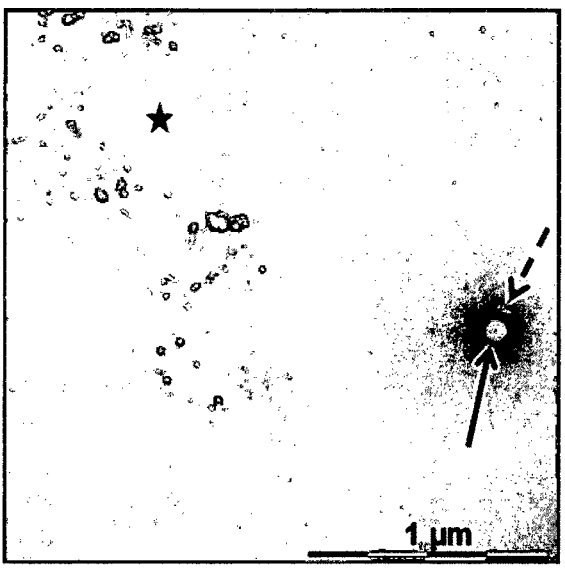
Figure 21:
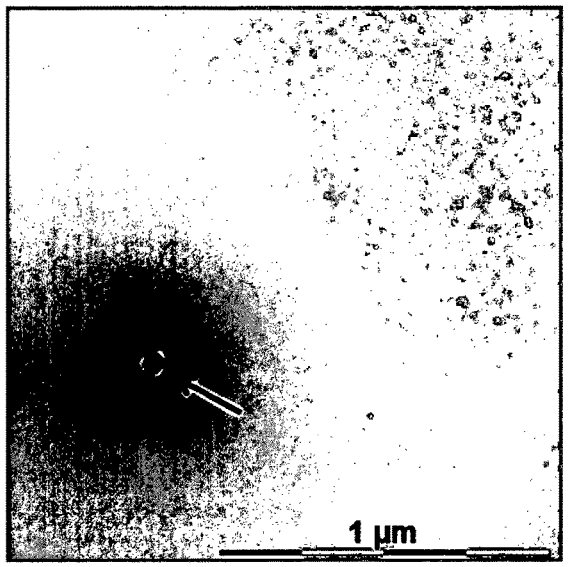
Figure 21:
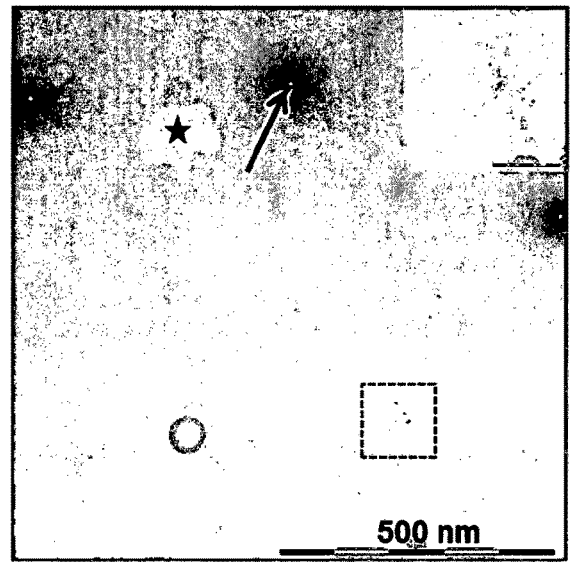

FIG. 21: Transmission Electron Microscopy (TEM) of an adenoviral vector preparation formulated in composition 6 after liquid storage for 28 days at 25° C. (A) low magnification; (B) intermediate magnification; (C) high magnification; (D) special observation overview image at low magnification. Adenovirus particles were observed, both as icosahedral-shaped bright intact particles and densely stained less pronounced icosahedral-shape particles and, putatively representing partially disassembled particles. The diameter of the Adenovirus particles was measured to approximately 100 nm (vertex-to-vertex). The background shows the presence of debris, fiber structures and small ring-like structures, mainly as single entities and only rarely in clusters, possibly representing hexon structure).

Figure 22:
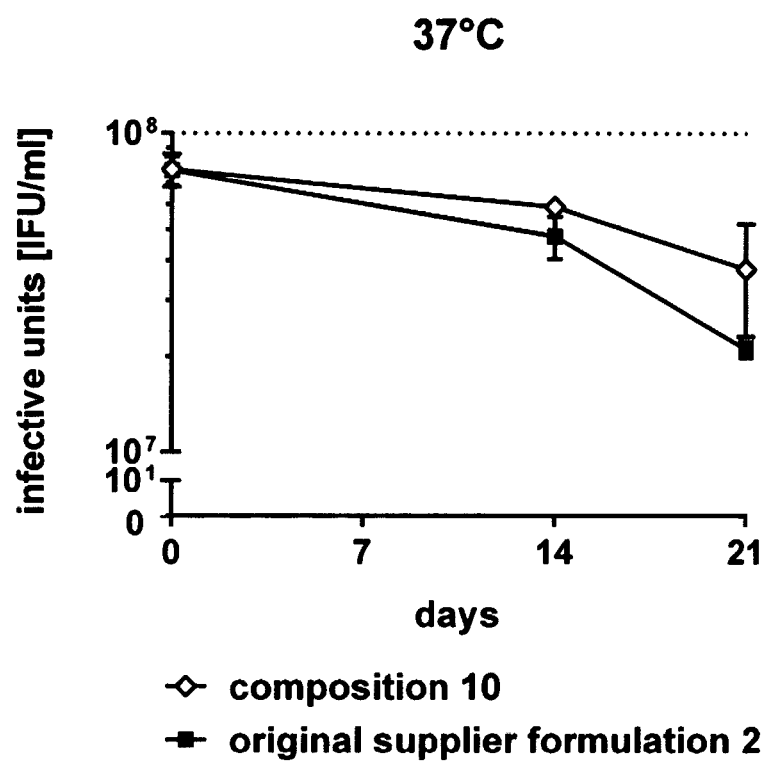

FIG. 22: In vitro infectivity of adenoviral vectors after liquid storage at 37° C. in composition 10 as a model for functionality under liquid stress conditions. The adenoviral vector preparation in composition 10 showed a better retention of the infective titre after liquid storage for 14 days and more pronounced for 21 days at 37° C. than the corresponding preparation in the original supplier formulation 2.

Figure 23:
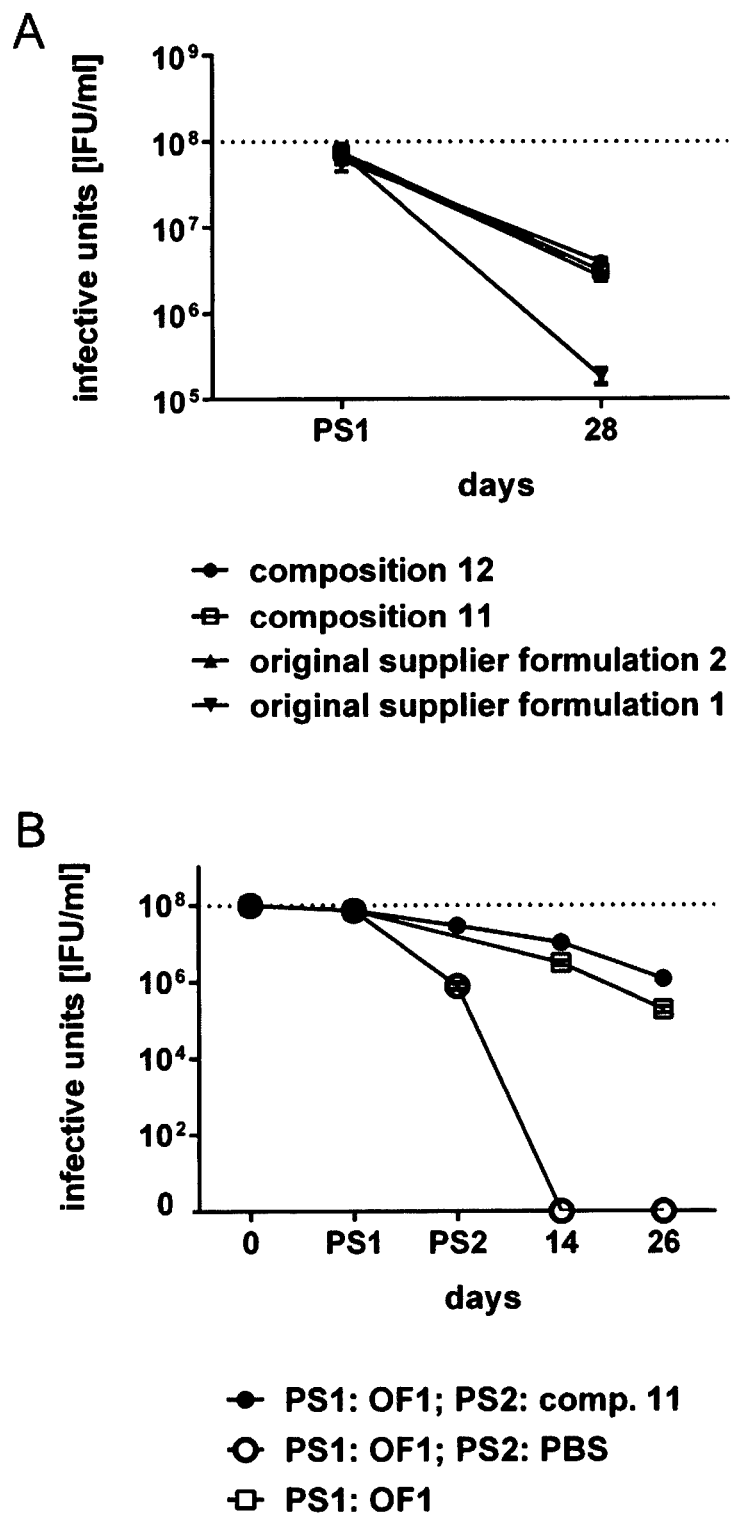

FIG. 23: In vitro infectivity of adenoviral vectors after liquid storage at 37° C. in composition 11 and 12 or in original supplier formulations 1 and 2 prepared by processing step 1 and 2 (PS1 and PS2) as a model for functionality during different processing steps. The adenoviral vector preparation in composition 11 and 12 (A) showed a better retention of the infective titre after liquid storage for 28 days at 37° C. than the corresponding preparation in the original supplier formulations 1 and 2. The adenoviral vector preparations formulated in composition 11 using preparation step 2 showed a remarkable stabilization during storage for 28 days at 37° C. compared to PBS (B; loss of infectivity already after 14 days).

Figure 24:
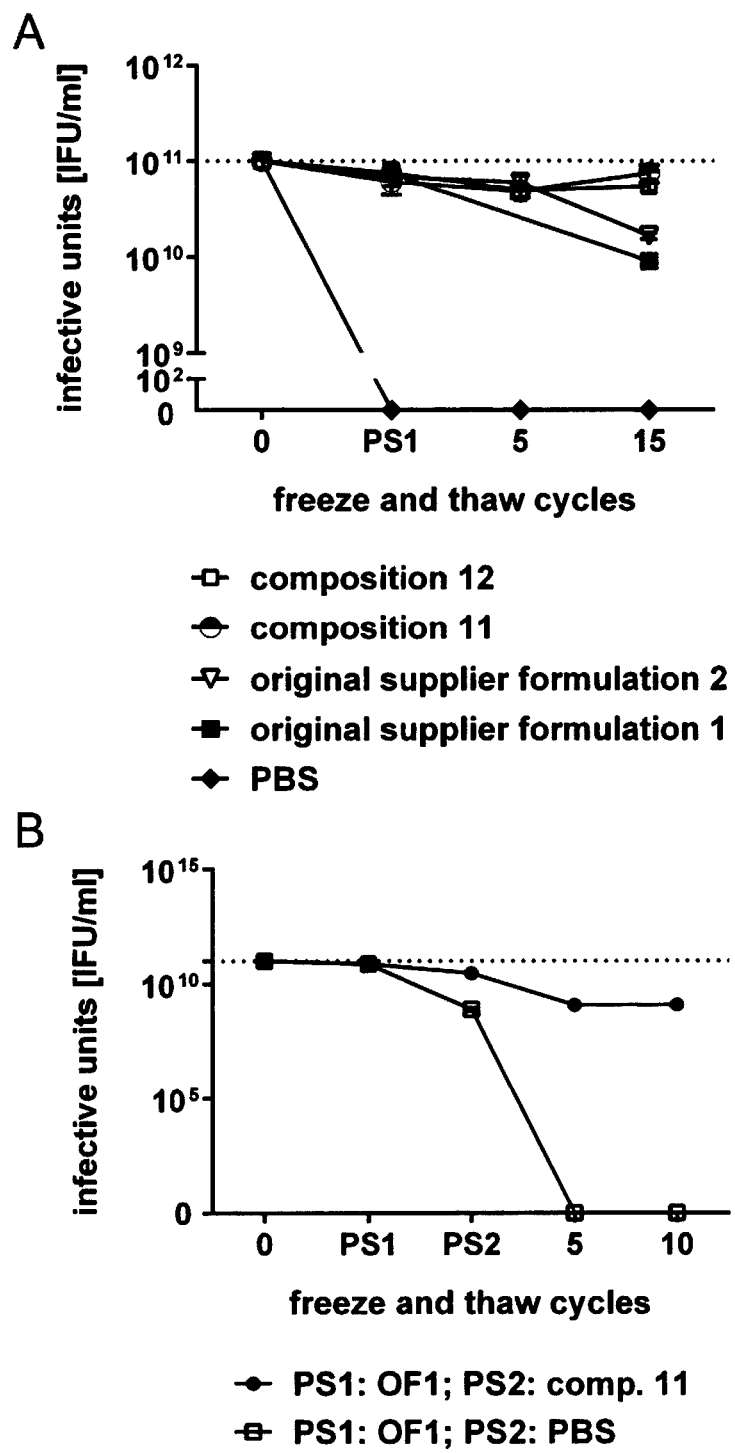

FIG. 24: In vitro infectivity of adenoviral vectors after application of different freeze-thaw cycles in compositions 11 and 12 after formulation according to PS1 and PS2 compared to the original supplier formulations 1 and 2 and PBS. The adenoviral vector preparation in composition 11 and 12 (A) showed a better retention of the infective titre after application of 5 freeze-thaw cycles, and more pronounced after 15 freeze-thaw cycles compared to the original supplier formulations 1 and 2 and PBS. The adenoviral vector preparation formulated in composition 11 using preparation step 2 (PS2) showed a better retention of the infectivity after the application of 10 freeze-thaw cycles compared to PBS.

Figure 25:
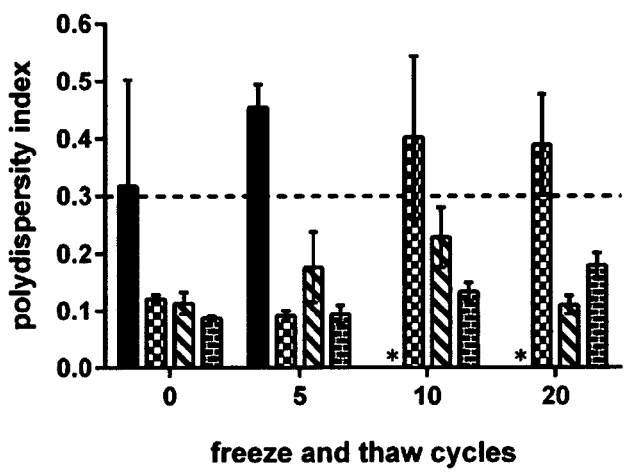
Figure 25:
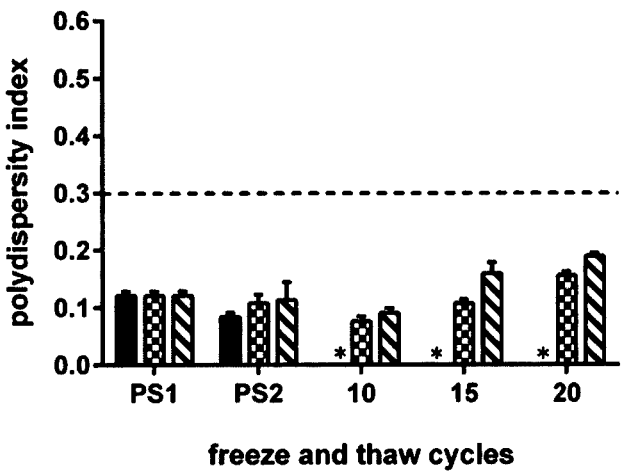

FIG. 25: Dynamic Light Scattering (DLS) determination of the PDI values of the adenoviral particles in the corresponding adenoviral vector preparations after the application of several freeze-thaw cycles as a model for increasing particle size distributions expressed in PDI values under different processing conditions. The PDI values of the adenoviral vector compositions formulated in compositions 11 and 12 according to PS1 were lower than 0.3 even after twenty freeze-thaw cycles (A). Formulation of the adenoviral vector samples in compositions 11 and 12 according to PS2 resulted in retention of PDI values smaller than 0.3 (B).

Figure 26:
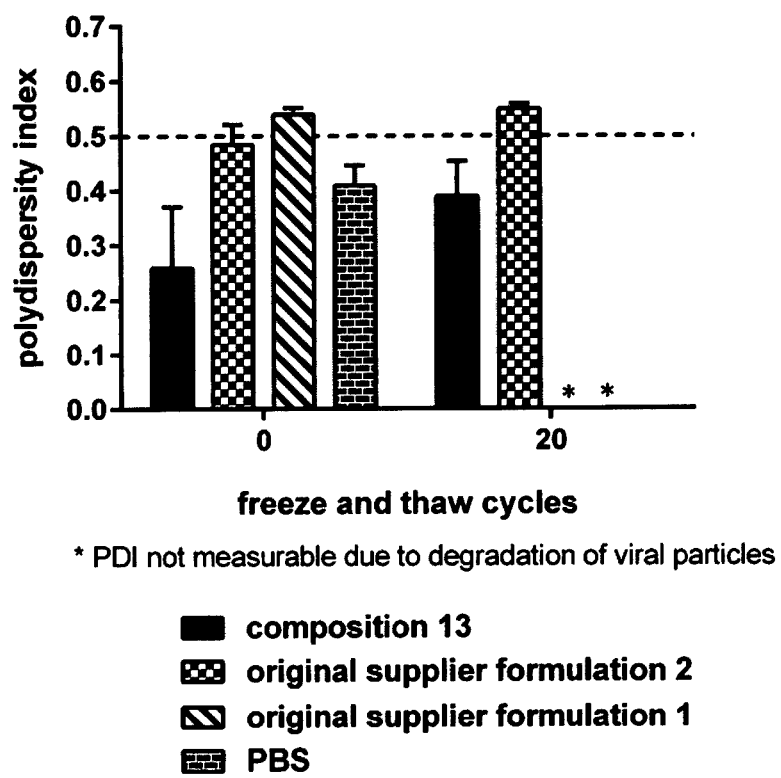

FIG. 26: Dynamic Light Scattering (DLS) determination of the PDI values of the MVA particles in composition 13. After application of 20 freeze-thaw cycles, the PDI values of MVA in composition 13 were smaller than 0.5 compared to original supplier formulations 1 and 2 and PBS.

The examples illustrate the invention:

EXAMPLE 1

The in vitro study of the functional and structural integrity of freeze-dried and subsequently stored adenoviral vectors showed that a composition comprising amino acids and sugar stabilizes the viral vectors during freeze drying 1.1 Materials and Methods Composition 1 and 2 contained the 7 amino acids alanine, arginine, glycine, glutamic acid, lysine, histidine and tryptophan in a concentration corresponding to the sum of the amino acids of 40 g/l. But in composition 1, a 5 fold increase of the tryptophan concentration and a 1.667 fold increase of the histidine and glutamic acid concentration under reduction of the concentrations of the other amino acids arginine, glycine, lysine and the retention of the alanine concentration compared to composition 2 resulted in the same concentration according to the sum of amino acids of 40 g/l. Further, an additional surfactant polysorbate 80 in a concentration of 0.05 g/l was added to composition 1 in contrast to composition 2. Both compositions contained trehalose as the corresponding sugar in an amino acid to trehalose ratio of 1:2. The pH value was adjusted in all compositions to 7.

An adenoviral stock solution stored at −80° C. with a concentration of $7.5*10^{10}$ IFU/ml in the original supplier formulation (Firma Sirion; Martinsried/Munich; Germany) was employed.

1.1.1 Sample Preparation and Freeze Drying

The adenoviral vector stock solution was re-buffered by dilution of the stock solution to a concentration of $1*10^8$ IFU/ml with either composition 1 or composition 2. For comparison the stock solution was diluted with either the original supplier formulation or with PBS to the same concentrations.

In order to prepare the samples for freeze drying, the different adenoviral formulations were aliquoted in volumes of 500 μl in 2R freeze drying vials (Schott A G; Mainz; Germany) and subsequently freeze-dried using the following drying parameters:

| Protocol Step | Target T (° C.) | Slope (h) | Hold (h) | Pressure (mbar) |
| --- | --- | --- | --- | --- |
| Introduction | 20 | 0 | 0 | 1000 |
| Freezing | −50 | 2:00 | 2:00 | 1000 |
| Sublimation | −50 | 0:01 | 0:30 | 0.045 |
|  | −35 | 3:00 | 30:00 | 0.045 |
| Secondary Drying | 20 | 3:00 | 7:00 | 0.009 |

After freeze drying, the samples were visually inspected and one part of the samples was stored for a short time at 2-8° C. until analysis of the initial infective titer at the time point t=0. The other part of the samples was stored according to the guidelines of the International Council for Harmonization (ICH) for 21 or 42 days at 25° C. under environmental conditions of 60% residual humidity, or for 7 or 28 days at 40° C. under environmental conditions of 75% residual humidity.

1.1.2 Determination of the Infective Titers for Adenoviral Vectors in Cell Culture In order to analyze the infective titer of the adenoviral vector formulations, an antibody based virus titration experiment in HEK 293 cell culture using the detection of the adenoviral Hexon protein after successful amplification of the adenovirus in the infected cells was applied. $2.5*10^5$ HEK 293 (CCS) cells (Firma Sirion; Martinsried/Munich; Germany) were seeded per well of a 24-well micro titer plate in a volume of 500 µl. The adenoviral vector formulations were reconstituted either directly after freeze drying or at the indicated time points upon storage at 25° C. and at 40° C. As a positive control an aliquot of the adenoviral stock solution stored at −80° C. with a concentration of $7.5*10^{10}$ IFU/ml in the original supplier formulation (Firma Sirion; Martinsried/ Munich; Germany) was used. Subsequently, serial dilutions of the adenoviral samples were prepared and 50 µl of the resulting dilutions per well were used for infection of the cells. The plates were incubated for 42 hours at 37° C. After infection, cells were fixed with methanol, incubated with the primary anti-Hexon protein antibody (Santa Cruz Biotechnology, Inc.; Dallas; Texas: USA), subsequently incubated with an horse radish peroxidase (HRP)-conjugated secondary anti-mouse antibody (Cell Signaling Technology; Danvers; Massachusetts; USA) specific for the primary antibody and an HRP enzymatic reaction with diaminobenzidine (Carl Roth GmbH and Co.KG; Grafrath; Germany) was carried out, wherein a brown colouring indicates infected cells. The number of infected cells was quantified by counting the brown coloured cells under the microscope, wherein each infected cell is counted as one infectious viral particle.

1.1.3 Dynamic Light Scattering (DLS) Measurement

DLS was carried out on samples taken before freeze drying directly after re-buffering compared to an untreated positive control corresponding to an aliquot of the adenoviral stock solution stored at −80° C. as well as on samples after reconstitution of the adenoviral vector formulations. In the latter case, DLS was carried out either immediately after freeze drying (t=0) or at the relevant time points upon storage at 25° C. (21 days, 42 days) and at 40° C. (7 days, 28 days).

To this end, 5 µl of the samples were pipetted into a special DLS cuvette and analysed in a DynaPro Nanostar DLS instrument (Wyatt Technology Europe GmbH; Dernbach; Germany). For each experimental formulation, a blank measurement was performed under the same conditions. The DLS measurements were performed with acquisition times between 20 and 40 seconds in 10 or 20 cycles. The resulting correlation curves were analysed using the DynaPro DLS software.

1.1.4 Transmissional Electron Microscopy

Adenoviral vector preparations were formulated by dilution and subsequently freeze-dried in composition 1 and 2 as well as in original supplier formulation and PBS. The EM images were acquired by Vironova (Sweden). After reconstitution of the freeze-dried vectors 3 µl of the sample were applied onto a suitable hydrophilized EM grid (e.g. continuous carbon) washed with water, and negatively stained using 2% uranyl acetate. The grids were imaged using a FEI Tecnai G2 Spirit Biotwin electron microscope run at 100 kV accelerating voltage. Both low and high magnification images were acquired in representative areas. In the case of the positive control 3 µl of the undiluted frozen stored sample (−80° C.) in the original supplier formulation buffer were applied onto the grid.

1.2 Results

Interestingly, the evaluation of the correlation functions recorded in the DLS experiments directly after mixing of the adenoviral vector preparations with the solutions according to the invention (composition 1 or composition 2) suggested a complete retention of the hydrodynamic radii of the adenoviral vectors (FIGS. 1B and C) as compared to those of the untreated adenoviral particles in the original stock solution (FIG. 1A). Similar mixing of the adenoviral stock solution by dilution with the original supplier formulation or with PBS during the preparation process of the samples before freeze drying already led to a remarkable increase in the measured hydrodynamic radii of the adenoviral vectors (FIGS. 2A and B) compared to the untreated adenoviral vector (FIG. 1A).

The in vitro infectivity assay after freeze drying revealed that a formulation of adenoviral vector preparations in the stabilizing compositions 1 and 2 early in the production process of a freeze-dried biopharmaceutical product resulted in infective titers that correspond to those of the positive control depicted as dashed line in FIG. 1. Thus, a complete retention of infective titers was observed after freeze drying. In contrast, when the adenoviral vectors re-buffered in the original supplier formulation were freeze-dried, a remarkable loss of the infective titers was observed and freeze drying in PBS even resulted in a complete loss of the corresponding infective titers (FIG. 3).

The in vitro infectivity results of the adenoviral preparations after reconstitution of the dried products were well in line with the results of the parallel determination of the hydrodynamic radii by Dynamic Light Scattering experiments. The combination of adenoviral vector preparation with the composition 1 and 2 according to the present invention already during early phase downscaling steps and subsequent freeze drying resulted in the complete retention of the hydrodynamic radii of the viral particles (Example 1; FIGS. 4A and B). In contrast, freeze drying of the corresponding adenoviral vector preparations in the original supplier formulation resulted in increased particle sizes (Example 1; FIG. 5A). The similar sample preparation procedure in combination with the common phosphate-buffered saline (PBS) resulted in massive increase in particle size (Example 1 FIG. 5B) and the formation of significant amounts of higher order aggregates, already after freeze drying.

These differences were even more striking after storage of the freeze-dried preparations. A complete loss of function of the viral vectors freeze-dried in the original supplier formulation (FIG. 6) was observed, similar to the results obtained in PBS. In contrast, even after storage at 25° C. or even at 40° C., the freeze-dried adenoviral vector compositions that were formulated in the stabilizing compositions 1 and 2 early during the production process retained almost the same viral activity as the positive control, i.e. the adenoviral vector prior to being freeze-dried (depicted as dashed line in the diagram of FIG. 6).

These results of the in vitro infectivity experiments correspond well with the DLS experiments performed in parallel. As examples, the evaluation of the recorded DLS correlation function after storage of the dried adenoviral vector compositions either in the composition 1 and 2 according to the invention or in the original supplier formulation and PBS, respectively after storage for 14 days at 40° C. were depicted in FIGS. 7 and 8. The storage of the dried adenoviral vector preparations in stabilizing composition 1 and 2 led to retention of the determined hydrodynamic radii of the adenoviral particles (Example 1; FIGS. 7A and 7B) in contrast to the stored adenoviral particles in the original supplier formulation and in PBS (Example 1; FIGS. 8A and 8B).

The freeze-dried adenovirus preparations were reconstituted and were further characterized using electron microscopic analysis. This analysis further substantiated that a combination of the adenoviral vectors with the recited at least three excipients and sugar at a ratio of at least 1:2, in accordance with the invention, provides superior stability for the dried adenoviral vector formulations and also confirmed the above detailed infectivity and DLS results.

The electron microscopic images of the corresponding adenoviral preparations in composition 1 and 2 (FIGS. 14 and 15) show relatively evenly distributed Adenovirus particles, with the majority of the Adenovirus particles appearing as icosahedral-shaped bright intact particles (black arrow) of approximately 100 nm diameter. A small number of more densely stained, less pronounced icosahedral-shaped particles was observed (white arrow), which presumably represent partially destabilized virions. Small, lightly stained structures (white arrowhead) are present in the background of the grid, but no significant presence of debris or Adenovirus subunits was observed in composition 1 (FIGS. 14B and 14C). For composition 2, the background appeared very smooth with no significant presence of debris or Adenovirus subunits (FIG. 15). In the Adenovirus preparations formulated in composition 1 and 2, the Adenovirus particles preferentially appeared as single icosahedral-shaped bright intact entities and no aggregation of Adenovirus particles or debris was observed. In contrast, the analysis of the adenoviral vectors after freeze drying in the original supplier formulation (FIG. 17) and in PBS (FIG. 16) showed that no intact Adenovirus particles were observed. Small ring-like structures (black arrowhead), possibly representing hexon structures, were occasionally observed on the grid (black arrowhead FIGS. 16C and 17D), both as free entities and bound to small clusters of debris (black arrow FIGS. 16A and 17A and B) or to spherical lightly stained structures (FIGS. 16D and 17D). In the corresponding adenoviral preparation in PBS a small number of larger aggregates containing debris was observed (FIG. 16B).

For comparison, FIG. 18 shows the electron microscopic analysis of the remarkable higher concentrated positive control stored at −80° C. in a standard buffer. Adenovirus particles were observed, both as icosahedral-shaped bright intact particles (FIG. 18A; black arrow) and densely stained less pronounced icosahedral-shape particles (FIGS. 18A, B and C; white arrow), putatively representing partially disassembled particles. The diameter of the Adenovirus particles was measured to approximately 100 nm (vertex-to-vertex). The background shows the presence of debris (FIG. 14B; black dashed arrow), fiber structures (FIG. 18C; white dashed arrow) and small ring-like structures (FIG. 18C; black arrowhead), mainly as single entities and only rarely in clusters, possibly representing hexon structures (FIG. 18C; inset). The Adenovirus particles appeared both as single entities and in smaller clusters. One larger aggregate containing Adenovirus and debris was observed (FIG. 18D). It should be noted that the positive control was measured with the adenoviral composition in a standard buffer stored at −80° C. containing an infective titer of $2*10^{11}$ IU/ml. In contrast, the infective titer of the freeze-dried and reconstituted adenoviral preparations according to the EM images in FIGS. 14 to 17 was around $1*10^{8}$ IU/ml.

EXAMPLE 2: The In Vitro Study of the Functional and Structural Integrity of Different Adenoviral Vector Preparations after Freeze and Thaw Stress Showed that a Composition Comprising Amino Acids and Sugar Stabilizes the Viral Vectors During Freeze and Thaw Cycles 2.1 Materials and Methods
2.1.1 Sample Preparation and Further Processing High titers of adenoviral vector stocks of the adenoviral type 5 vectors containing the coding DNA for the eGFP protein $5*10^{8}$ HEK293 cells were transduced with adenoviral particles. 48 h after transduction, the cells were harvested and the release of viral particles was performed via Na-Deoxycholat and DNase I treatment. Viral particles were purified by CsCl gradient ultracentrifugation usually followed by buffer exchange in the original supplier formulation on PD10 columns and subsequent determination of the infective titer. The resulting high titer adenoviral stocks were subsequently aliquoted and stored at −80° C.

Sample preparation—process step 1: Adenoviral vector formulations were prepared by re-buffering of the adenoviral vector preparations immediately after CsCl gradient ultracentrifugation. The obtained adenoviral vector band was harvested and dialysed at 2-8° C. in either composition 1 or 2 (as described in 1.1). The resulting formulations were aliquoted and stored at −80° C.

Sample preparation—process step 2: Frozen (−80° C.) adenoviral stock solutions ($7.5*10^{10}$ IFU/ml; Sirion, Martinsried/Munich, Germany) were thawed (room temperature; RT) in the original supplier buffer and subsequently dialysed at 2-8° C. in compositions 1 and 2.

2.1.2 Repeated Freeze and Thaw Cycles with Adenoviral Samples from Process Step 1 and Step 2 Preparations In order to analyze the stability of the adenoviral vector preparations during subsequent stress conditions, 50 µl of the adenoviral vectors, formulated in composition 1 or 2 were subjected to repeated freeze (−80° C.) and thaw (RT) cycles. The in vitro infectivity (described in 1.1.2) was determined at the initial time point t=0 and after 5 and 10 freeze thaw cycles by virus titration in HEK 293 cell cultures (described in 1.1.2). In parallel, the hydrodynamic radii of the adenoviral particles were measured by DLS (described in 1.1.3).

2.2 Results

The in vitro infectivity assay revealed that composition 1 fully retained the infective titers of both adenoviral vector preparations from process step 1 and step 2 (FIG. 9) compared to the positive control (dashed line in FIG. 9). Re-buffering of the adenoviral vector preparations immediately after the ultracentrifugation step (process step 1) in composition 2 also fully retained the infectivity of the adenoviral vector preparation. Interestingly, composition 2 used after process step 2, resulted in a loss of approximately two log levels of the initial titer (FIG. 9).

Upon additional freeze and thaw cycles (five and ten), composition 1 retained the full infective titer, regardless of the production process step and time point of re-buffering (FIGS. 11A and B). In contrast, composition 2 resulted in remarkably different effects when prepared in the two different process steps 1 and 2. The infective titers of composition 2 samples obtained according to process step 2 significantly further decreased after five and even stronger after ten freeze and thaw cycles (FIG. 11B). When the adenoviral vectors were formulated at the earlier process step 1 in composition 2, only a minor titer loss was observed after five freeze and thaw cycles. Ten freeze and thaw cycles resulted in a stronger decrease but to a minor extent compared to the preparation in process step 2 (FIG. 11A). In parallel to the determination of the infective titers before and after repeated freeze and thaw cycles, the hydrodynamic radii of the corresponding adenoviral particles were analyzed using Dynamic Light Scattering (DLS) (FIGS. 10, 12 and 13). Re-buffering of the adenoviral vector preparation directly after the purification step using ultracentrifugation (preparation step 1) resulted in the complete retention of the hydrodynamic radii of the viral particles in both compositions (FIGS. 10A and 10B) confirming the complete retention of the corresponding in vitro infectivity (FIG. 9). In the case of composition 1, after re-buffering the adenoviral vector preparation according to process step 2 a slight increase of the hydrodynamic particle radii was observed (FIG. 10C) which is in accordance with the infectivity results shown in FIG. 9. In contrast, re-buffering of the adenoviral vector preparation in composition 2 corresponding to processing step 2 resulted in a remarkable increase of the hydrodynamic radius of the adenoviral particles (FIG. 10D) accompanied by the formation of higher order aggregates that may explain the loss of function in the in vitro infectivity tests (FIG. 9).

After five and ten repeated freeze and thaw cycles, changes in the hydrodynamic radii of viral particles, particularly in composition 2 were measured by DLS. No remarkable increase was observed in composition 1 when prepared during process steps 1 and 2. As an example the DLS results for the size of the adenoviral particles in composition 1 after the application of five and ten freeze and thaw cycles are depicted in FIG. 12. When composition 2 was used during process step 1 the hydrodynamic radii already after five freeze and thaw cycles were remarkably increased in conjunction with the formation of higher order aggregates and were not measurable after ten freeze and thaw cycles and when used in process step 2 due to further increased radii and higher order aggregates which were outside the DSL measure limit (FIGS. 13C and D). The behavior of the adenoviral particle size in composition 1 and 2 prepared either during process step 1 and 2 after the application of five freeze and thaw cycle is depicted in FIG. 13A to D).

In summary and conclusion, composition 1 generally exhibited excellent stabilizing efficacy for the adenoviral vector particles during both applied early production steps. In contrast, although composition 2 showed stabilizing efficacy when used directly after ultracentrifugation, reduced stabilizing efficacy was observed when used later in the production process as compared to composition 1.

The DLS data correlate with the in vitro infectivity data shown in example 1. This leads to the conclusion that the use of specifically tailored stabilizing compositions based on amino acids early in the production process of viral vector compositions is important for the stability during further processing steps in biopharmaceutical manufacturing. Moreover, the stabilization of viral vector based compositions in terms of the decrease of the polydispersity of the solution results in solutions with high in vitro infectivity.

EXAMPLE 3

In vitro study of the functional and structural integrity of adenoviral vectors during liquid storage at 25° C. and at 37° C. showed that amino acid based compositions comprising at least three, four and or five excipients, preferably amino acids in combination with a sugar, e.g. sucrose in a ratio of amino acids to sugar of at least 1:2, can remarkably retain infectivity of the viral vectors in cell culture and retain the particle size distribution with polydispersity index values below 0.3.

3.1 Materials and Methods

Compositions 3, 4, 5 and 6 contained the following 3 amino acids:
histidine, glutamic acid, methionine (composition 3),
histidine, lysine, methionine (composition 4),
histidine, glycine, methionine (composition 5) and
histidine, alanine, glutamic acid (composition 6), respectively.

Composition 7 and 8 contained the following 4 amino acids:
histidine, lysine, glycine, arginine (composition 7), and
histidine, lysine, alanine, methionine (composition 8), respectively.

Composition 9 contained the 5 amino acids histidine, glycine, alanine, glutamic acid and methionine.

All compositions additionally contained 40 g/l saccharose and 2 mM $MgCl_2$ in a fixed concentration resulting in different amino acid to sugar ratios of 1:3; 1:1.3; 1:1.6 and 1:1.5 in the case of compositions 3, 4, 5 and 6, respectively. In the case of compositions 7 and 8 the amino acid to sugar ratio was 1.1:1 in both compositions. In composition 9 the amino acid to sugar ratio was adjusted to 1:1.5. The pH value was adjusted in all compositions to 7.4. An adenoviral stock solution stored at −80° C. with a concentration of $1*10^{11}$ IFU/ml in the original supplier formulation (Firma Sirion; Martinsried/Munich; Germany) was employed. The original supplier formulation contained 10 mM HEPES, pH 8, 4 g/l saccharose and 2 mM $MgCl_2$.

3.1.1 Sample Preparation and Liquid Storage

HEK293 cells were transduced with high titres of adenovirus 5 vectors containing the coding DNA for the eGFP protein. 48 h after transduction, cells were harvested and the release of viral particles was performed were released via Na-Deoxycholat and DNase I treatment. Viral particles were purified and concentrated by CsCl gradient ultracentrifugation, followed by buffer exchange in the original supplier formulation on PD10 columns and subsequent determination of the infective titre. The resulting high titre adenoviral stocks were subsequently aliquoted and stored at −80° C. The initial titre of the adenoviral stock solutions in the original supplier formulation was determined to be about $2*10^{11}$ IFU/ml. The adenoviral vector stock solution was re-buffered by dilution to a concentration of $5*10^8$ IFU/ml in stock solutions comprising base components of the compositions according to paragraph section 3.1 above and was subsequently further diluted into the final sample concentration of $1*10^8$ IFU/ml using 1.25×concentrates of compositions according to paragraph section 3.1 above, resulting in the adenoviral vector formulations for subsequent liquid storage. 50 µl of the adenoviral vector formulations were aliquoted in sterile 100 µl PCR vials and subsequently stored for up to 3 months at 5° C. as well as 25° C. and for up to 35 days at 37° C., respectively. At the indicated time points during liquid storage as well as at the initial time point t=0, the infective titres were determined by virus titration in HEK 293 cell cultures according as detailed in to paragraph section 1.1.2 above was determined. In parallel, the hydrodynamic radii of the adenoviral particles and the corresponding polydispersity indices were measured by DLS according as described in section to paragraph 1.1.3 above using a slightly different protocol as follows. The DLS measurements were performed with 10 µl of adenoviral vector preparations diluted with sterile filtrated water (0.02 nm) to suitable concentrations of the adenoviral vector and with acquisition times between 1 and 3 seconds in 80 and 40 cycles, respectively. The resulting autocorrelation functions were analysed using the DynaPro DLS software resulting in the evaluation of the hydrodynamic radii (nm) as well as the particle size distribution with respect to the polydispersity indices (PD1) Special ingredients of the compositions according to the invention contributed to the resulting autocorrelation functions of the analyzed adenovirus particles. Thus, differences of the resulting autocorrelation functions and the compositions without viral vectors led to the calculated results of the DLS measurements.

Electron microscopic analysis was performed as described in paragraph 1.1.4 above.

3.2. Results

Liquid Storage

Liquid storage for 3 months at 5° C. in compositions 3 to 9 according to the invention (paragraph see section 3.1 above) comprising three, four and or five amino acids revealed the complete retention of the infective titre of about $1 \times 10^8$ IFU/ml compared to the positive control (FIG. 19A). In contrast, the infective titre of the adenoviral particles stored in the original supplier formulation was remarkably reduced to approx. $1 \times 10^6$ IFU/ml after liquid storage for three months at 5° C. (FIG. 19A). Moreover, liquid storage of the adenoviral vector particles in the original supplier formulation at 25° C. resulted already after liquid storage for 21 days in a reduction of the infective titre to about $1 \times 10^6$ IFU/ml after liquid storage for 21 days and after liquid storage for 1 month to a further the reduction in the infective titre was further reduced to about $1 \times 10^5$ IFU/ml after liquid storage for 1 month. Further liquid storage for 3 months at 25° C. in the original supplier formulation resulted in the complete loss of the infective titer of the adenoviral particles (FIG. 19B). On the other hand, formulation of the adenoviral particles in compositions 3 to 9 comprising three, four and or five amino acids, respectively, resulted in the nearly complete retention of the infective titres of the adenoviral vector preparations even after liquid storage for 3 months at 25° C. (approx. $1 \times 10^7$ IFU/ml; FIG. 19B). Even liquid storage for 21 days at 37° C. led to a remarkable retention of the infective titre of the adenoviral vector particles formulated in composition 4 and 8 comprising three and or four amino acids, with a residual titre of about $1 \times 10^6$ IFU/ml compared to the complete loss of the infective titre in the original supplier formulation during liquid storage for 21 days at 37° C. While further liquid storage for 35 days at 37° C. led to the loss of infective titre in composition 4, the corresponding titre of the adenoviral vectors was retained to about $1 \times 10^5$ IFU/ml in composition 8 comprising four amino acids (FIG. 19C).

DLS Measurement

The molecular integrity of the adenoviral vector compositions during liquid storage for 14 days to about 35 days at 37° C. was analyzed using DLS measurements. In addition to the evaluation of the hydrodynamic radii of the adenoviral particles, the polydispersity indices (PDI) as well as the values for D10, D50 and D90 as parameters for the particle size distribution in the adenoviral particle compositions were determined. In FIG. 15 shows the PDI values of the adenoviral vectors formulated in composition 6, 8 and 9 in comparison to the corresponding PDI values in the original supplier formulation after liquid storage for 14 days and 35 days at 35° C. are depicted. The initial PDI value at time point t=0 of the adenoviral vector compositions formulated in the original supplier formulation was already remarkably increased (PDI approx. 0.25) associated with a strong standard deviation as compared to the corresponding PDI values in compositions 6, 8 and 9. These findings suggesting the appearance of big particles with fluctuations in size in the original supplier formulation as compared to the adenoviral particles in compositions 6, 8 and 9 with a narrow particle size distribution at time point t=0 (PDI around 0.1). After 14 days of storage at 35° C., the particle size distribution increased in compositions 6, 8 and 9 to different extent slightly but remained between the values of 0.1 and 0.2. In the original supplier formulation, the particle size distribution slightly decreased after liquid storage for 14 days at 37° C. After liquid storage for 35 days at 37° C. the PDI values further increased in all formulations, particularly in the original supplier formulation, where it increased to a PDI value of approx. 0.26 associated with a large standard deviation suggesting the appearance of big particles with variable size. In compositions 6 and 8, the particle size distribution corresponding to the PDI values was also increased but to a minor extent compared to the original supplier formulation, namely in the case of composition 6, the PDI was 0.234 and in the case of composition 8, the PDI was 0.171. The large standard deviation in the original supplier formulation and the remarkable increase in PDI may explain the loss of infectivity in this formulation after liquid storage for 35 days at 37° C. as a result of the appearance of big particles of variable sizes. In contrast, liquid storage of the adenoviral vectors in composition 8 comprising four amino acids resulted in the retention of a PDI value of 0.171 with a small standard deviation suggesting that the appearance of the majority of the measured particles represents infective particles associated with a narrow particle size distribution (FIG. 19D).

Transmission Electron Microscopy

In addition, the molecular integrity of the adenoviral vector preparations formulated in compositions 5 and 8 after liquid storage for 2 months at 25° C. was further analyzed using transmission electron microscopy as described in paragraph section 1.1.4 above. In the acquired electron microscopic images the majority of the adenoviral particles were observed as intact icosahedral shaped bright particles (FIGS. 20 and 21; black arrows). The diameter of the adenoviral particles was measured to be approx. 100 nm from vertex-to-vertex. The adenoviral particles appeared preferentially as single entities. Nevertheless, the background showed the presence of adenoviral vector debris such as large pleomorphous structures and smaller granular structures, possibly representing adenoviral subcomponents such as hexons and fibers. Occasionally, aggregation of adenoviral particles and debris could be observed (FIGS. 20 and 21).

EXAMPLE 4

Analysis of the infective titre of adenoviral vector compositions at the indicated time points during liquid storage at 37° C. revealed a better stabilizing efficacy of a composition comprising 4 amino acids according to the invention as compared to an original supplier formulation.

4.1 Materials and Methods

Composition 11 used in this example contained the four amino acids histidine, lysine, alanine, methionine in combination with 40 g/l saccharose resulting in an amino acid to sugar ratio of 1.1:1. The pH value of the formulation was adjusted to 7.4. For comparison, a standard original supplier formulation 2 comprising 1.522 g/l histidine, 50 g/l saccharose, 1 mM $MgCl_2$, 1.211 g/l Tris, 4.383 g/l NaCl, 0.029 g/l EDTA, 0.005% (v/v) ethanol and 0.2% polysorbat 80 at a pH of 7.4 was applied.

An adenovirus serotype 5 (Ad5) stock solution stored at −80° C. with a concentration of $2\times10^{11}$ IFU/ml in the original supplier formulation (Sirion; Martinsried/Munich; Germany) was employed. The original supplier formulation contained 10 mM HEPES, pH 8, 4 g/l saccharose and 2 mM $MgCl_2$.

4.1.1 Sample Preparation and Liquid Storage

HEK293 cells were transduced with high titres of adenovirus 5 vectors containing the coding DNA for the eGFP protein. 48 h after transduction, cells were harvested and viral particles were released via Na-Deoxycholat and DNase I treatment. Viral particles were purified and concentrated by CsCl gradient ultracentrifugation, followed by buffer exchange in the original supplier formulation on PD10 columns and subsequent determination of the infective titre. The resulting high titre adenoviral stocks were subsequently aliquoted and stored at −80° C. The initial titre of the adenoviral stock solutions in the original supplier formulation was determined to about $2*10^{11}$ IFU/ml. In the first step the adenoviral stock solution with an initial infectivity of $2\times10^{11}$ IFU/ml was 1:2 diluted with the original supplier formulation to get a starting concentration of $1\times10^{11}$ IFU/ml. The adenoviral vector stock solution was re-buffered by 1/200 dilution to a concentration of $5*10^8$ IFU/ml in stock solutions comprising base components of the compositions according to section 4.1 above. Subsequently, samples were further 1:5 diluted with 1.25×concentrates of compositions according to section 4.1 above, to reach the final sample concentration of $1*10^8$ IFU/ml for subsequent liquid storage. 50 µl of the adenoviral vector formulations were aliquoted in sterile 100 µl PCR vials and subsequently stored for up to 21 days at 37° C. Infective titres according to section 1.1.2 above were determined by virus titration in HEK293 cell cultures at the initial time point t=0 and at the indicated time points during liquid storage.

4.2. Results

Liquid Storage

Liquid storage of the adenoviral vectors formulated in composition 11 comprising four amino acids resulted in a better retention of the infective titre after liquid storage for 14 days at 37° C. and more pronounced after liquid storage for 21 days at 37° C. compared to the standard original supplier formulation 2 (FIG. 22). This data further confirmed the results of example 3 above, in which the most effective stabilizing composition also comprised the four amino acids histidine, lysine, alanine, methionine in combination with 40 g/l saccharose in an amino acid to sugar ratio of 1.1:1 (composition 8). Therefore, the combination of the four amino acids histidine, lysine, alanine, methionine in combination with 40 g/l saccharose and an amino acid to sugar ratio of 1.1:1 exhibited superior stabilization of adenoviral vector particles over the standard formulation as described in section 4.1, during thermal stress and liquid storage.

EXAMPLE 5

In vitro study of the functional and structural integrity of adenoviral vectors after different processing steps and subsequent application of several freeze-thaw cycles as well as during liquid storage at 37° C. showed that amino acid based compositions comprising at least three, four and five excipients preferably amino acids in combination with a sugar, e.g. sucrose in a ratio amino acids to sugar of at least 1:2 remarkably retained infectivity of the viral vectors in cell culture and retained the particle size distribution with polydispersity index values below 0.3.

5.1 Materials and Methods

Composition 11 contained the three amino acids alanine, histidine, glutamic acid in combination with 40 g/l saccharose in an amino acid to sugar ratio of 1:1.5. Composition 12 used in this example contained the four amino acids histidine, lysine, alanine, methionine in combination with 40 g/l saccharose resulting in an amino acid to sugar ratio of 1.1:1. The pH values of the formulations were adjusted to 7.4. For comparison, a standard original supplier formulation 2 comprising 1.522 g/l histidine, 50 g/l saccharose, 1 mM $MgCl_2$, 1.211 g/l Tris, 4.383 g/l NaCl, 0.029 g/l EDTA, 0.005% (v/v) ethanol and 0.2% polysorbat 80 at a pH of 7.4 and another standard original supplier formulation 1 comprising 10 mM HEPES, pH 8, 4 g/l saccharose and 2 mM $MgCl_2$ as well as the standard buffer PBS were applied.

An adenovirus serotype 5 (Ad5) stock solution stored at −80° C. with a concentration of $2\times10^{11}$ IFU/ml in the original supplier formulation (Sirion; Martinsried/Munich; Germany) was employed. The original supplier formulation contained 10 mM HEPES, pH 8, 4 g/l saccharose and 2 mM $MgCl_2$.

A Modified Vaccinia Ankara (MVA) viral vector in Tris-HCL (pH 9) was used for freeze-and-thaw experiments and subsequent DLS analyses.

5.1.1 Sample Preparation and Liquid Storage

HEK293 cells were transduced with high titres of adenovirus 5 vectors containing the coding DNA for the eGFP protein. 48 h after transduction, cells were harvested and the release of viral particles was performed via Na-Deoxycholat and DNase I treatment. Viral particles were purified and concentrated by CsCl gradient ultracentrifugation. The further formulation of the adenoviral vector particles was performed in the following two different processing steps.

Processing Step 1:

Adenoviral vector formulations were prepared by re-buffering of the adenoviral vector preparations immediately after CsCl gradient ultracentrifugation. In a first step the obtained concentrated and harvested adenoviral vector band was diluted 1 per 1 in the standard original supplier formulation 1 and re-buffered using dialysis at 2-8° C. in compositions 11 and 12 according to the invention (as described in 5.1) as well as in the standard original supplier formulations 1 and 2 and in the standard buffer PBS.

Processing Step 2:

After ultracentrifugation, the obtained concentrated and harvested adenoviral vector band was diluted 1:1 in the standard original supplier formulation 1 and re-buffered using dialysis at 2-8° C. in the standard original supplier formulation 1. The resulting high titre adenoviral stocks were subsequently aliquoted and stored at −80° C. After thawing the adenoviral vectors in the standard original supplier formulation 1 were re-buffered using dialysis at 2-8° C. for a second time in composition 11 according to the invention (described in paragraph 5.1) and in the standard buffer PBS.

The initial titre of the adenoviral stock solutions in the standard original supplier formulation 3 and 1 as well as in the compositions according to the invention after the both processing steps was determined to be about $1*10^{11}$ IFU/ml. For the subsequent application of several freeze and thaw cycles 50 µl of the high titre adenoviral vector formulations were aliquoted in sterile 100 µl PCR vials and subjected to repeated freeze (1 h at −80° C.) and thaw (1 h at room temperature) cycles. At time point t=0 and after the application of 5, 10, 15 and 20 freeze and thaw cycles the infective titres was determined by virus titration in HEK 293 cell cultures according to paragraph 1.1.2. In parallel, the hydrodynamic radii of the adenoviral particles and the corresponding polydispersity indices were measured by DLS according to paragraph 1.1.3 using a slightly different protocol according to paragraph 3.1.1.

For subsequent liquid storage at 37° C. the high titre adenoviral stock solutions in the different formulations were further diluted to an infective titre of around $1*10^8$ IFU/ml. 50 µl of the diluted adenoviral vector formulations were aliquoted in sterile 100 µl PCR vials and subsequently stored for for up to 28 days at 37° C. At the initial time point t=0 and after 14 days and 28 days of liquid storage at 37° C. the infective titres was determined by virus titration in HEK 293 cell cultures according to paragraph 1.1.2. In parallel, the hydrodynamic radii of the adenoviral particles and the corresponding polydispersity indices were measured by DLS according to paragraph 1.1.3 using a slightly different protocol according to paragraph 3.1.1.

For MVA formulation, composition 13 comprising three amino acids, histidine, methionine, alanine, was used. Subsequently, freeze-thaw cycles were applied and samples were analyzed by DLS.

5.2. Results
Liquid Storage

In FIG. 23, the in vitro infectivity of the adenoviral preparations after the two different processing steps (PS) during liquid storage for up to 28 days at 37° C. is depicted. Formulation of the adenoviral vectors in composition 12 and 11 showed a remarkable higher retention of the infective titre prepared by processing step 1 (PS1) during liquid storage at 37° C. compared to the standard buffer PBS and maintained comparable to the two standard original supplier formulations 2 and 1. Preparation of the adenoviral vector formulations according to processing step 2 (PS2) showed higher stabilization of the infective titre of the adenoviral vectors formulated in compositions 11 compared to the formulation in the standard buffer PBS and even compared to the adenoviral vector preparation in the original supplier formulation prepared by processing step (PS1) during liquid storage for 28 days at 37° C.

In Vitro Infectivity after the Application of Several Freeze and Thaw Cycles

Formulation of the adenoviral vector preparations prepared according to processing step 1 (PS1) in compositions 11 and 12 showed a remarkable maintenance of the in vitro infectivity, particularly after the application of 15 freeze and thaw cycles compared to the original supplier formulations 2 and 1 (FIG. 24A). In contrast, formulation of the adenoviral vector preparations in the standard buffer PBS resulted already after the processing step 1 (PS 1) in the complete loss of the infective titre (FIG. 24A). Moreover, formulation of the adenoviral vector preparations according to processing step 2 in composition 11 showed a nearly complete retention of the in vitro infectivity after application of up to 10 freeze and thaw cycles (FIG. 20B). In contrast, formulation of the adenoviral vector preparations in the standard buffer PBS according to processing step 2 resulted already after the application of 5 freeze and thaw cycles in the complete loss of infectivity (FIG. 24B).

DLS Measurement

Similar observations were made in the parallel performed DLS measurements. Sample preparation according to processing step 1 (PS 1) resulted in the nearly complete retention of the particle size distribution in the adenoviral vector preparations directly after sample preparation (0) expressed in the calculated polydispersity indices smaller 0.3 in the compositions 11 and 12 as well as in the original supplier formulations 1. In contrast, formulation of the adenoviral vector preparations in the standard buffer PBS according to processing step 1 (PS1) showed a higher particle size distribution with polydispersity indices >0.3 already after the preparation and more pronounced after the application of only 5 freeze and thaw cycles. The further application of 10 and 20 freeze and thaw cycles resulted in the complete degradation of the viral particles in formulated PBS. The further application of 5, 10 and 20 freeze and thaw cycles to the adenoviral vector preparation formulated in composition 11 and 12 according to the invention led to the nearly complete retention of the initial particle size distribution<0.3. In contrast, formulation of the adenoviral vector preparations in the original supplier formulation 1 resulted in a remarkably increased PDI>0.3 after the application of 10 as well as 20 freeze and thaw cycles associated with increasing standard deviations, suggesting the appearance of bigger particles with variable size in addition to the main adenoviral vector particles (FIG. 25).

Sample preparation according to processing step 2 (PS 2) revealed the retention of the particle size distribution (PDI<0.3) after application of 5, 10, 15 and 20 freeze and thaw cycles in the case of the adenoviral vector preparations formulated in composition 11 and 12 according to the invention. Contrary, the formulation of the adenoviral vectors in the standard buffer PBS according to processing step 2 (PS 2) resulted in the complete loss of intact adenoviral particles after the application of 10, 15 and 20 freeze and thaw cycles.

Similar experiments were performed with MVA in composition 13 compared to the original supplier formulations 2 and 1 and PBS (FIG. 26). When MVA was formulated in composition 13, the PDI was smaller than 0.5. In contrast, in the original supplier formulations 1 and 2 already after sample preparation and after the application of 20 freeze-thaw cycles showed PDI values higher than 0.5.

The invention claimed is:

1. A method for preparing liquid compositions of replication-deficient and infectious viral vector-based compositions for storage as a liquid, wherein the viral vector-based particles present in the composition are used to deliver genetic material into cells, the method comprising the steps:
   (a) providing replication-deficient viral vectors;
   (b) providing a solution comprising at least one sugar and at least three different amino acids, wherein the three different amino acids are selected from at least three different groups from the following: amino acids with a polar functional group, amino acids with an aliphatic functional group, amino acids with an aromatic functional group, amino acids with a negatively charged functional group, and amino acids with a positively charged functional group; and wherein the solution comprises an amino acid-sugar ratio of no more than twice the amount of sugar as compared to the amount of amino acids; and
   (c) mixing the replication deficient viral vectors of step (a) with the solution of step (b) to form a mixture; and
   (d) storing the mixture of step (c) as a liquid; and
   wherein the method does not comprise drying the mixture.

2. The method of claim 1, wherein storing the mixture in step (d) comprises storing for at least 28 days.

3. The method according to claim 1, wherein the viral vector is selected from the group consisting of MVA, adenovirus, Adenovirus-associated virus (AAV), lentivirus, vesicular stomatitis virus (VSV), or herpesviruses.

4. The method according to claim 1, wherein the replication-deficient viral vector is a virus like particle.

5. The method according to claim 1, further comprising adding an antigenic polypeptide.

6. The method according to claim 1, further comprising adding at least one adjuvant.

7. The method according to claim 1, wherein the replication-deficient viral vectors of (a) are replication-deficient viral vectors that have been reconstituted immediately after harvesting from cell cultures and purification.

8. A viral vector-based composition obtained or obtainable by the method according to claim 1.

9. The viral vector-based composition of claim 8 for use as a prime-boost vaccine.

10. The viral vector-based composition according to claim 7, wherein the viral vector-based composition is for intramuscular, subcutaneous, intradermal, transdermal, oral, peroral, nasal, and/or inhalative application.

* * * * *